US011635427B2

(12) United States Patent
Samuels et al.

(10) Patent No.: US 11,635,427 B2
(45) Date of Patent: Apr. 25, 2023

(54) SANDWICH ASSAYS IN DROPLETS

(71) Applicant: Bio-Rad Laboratories, Inc., Hercules, CA (US)

(72) Inventors: Michael L. Samuels, Windham, NH (US); Darren Roy Link, Lexington, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 301 days.

(21) Appl. No.: 16/937,908

(22) Filed: Jul. 24, 2020

(65) Prior Publication Data

US 2021/0041432 A1 Feb. 11, 2021

Related U.S. Application Data

(63) Continuation of application No. 15/415,276, filed on Jan. 25, 2017, now Pat. No. 10,761,090, which is a continuation of application No. 13/250,702, filed on Sep. 30, 2011, now Pat. No. 9,562,897.

(60) Provisional application No. 61/388,413, filed on Sep. 30, 2010.

(51) Int. Cl.
*G01N 33/543* (2006.01)
*C40B 40/04* (2006.01)
*G01N 33/532* (2006.01)
*C40B 40/00* (2006.01)
*C12Q 1/6874* (2018.01)
*B01F 33/3011* (2022.01)
*B01F 33/302* (2022.01)
*C40B 70/00* (2006.01)

(52) U.S. Cl.
CPC ..... *G01N 33/54366* (2013.01); *C12Q 1/6874* (2013.01); *C40B 40/00* (2013.01); *C40B 40/04* (2013.01); *C40B 70/00* (2013.01); *G01N 33/532* (2013.01); *B01F 33/3011* (2022.01); *B01F 33/3021* (2022.01)

(58) Field of Classification Search
None
See application file for complete search history.

(56) References Cited

U.S. PATENT DOCUMENTS

| 2,097,692 | A | 11/1937 | Fiegel |
| 2,164,172 | A | 6/1939 | Dalton |
| 2,636,855 | A | 4/1953 | Schwartz |
| 2,656,508 | A | 10/1953 | Coulter |
| 2,692,800 | A | 10/1954 | Nichols et al. |
| 2,797,149 | A | 6/1957 | Skeggs |
| 2,879,141 | A | 3/1959 | Skeggs |
| 2,971,700 | A | 2/1961 | Peeps |
| 3,479,141 | A | 11/1969 | Smythe et al. |
| 3,608,821 | A | 9/1971 | Simm et al. |
| 3,621,059 | A | 11/1971 | Bartlett |
| 3,698,635 | A | 10/1972 | Sickles |
| 3,784,471 | A | 1/1974 | Kaiser |
| 3,816,331 | A | 6/1974 | Brown, Jr. et al. |
| 3,930,061 | A | 12/1975 | Scharfenberger |
| 3,960,187 | A | 6/1976 | Stock et al. |
| 3,980,541 | A | 9/1976 | Aine |
| 3,982,541 | A | 9/1976 | L'Esperance, Jr. |
| 4,014,469 | A | 3/1977 | Sato |
| 4,022,575 | A | 5/1977 | Hansen et al. |
| 4,034,966 | A | 7/1977 | Suh et al. |
| 4,059,552 | A | 11/1977 | Zweigle et al. |
| 4,091,042 | A | 5/1978 | Alexanderson et al. |
| 4,117,550 | A | 9/1978 | Folland et al. |
| 4,130,394 | A | 12/1978 | Negersmith |
| 4,210,809 | A | 7/1980 | Pelavin |
| 4,253,846 | A | 3/1981 | Smythe et al. |
| 4,266,721 | A | 5/1981 | Sickles |
| 4,279,345 | A | 7/1981 | Allred |
| 4,297,345 | A | 10/1981 | Howarth |
| 4,315,754 | A | 2/1982 | Ruzicka et al. |
| 4,378,957 | A | 4/1983 | Malkin et al. |
| 4,383,767 | A | 5/1983 | Jido |
| 4,439,980 | A | 4/1984 | Biblarz et al. |
| 4,508,265 | A | 4/1985 | Jido |
| 4,533,634 | A | 8/1985 | Maldonado et al. |

(Continued)

FOREIGN PATENT DOCUMENTS

| AT | 140025 T | 7/1996 |
| AT | 140880 T | 8/1996 |

(Continued)

OTHER PUBLICATIONS

Klein et al., "Droplet Barcoding for Single-Cell Transcriptomics Applied to Embryonic Stem Cells," Cell 2015, 161:1187-1201. (Year: 2015).*
Pelham, 1976, An efficient mRNA-dependent translation system from reticulocyte lysates, Eur J Biochem 67:247-56.
Pelletier, 1999, An in vivo library-versus-library selection of optimized protein-protein interactions, Nature Biotechnology, 17:683-90.

(Continued)

*Primary Examiner* — Kaijiang Zhang
(74) *Attorney, Agent, or Firm* — Withers Bergman, LLP; Thomas C. Meyers

(57) ABSTRACT

The invention generally relates to performing sandwich assays in droplets. In certain embodiments, the invention provides methods for detecting a target analyte that involve forming a compartmentalized portion of fluid including a portion of a sample suspected of containing a target analyte and a sample identifier, a first binding agent having a target identifier, and a second binding agent specific to the target analyte under conditions that produce a complex of the first and second binding agents with the target analyte, separating the complexes, and detecting the complexes, thereby detecting the target analyte.

20 Claims, 19 Drawing Sheets

Specification includes a Sequence Listing.

(56) References Cited

U.S. PATENT DOCUMENTS

| | | |
|---|---|---|
| 4,585,209 A | 4/1986 | Aine et al. |
| 4,618,476 A | 10/1986 | Columbus |
| 4,675,285 A | 6/1987 | Clark et al. |
| 4,676,274 A | 6/1987 | Brown |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,767,515 A | 8/1988 | Scott et al. |
| 4,767,929 A | 8/1988 | Valentine |
| 4,779,805 A | 10/1988 | Jackson et al. |
| 4,795,330 A | 1/1989 | Noakes et al. |
| 4,801,086 A | 1/1989 | Noakes |
| 4,801,529 A | 1/1989 | Perlman |
| 4,829,996 A | 5/1989 | Noakes et al. |
| 4,853,336 A | 8/1989 | Saros et al. |
| 4,856,363 A | 8/1989 | LaRocca et al. |
| 4,859,363 A | 8/1989 | Davis et al. |
| 4,865,444 A | 9/1989 | Green et al. |
| 4,883,750 A | 11/1989 | Whiteley et al. |
| 4,908,112 A | 3/1990 | Pace |
| 4,931,225 A | 6/1990 | Cheng |
| 4,941,959 A | 7/1990 | Scott |
| 4,962,885 A | 10/1990 | Coffee |
| 4,963,498 A | 10/1990 | Hillman et al. |
| 4,981,580 A | 1/1991 | Auer |
| 4,996,004 A | 2/1991 | Bucheler et al. |
| 5,055,390 A | 10/1991 | Weaver et al. |
| 5,091,652 A | 2/1992 | Mathies et al. |
| 5,096,615 A | 3/1992 | Prescott et al. |
| 5,104,813 A | 4/1992 | Besemer et al. |
| 5,122,360 A | 6/1992 | Harris et al. |
| 5,149,625 A | 9/1992 | Church et al. |
| 5,180,662 A | 1/1993 | Sitkovsky |
| 5,185,099 A | 2/1993 | Delpuech et al. |
| 5,188,290 A | 2/1993 | Gebauer et al. |
| 5,188,291 A | 2/1993 | Cross |
| 5,192,659 A | 3/1993 | Simons |
| 5,204,112 A | 4/1993 | Hope et al. |
| 5,207,973 A | 5/1993 | Harris et al. |
| 5,241,159 A | 8/1993 | Chatteriee et al. |
| 5,260,466 A | 11/1993 | McGibbon |
| 5,262,027 A | 11/1993 | Scott |
| 5,270,163 A | 12/1993 | Gold et al. |
| 5,296,375 A | 3/1994 | Kricka et al. |
| 5,304,487 A | 4/1994 | Wilding et al. |
| 5,310,653 A | 5/1994 | Hanausek-Walaszek et al. |
| 5,313,009 A | 5/1994 | Guenkel et al. |
| 5,333,675 A | 8/1994 | Mullis et al. |
| 5,344,594 A | 9/1994 | Sheridon |
| 5,354,670 A | 10/1994 | Nickoloff et al. |
| 5,376,252 A | 12/1994 | Ekstrom et al. |
| 5,378,957 A | 1/1995 | Kelly |
| 5,397,605 A | 3/1995 | Barbieri et al. |
| 5,399,461 A | 3/1995 | Van et al. |
| 5,399,491 A | 3/1995 | Kacian et al. |
| 5,403,617 A | 4/1995 | Haaland |
| 5,413,924 A | 5/1995 | Kosak et al. |
| 5,417,235 A | 5/1995 | Wise et al. |
| 5,427,946 A | 6/1995 | Kricka et al. |
| 5,445,934 A | 8/1995 | Fodor et al. |
| 5,452,878 A | 9/1995 | Gravesen et al. |
| 5,452,955 A | 9/1995 | Lundstrom |
| 5,454,472 A | 10/1995 | Benecke et al. |
| 5,460,945 A | 10/1995 | Springer et al. |
| 5,468,613 A | 11/1995 | Erlich et al. |
| 5,475,096 A | 12/1995 | Gold et al. |
| 5,475,610 A | 12/1995 | Atwood et al. |
| 5,480,614 A | 1/1996 | Kamahori |
| 5,486,335 A | 1/1996 | Wilding et al. |
| 5,498,392 A | 3/1996 | Wilding et al. |
| 5,498,523 A | 3/1996 | Tabor et al. |
| 5,500,415 A | 3/1996 | Dollat et al. |
| 5,503,851 A | 4/1996 | Mank et al. |
| 5,512,131 A | 4/1996 | Kumar et al. |
| 5,516,635 A | 5/1996 | Ekins et al. |
| 5,518,709 A | 5/1996 | Sutton et al. |
| 5,523,162 A | 6/1996 | Franz et al. |
| 5,587,128 A | 12/1996 | Wilding et al. |
| 5,589,136 A | 12/1996 | Northrup et al. |
| 5,602,756 A | 2/1997 | Atwood et al. |
| 5,604,097 A | 2/1997 | Brenner |
| 5,610,016 A | 3/1997 | Sato et al. |
| 5,612,188 A | 3/1997 | Shuler et al. |
| 5,616,478 A | 4/1997 | Chetverin et al. |
| 5,617,997 A | 4/1997 | Kobayashi et al. |
| 5,635,358 A | 6/1997 | Wilding et al. |
| 5,636,400 A | 6/1997 | Young |
| 5,641,658 A | 6/1997 | Adams et al. |
| 5,643,729 A | 7/1997 | Taniguchi et al. |
| 5,655,517 A | 8/1997 | Coffee |
| 5,656,155 A | 8/1997 | Norcross et al. |
| 5,656,493 A | 8/1997 | Mullis et al. |
| 5,661,222 A | 8/1997 | Hare |
| 5,662,874 A | 9/1997 | David |
| 5,670,325 A | 9/1997 | Lapidus et al. |
| 5,681,600 A | 10/1997 | Antinone et al. |
| 5,695,934 A | 12/1997 | Brenner |
| 5,726,026 A | 3/1998 | Wilding et al. |
| 5,726,404 A | 3/1998 | Brody |
| 5,733,526 A | 3/1998 | Trevino et al. |
| 5,739,036 A | 4/1998 | Parris |
| 5,744,366 A | 4/1998 | Kricka et al. |
| 5,750,988 A | 5/1998 | Apffel et al. |
| 5,762,775 A | 6/1998 | DePaoli |
| 5,779,868 A | 7/1998 | Parce et al. |
| 5,783,431 A | 7/1998 | Peterson et al. |
| 5,840,506 A | 11/1998 | Giordano |
| 5,846,719 A | 12/1998 | Brenner et al. |
| 5,849,491 A | 12/1998 | Radomski et al. |
| 5,851,769 A | 12/1998 | Gray et al. |
| 5,858,187 A | 1/1999 | Ramsey et al. |
| 5,858,655 A | 1/1999 | Arnold |
| 5,858,670 A | 1/1999 | Lam et al. |
| 5,863,722 A | 1/1999 | Brenner |
| 5,868,322 A | 2/1999 | Loucks |
| 5,872,010 A | 2/1999 | Karger et al. |
| 5,876,771 A | 3/1999 | Sizer et al. |
| 5,880,071 A | 3/1999 | Parce et al. |
| 5,882,680 A | 3/1999 | Suzuki et al. |
| 5,882,856 A | 3/1999 | Shuber |
| 5,884,846 A | 3/1999 | Tan |
| 5,887,755 A | 3/1999 | Hood, III |
| 5,888,746 A | 3/1999 | Tabiti et al. |
| 5,888,778 A | 3/1999 | Shuber |
| 5,904,933 A | 5/1999 | Riess et al. |
| 5,921,678 A | 7/1999 | Desai et al. |
| 5,927,852 A | 7/1999 | Serafin |
| 5,928,870 A | 7/1999 | Lapidus et al. |
| 5,932,100 A | 8/1999 | Yager et al. |
| 5,935,331 A | 8/1999 | Naka et al. |
| 5,942,056 A | 8/1999 | Singh |
| 5,942,443 A | 8/1999 | Parce et al. |
| 5,958,203 A | 9/1999 | Parce et al. |
| 5,972,187 A | 10/1999 | Parce et al. |
| 5,980,936 A | 11/1999 | Krafft et al. |
| 5,989,815 A | 11/1999 | Skolnick et al. |
| 5,989,892 A | 11/1999 | Nishimaki et al. |
| 5,995,341 A | 11/1999 | Tanaka et al. |
| 5,997,636 A | 12/1999 | Gamarnik et al. |
| 6,008,003 A | 12/1999 | Haak-Frendscho et al. |
| 6,023,540 A | 2/2000 | Walt et al. |
| 6,028,066 A | 2/2000 | Unger |
| 6,042,709 A | 3/2000 | Parce et al. |
| 6,045,755 A | 4/2000 | Lebl et al. |
| 6,046,056 A | 4/2000 | Parce et al. |
| 6,048,551 A | 4/2000 | Hilfinger et al. |
| 6,048,690 A | 4/2000 | Heller et al. |
| 6,068,199 A | 5/2000 | Coffee |
| 6,074,879 A | 6/2000 | Zelmanovic et al. |
| 6,080,295 A | 6/2000 | Parce et al. |
| 6,086,740 A | 7/2000 | Kennedy |
| 6,096,495 A | 8/2000 | Kasai et al. |
| 6,103,537 A | 8/2000 | Ullman et al. |

(56) References Cited

U.S. PATENT DOCUMENTS

| | | |
|---|---|---|
| 6,105,571 A | 8/2000 | Coffee |
| 6,105,877 A | 8/2000 | Coffee |
| 6,107,059 A | 8/2000 | Hart |
| 6,116,516 A | 9/2000 | Ganan-Calvo |
| 6,118,849 A | 9/2000 | Tanimori et al. |
| 6,119,953 A | 9/2000 | Ganan-Calvo et al. |
| 6,120,666 A | 9/2000 | Jacobson et al. |
| 6,124,388 A | 9/2000 | Takai et al. |
| 6,124,439 A | 9/2000 | Friedman et al. |
| 6,130,052 A | 10/2000 | Van Baren et al. |
| 6,130,098 A | 10/2000 | Handique et al. |
| 6,137,214 A | 10/2000 | Raina |
| 6,138,077 A | 10/2000 | Brenner |
| 6,139,303 A | 10/2000 | Reed et al. |
| 6,140,053 A | 10/2000 | Koster |
| 6,143,496 A | 11/2000 | Brown et al. |
| 6,146,828 A | 11/2000 | Lapidus et al. |
| 6,149,789 A | 11/2000 | Benecke et al. |
| 6,150,180 A | 11/2000 | Parce et al. |
| 6,150,516 A | 11/2000 | Brenner et al. |
| 6,162,421 A | 12/2000 | Ordino et al. |
| 6,165,778 A | 12/2000 | Kedar |
| 6,171,796 B1 | 1/2001 | An et al. |
| 6,171,850 B1 | 1/2001 | Nagle et al. |
| 6,172,214 B1 | 1/2001 | Brenner |
| 6,172,218 B1 | 1/2001 | Brenner |
| 6,174,160 B1 | 1/2001 | Lee et al. |
| 6,174,469 B1 | 1/2001 | Gañan-Calvo |
| 6,177,479 B1 | 1/2001 | Nakajima |
| 6,180,372 B1 | 1/2001 | Franzen |
| 6,184,012 B1 | 2/2001 | Neri et al. |
| 6,187,214 B1 | 2/2001 | Ganan-Calvo |
| 6,189,803 B1 | 2/2001 | Ganan-Calvo |
| 6,196,525 B1 | 3/2001 | Ganan-Calvo |
| 6,197,335 B1 | 3/2001 | Sherman |
| 6,197,835 B1 | 3/2001 | Ganan-Calvo |
| 6,203,993 B1 | 3/2001 | Shuber et al. |
| 6,207,372 B1 | 3/2001 | Shuber |
| 6,207,397 B1 | 3/2001 | Lynch et al. |
| 6,210,396 B1 | 4/2001 | MacDonald et al. |
| 6,210,891 B1 | 4/2001 | Nyren et al. |
| 6,210,896 B1 | 4/2001 | Chan |
| 6,214,558 B1 | 4/2001 | Shuber et al. |
| 6,221,654 B1 | 4/2001 | Quake et al. |
| 6,227,466 B1 | 5/2001 | Hartman et al. |
| 6,234,402 B1 | 5/2001 | Ganan-Calvo |
| 6,235,383 B1 | 5/2001 | Hong et al. |
| 6,235,475 B1 | 5/2001 | Brenner et al. |
| 6,241,159 B1 | 6/2001 | Ganan-Calvo et al. |
| 6,243,373 B1 | 6/2001 | Turock |
| 6,248,378 B1 | 6/2001 | Ganan-Calvo |
| 6,251,661 B1 | 6/2001 | Urabe et al. |
| 6,252,129 B1 | 6/2001 | Coffee |
| 6,258,568 B1 | 7/2001 | Nyren |
| 6,258,858 B1 | 7/2001 | Nakajima et al. |
| 6,261,797 B1 | 7/2001 | Sorge et al. |
| 6,263,222 B1 | 7/2001 | Diab et al. |
| 6,266,459 B1 | 7/2001 | Walt et al. |
| 6,267,353 B1 | 7/2001 | Friedline et al. |
| 6,267,858 B1 | 7/2001 | Parce et al. |
| 6,268,152 B1 | 7/2001 | Fodor et al. |
| 6,268,165 B1 | 7/2001 | O'Brien |
| 6,268,222 B1 | 7/2001 | Chandler et al. |
| 6,274,320 B1 | 8/2001 | Rothberg et al. |
| 6,274,337 B1 | 8/2001 | Parce et al. |
| 6,280,948 B1 | 8/2001 | Guilloyle et al. |
| 6,292,756 B1 | 9/2001 | Lievois et al. |
| 6,294,344 B1 | 9/2001 | O'Brien |
| 6,296,020 B1 | 10/2001 | McNeely et al. |
| 6,296,673 B1 | 10/2001 | Santarsiero et al. |
| 6,299,145 B1 | 10/2001 | Ganan-Calvo |
| 6,301,055 B1 | 10/2001 | Legrand et al. |
| 6,306,659 B1 | 10/2001 | Parce et al. |
| 6,310,354 B1 | 10/2001 | Hanninen et al. |
| 6,310,653 B1 | 10/2001 | Malcolm, Jr. et al. |
| 6,316,208 B1 | 11/2001 | Roberts et al. |
| 6,316,213 B1 | 11/2001 | O'Brien |
| 6,318,640 B1 | 11/2001 | Coffee |
| 6,326,145 B1 | 12/2001 | Whitcombe et al. |
| 6,336,463 B1 | 1/2002 | Ohta |
| 6,344,325 B1 | 2/2002 | Quake et al. |
| 6,352,828 B1 | 3/2002 | Brenner |
| 6,355,193 B1 | 3/2002 | Stott |
| 6,355,198 B1 | 3/2002 | Kim et al. |
| 6,357,670 B2 | 3/2002 | Ganan-Calvo |
| 6,386,463 B1 | 5/2002 | Ganan-Calvo |
| 6,391,559 B1 | 5/2002 | Brown et al. |
| 6,394,429 B2 | 5/2002 | Ganan-Calvo |
| 6,399,339 B1 | 6/2002 | Wolberg et al. |
| 6,399,389 B1 | 6/2002 | Parce et al. |
| 6,403,373 B1 | 6/2002 | Scanlan et al. |
| 6,405,936 B1 | 6/2002 | Ganan-Calvo |
| 6,408,878 B2 | 6/2002 | Unger et al. |
| 6,409,832 B2 | 6/2002 | Weigl et al. |
| 6,429,025 B1 | 8/2002 | Parce et al. |
| 6,429,148 B1 | 8/2002 | Chu et al. |
| 6,432,143 B2 | 8/2002 | Kubiak et al. |
| 6,432,148 B1 | 8/2002 | Ganan-Calvo |
| 6,432,630 B1 | 8/2002 | Blankenstein |
| 6,439,103 B1 | 8/2002 | Miller |
| 6,440,706 B1 | 8/2002 | Vogelstein et al. |
| 6,440,760 B1 | 8/2002 | Cho et al. |
| 6,450,139 B1 | 9/2002 | Watanabe |
| 6,450,189 B1 | 9/2002 | Ganan-Calvo |
| 6,454,193 B1 | 9/2002 | Busick et al. |
| 6,464,336 B1 | 10/2002 | Sharma |
| 6,464,886 B2 | 10/2002 | Ganan-Calvo |
| 6,475,441 B1 | 11/2002 | Parce et al. |
| 6,481,648 B1 | 11/2002 | Zimmermann |
| 6,489,103 B1 | 12/2002 | Griffiths et al. |
| 6,503,933 B1 | 1/2003 | Moloney et al. |
| 6,506,609 B1 | 1/2003 | Wada et al. |
| 6,508,988 B1 | 1/2003 | Van Dam et al. |
| 6,511,803 B1 | 1/2003 | Church et al. |
| 6,520,425 B1 | 2/2003 | Reneker |
| 6,524,456 B1 | 2/2003 | Ramsey et al. |
| 6,540,395 B2 | 4/2003 | Muhlbauer et al. |
| 6,540,895 B1 | 4/2003 | Spence et al. |
| 6,551,836 B1 | 4/2003 | Chow et al. |
| 6,553,944 B1 | 4/2003 | Allen et al. |
| 6,553,960 B1 | 4/2003 | Yoshikawa et al. |
| 6,554,202 B2 | 4/2003 | Ganan-Calvo |
| 6,557,334 B2 | 5/2003 | Jager |
| 6,557,834 B2 | 5/2003 | Ganan-Calvo |
| 6,558,944 B1 | 5/2003 | Parce et al. |
| 6,558,960 B1 | 5/2003 | Parce et al. |
| 6,560,030 B2 | 5/2003 | Legrand et al. |
| 6,565,010 B2 | 5/2003 | Anderson et al. |
| 6,569,631 B1 | 5/2003 | Pantoliano et al. |
| 6,576,420 B1 | 6/2003 | Carson et al. |
| 6,591,852 B1 | 7/2003 | McNeely et al. |
| 6,592,321 B2 | 7/2003 | Bonker et al. |
| 6,592,821 B1 | 7/2003 | Wada et al. |
| 6,601,613 B2 | 8/2003 | McNeely et al. |
| 6,608,726 B2 | 8/2003 | Legrand et al. |
| 6,610,499 B1 | 8/2003 | Fulwyler et al. |
| 6,614,598 B1 | 9/2003 | Quake et al. |
| 6,627,603 B1 | 9/2003 | Bibette et al. |
| 6,630,006 B2 | 10/2003 | Santarsiero et al. |
| 6,630,353 B1 | 10/2003 | Parce et al. |
| 6,632,619 B1 | 10/2003 | Harrison et al. |
| 6,637,463 B1 | 10/2003 | Lei et al. |
| 6,638,749 B1 | 10/2003 | Beckman et al. |
| 6,645,432 B1 | 11/2003 | Anderson et al. |
| 6,646,253 B1 | 11/2003 | Rohwer et al. |
| 6,653,626 B2 | 11/2003 | Fischer et al. |
| 6,656,267 B2 | 12/2003 | Newman |
| 6,659,370 B1 | 12/2003 | Inoue |
| 6,660,252 B2 | 12/2003 | Matathia et al. |
| 6,670,142 B2 | 12/2003 | Lau et al. |
| 6,679,441 B1 | 1/2004 | Borra et al. |
| 6,680,178 B2 | 1/2004 | Harris et al. |
| 6,682,890 B2 | 1/2004 | Mack et al. |
| 6,717,136 B2 | 4/2004 | Andersson et al. |

(56) References Cited

U.S. PATENT DOCUMENTS

| | | |
|---|---|---|
| 6,729,561 B2 | 5/2004 | Hirae et al. |
| 6,738,502 B1 | 5/2004 | Coleman et al. |
| 6,739,036 B2 | 5/2004 | Koike et al. |
| 6,744,046 B2 | 6/2004 | Valaskovic et al. |
| 6,752,922 B2 | 6/2004 | Huang et al. |
| 6,753,147 B2 | 6/2004 | Vogelstein et al. |
| 6,766,817 B2 | 7/2004 | da Silva |
| 6,767,194 B2 | 7/2004 | Jeon et al. |
| 6,767,704 B2 | 7/2004 | Waldman et al. |
| 6,790,328 B2 | 9/2004 | Jacobson et al. |
| 6,793,753 B2 | 9/2004 | Unger et al. |
| 6,797,056 B2 | 9/2004 | David |
| 6,800,849 B2 | 10/2004 | Staats |
| 6,806,058 B2 | 10/2004 | Jesperson et al. |
| 6,808,382 B2 | 10/2004 | Lanfranchi |
| 6,808,882 B2 | 10/2004 | Griffiths et al. |
| 6,814,980 B2 | 11/2004 | Levy et al. |
| 6,818,395 B1 | 11/2004 | Quake et al. |
| 6,832,787 B1 | 12/2004 | Renzi |
| 6,833,242 B2 | 12/2004 | Quake et al. |
| 6,841,350 B2 | 1/2005 | Ogden et al. |
| 6,872,250 B2 | 3/2005 | David et al. |
| 6,890,487 B1 | 5/2005 | Sklar et al. |
| 6,897,018 B1 | 5/2005 | Yuan et al. |
| 6,905,844 B2 | 6/2005 | Kim |
| 6,918,404 B2 | 7/2005 | Dias da Silva |
| 6,926,313 B1 | 8/2005 | Renzi |
| 6,935,768 B2 | 8/2005 | Lowe et al. |
| 6,936,417 B2 | 8/2005 | Orntoft |
| 6,942,978 B1 | 9/2005 | O'Brien |
| 6,949,342 B2 | 9/2005 | Golub et al. |
| 6,960,437 B2 | 11/2005 | Enzelberger et al. |
| 6,964,847 B1 | 11/2005 | Englert |
| 6,974,667 B2 | 12/2005 | Horne et al. |
| 6,998,232 B1 | 2/2006 | Feinstein et al. |
| 7,022,472 B2 | 4/2006 | Robbins et al. |
| 7,041,481 B2 | 5/2006 | Anderson et al. |
| 7,049,072 B2 | 5/2006 | Seshi |
| 7,056,674 B2 | 6/2006 | Baker et al. |
| 7,057,026 B2 | 6/2006 | Barnes et al. |
| 7,066,586 B2 | 6/2006 | da Silva |
| 7,068,874 B2 | 6/2006 | Wang et al. |
| 7,078,180 B2 | 7/2006 | Genetta |
| 7,081,192 B1 | 7/2006 | Wang et al. |
| 7,081,340 B2 | 7/2006 | Baker et al. |
| 7,090,983 B1 | 8/2006 | Muramatsu et al. |
| 7,115,230 B2 | 10/2006 | Sundararajan |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,153,700 B1 | 12/2006 | Pardee et al. |
| 7,156,917 B2 | 1/2007 | Moriyama et al. |
| 7,163,801 B2 | 1/2007 | Reed |
| 7,169,560 B2 | 1/2007 | Lapidus et al. |
| 7,171,311 B2 | 1/2007 | Dai et al. |
| 7,198,899 B2 | 4/2007 | Schleyer et al. |
| 7,204,431 B2 | 4/2007 | Li et al. |
| 7,229,770 B1 | 6/2007 | Price et al. |
| 7,252,943 B2 | 8/2007 | Griffiths et al. |
| 7,267,938 B2 | 9/2007 | Anderson et al. |
| 7,268,167 B2 | 9/2007 | Higuchi et al. |
| 7,282,337 B1 | 10/2007 | Harris |
| 7,291,462 B2 | 11/2007 | O'Brien et al. |
| 7,294,503 B2 | 11/2007 | Quake et al. |
| 7,300,765 B2 | 11/2007 | Patel |
| 7,308,364 B2 | 12/2007 | Shaughnessy et al. |
| 7,314,721 B2 | 1/2008 | Gure et al. |
| 7,316,906 B2 | 1/2008 | Chiorazzi et al. |
| 7,323,305 B2 | 1/2008 | Leamon et al. |
| 7,326,529 B2 | 2/2008 | Ali et al. |
| 7,332,280 B2 | 2/2008 | Levy et al. |
| 7,332,590 B2 | 2/2008 | Nacht et al. |
| 7,341,211 B2 | 3/2008 | Ganan Calvo et al. |
| 7,348,142 B2 | 3/2008 | Wang |
| 7,358,231 B1 | 4/2008 | McCaffey et al. |
| 7,361,474 B2 | 4/2008 | Siegler |
| 7,364,862 B2 | 4/2008 | Ali et al. |
| 7,368,255 B2 | 5/2008 | Bae et al. |
| 7,378,233 B2 | 5/2008 | Sidransky et al. |
| 7,378,280 B2 | 5/2008 | Quake et al. |
| 7,390,463 B2 | 6/2008 | He et al. |
| 7,393,634 B1 | 7/2008 | Ahuja et al. |
| 7,393,665 B2 | 7/2008 | Brenner |
| 7,416,851 B2 | 8/2008 | Davi et al. |
| 7,429,467 B2 | 9/2008 | Holliger et al. |
| 7,432,064 B2 | 10/2008 | Salceda et al. |
| 7,442,507 B2 | 10/2008 | Polsky et al. |
| 7,449,303 B2 | 11/2008 | Coignet |
| 7,468,271 B2 | 12/2008 | Golovchenko et al. |
| 7,473,530 B2 | 1/2009 | Huttemann |
| 7,473,531 B1 | 1/2009 | Domon et al. |
| 7,476,506 B2 | 1/2009 | Schleyer et al. |
| 7,479,370 B2 | 1/2009 | Coignet |
| 7,479,371 B2 | 1/2009 | Ando et al. |
| 7,479,376 B2 | 1/2009 | Waldman et al. |
| 7,482,129 B2 | 1/2009 | Soyupak et al. |
| 7,501,244 B2 | 3/2009 | Reinhard et al. |
| 7,504,214 B2 | 3/2009 | Erlander et al. |
| 7,507,532 B2 | 3/2009 | Chang et al. |
| 7,507,541 B2 | 3/2009 | Raitano et al. |
| 7,510,707 B2 | 3/2009 | Platica et al. |
| 7,510,842 B2 | 3/2009 | Podust et al. |
| 7,514,209 B2 | 4/2009 | Dai et al. |
| 7,514,210 B2 | 4/2009 | Holliger et al. |
| 7,524,633 B2 | 4/2009 | Sidransky |
| 7,527,933 B2 | 5/2009 | Sahin et al. |
| 7,537,897 B2 | 5/2009 | Brenner et al. |
| 7,541,383 B2 | 6/2009 | Fu et al. |
| 7,544,473 B2 | 6/2009 | Brenner |
| 7,556,776 B2 | 7/2009 | Fraden et al. |
| 7,582,446 B2 | 9/2009 | Griffiths et al. |
| 7,595,195 B2 | 9/2009 | Lee et al. |
| 7,604,938 B2 | 10/2009 | Takahashi et al. |
| 7,622,081 B2 | 11/2009 | Chou et al. |
| 7,632,562 B2 | 12/2009 | Nair et al. |
| 7,635,562 B2 | 12/2009 | Harris et al. |
| 7,638,276 B2 | 12/2009 | Griffiths et al. |
| 7,655,435 B2 | 2/2010 | Holliger et al. |
| 7,655,470 B2 | 2/2010 | Ismagilov et al. |
| 7,666,593 B2 | 2/2010 | Lapidus |
| 7,691,576 B2 | 4/2010 | Holliger et al. |
| 7,698,287 B2 | 4/2010 | Becker et al. |
| 7,708,949 B2 | 5/2010 | Stone et al. |
| 7,718,578 B2 | 5/2010 | Griffiths et al. |
| 7,736,890 B2 | 6/2010 | Sia et al. |
| 7,741,130 B2 | 6/2010 | Lee, Jr. et al. |
| RE41,780 E | 9/2010 | Anderson et al. |
| 7,814,175 B1 | 10/2010 | Chang et al. |
| 7,824,889 B2 | 11/2010 | Vogelstein et al. |
| 7,888,017 B2 | 2/2011 | Quake et al. |
| 7,897,044 B2 | 3/2011 | Hoyos et al. |
| 7,897,341 B2 | 3/2011 | Griffiths et al. |
| 7,901,939 B2 | 3/2011 | Ismagliov et al. |
| 7,915,015 B2 | 3/2011 | Vogelstein et al. |
| 7,968,287 B2 | 6/2011 | Griffiths et al. |
| 7,990,525 B2 | 8/2011 | Kanda |
| 8,012,382 B2 | 9/2011 | Kim et al. |
| 8,067,159 B2 | 11/2011 | Brown et al. |
| 8,153,402 B2 | 4/2012 | Holliger et al. |
| 8,257,925 B2 | 9/2012 | Brown et al. |
| 8,278,071 B2 | 10/2012 | Brown et al. |
| 8,278,711 B2 | 10/2012 | Rao et al. |
| 8,318,434 B2 | 11/2012 | Cuppens |
| 8,337,778 B2 | 12/2012 | Stone et al. |
| 8,436,993 B2 | 5/2013 | Kaduchak et al. |
| 8,462,269 B2 | 6/2013 | Cheng et al. |
| 8,528,589 B2 | 9/2013 | Miller et al. |
| 8,535,889 B2 | 9/2013 | Larson et al. |
| 8,592,221 B2 | 11/2013 | Fraden et al. |
| 8,673,595 B2 | 3/2014 | Nakamura et al. |
| 8,715,934 B2 | 5/2014 | Diehl et al. |
| 8,765,485 B2 | 7/2014 | Link et al. |
| 8,772,046 B2 | 7/2014 | Fraden et al. |
| 8,871,444 B2 | 10/2014 | Griffiths et al. |

(56) References Cited

U.S. PATENT DOCUMENTS

| | | | |
|---|---|---|---|
| 9,029,083 B2 | 5/2015 | Griffiths et al. | |
| 9,029,085 B2 | 5/2015 | Agresti et al. | |
| 9,186,643 B2 | 11/2015 | Griffiths et al. | |
| 9,364,803 B2 | 6/2016 | Yurkovetsky et al. | |
| 9,448,172 B2 | 9/2016 | Griffiths et al. | |
| 9,562,897 B2 * | 2/2017 | Samuels et al. | C40B 40/00 |
| 9,839,890 B2 | 12/2017 | Griffiths et al. | |
| 9,857,202 B2 | 1/2018 | Seki | |
| 9,919,277 B2 | 3/2018 | Griffiths et al. | |
| 9,944,977 B2 | 4/2018 | Link et al. | |
| 10,151,698 B2 | 12/2018 | Griffiths et al. | |
| 10,357,772 B2 | 7/2019 | Fraden et al. | |
| 10,526,605 B2 | 1/2020 | Liu et al. | |
| 10,584,332 B2 | 3/2020 | Samuels et al. | |
| 10,596,541 B2 | 3/2020 | Weitz et al. | |
| 10,612,081 B2 | 4/2020 | Hutchison et al. | |
| 10,639,597 B2 | 5/2020 | Link et al. | |
| 10,639,598 B2 | 5/2020 | Griffiths et al. | |
| 10,675,626 B2 | 6/2020 | Fraden et al. | |
| 2001/0010338 A1 | 8/2001 | Ganan-Calvo | |
| 2001/0020011 A1 | 9/2001 | Mathiowitz et al. | |
| 2001/0023078 A1 | 9/2001 | Bawendi et al. | |
| 2001/0029983 A1 | 10/2001 | Unger et al. | |
| 2001/0034025 A1 | 10/2001 | Modlin et al. | |
| 2001/0034031 A1 | 10/2001 | Short et al. | |
| 2001/0041343 A1 | 11/2001 | Pankowsky | |
| 2001/0041344 A1 | 11/2001 | Sepetov et al. | |
| 2001/0041357 A1 | 11/2001 | Fouillet et al. | |
| 2001/0042793 A1 | 11/2001 | Ganan-Calvo | |
| 2001/0048900 A1 | 12/2001 | Bardell et al. | |
| 2001/0050881 A1 | 12/2001 | Depaoli et al. | |
| 2002/0004532 A1 | 1/2002 | Matathia et al. | |
| 2002/0005354 A1 | 1/2002 | Spence et al. | |
| 2002/0008028 A1 | 1/2002 | Jacobson et al. | |
| 2002/0012971 A1 | 1/2002 | Mehta | |
| 2002/0015997 A1 | 2/2002 | Lafferty | |
| 2002/0022038 A1 | 2/2002 | Biatry et al. | |
| 2002/0022261 A1 | 2/2002 | Anderson et al. | |
| 2002/0033422 A1 | 3/2002 | Ganan-Calvo | |
| 2002/0034737 A1 | 3/2002 | Drmanac | |
| 2002/0036018 A1 | 3/2002 | McNeely et al. | |
| 2002/0036139 A1 | 3/2002 | Becker et al. | |
| 2002/0041378 A1 | 4/2002 | Peltie et al. | |
| 2002/0058332 A1 | 5/2002 | Quake et al. | |
| 2002/0067800 A1 | 6/2002 | Newman et al. | |
| 2002/0085961 A1 | 7/2002 | Morin et al. | |
| 2002/0090720 A1 | 7/2002 | Mutz et al. | |
| 2002/0106667 A1 | 8/2002 | Yamamoto et al. | |
| 2002/0119459 A1 | 8/2002 | Griffiths | |
| 2002/0127591 A1 | 9/2002 | Wada et al. | |
| 2002/0143437 A1 | 10/2002 | Handique et al. | |
| 2002/0155080 A1 | 10/2002 | Glenn et al. | |
| 2002/0158027 A1 | 10/2002 | Moon et al. | |
| 2002/0164271 A1 | 11/2002 | Ho | |
| 2002/0164629 A1 | 11/2002 | Quake et al. | |
| 2002/0166582 A1 | 11/2002 | O'Connor et al. | |
| 2003/0008308 A1 | 1/2003 | Enzelberger et al. | |
| 2003/0012586 A1 | 1/2003 | Iwata et al. | |
| 2003/0015425 A1 | 1/2003 | Bohm et al. | |
| 2003/0017305 A1 | 1/2003 | Roitman et al. | |
| 2003/0017579 A1 | 1/2003 | Corn et al. | |
| 2003/0039169 A1 | 2/2003 | Ehrfeld et al. | |
| 2003/0059764 A1 | 3/2003 | Ravkin et al. | |
| 2003/0061687 A1 | 4/2003 | Hansen et al. | |
| 2003/0064414 A1 | 4/2003 | Benecky et al. | |
| 2003/0082795 A1 | 5/2003 | Shuler et al. | |
| 2003/0083276 A1 | 5/2003 | Li et al. | |
| 2003/0104372 A1 | 6/2003 | Ahmadian et al. | |
| 2003/0108900 A1 | 6/2003 | Oliphant et al. | |
| 2003/0124586 A1 | 7/2003 | Griffiths et al. | |
| 2003/0143599 A1 | 7/2003 | Makarov et al. | |
| 2003/0144260 A1 | 7/2003 | Gilon | |
| 2003/0148273 A1 | 8/2003 | Dong et al. | |
| 2003/0148544 A1 | 8/2003 | Nie et al. | |
| 2003/0181574 A1 | 9/2003 | Adam et al. | |
| 2003/0183525 A1 | 10/2003 | Elrod et al. | |
| 2003/0207295 A1 | 11/2003 | Gunderson et al. | |
| 2003/0219754 A1 | 11/2003 | Oleksy et al. | |
| 2003/0224509 A1 | 12/2003 | Moon et al. | |
| 2003/0229376 A1 | 12/2003 | Sandhu | |
| 2003/0230486 A1 | 12/2003 | Chien et al. | |
| 2003/0232356 A1 | 12/2003 | Dooley et al. | |
| 2004/0005582 A1 | 1/2004 | Shipwash | |
| 2004/0005594 A1 | 1/2004 | Holliger et al. | |
| 2004/0018525 A1 | 1/2004 | Wirtz et al. | |
| 2004/0027915 A1 | 2/2004 | Lowe et al. | |
| 2004/0031688 A1 | 2/2004 | Shenderov | |
| 2004/0037739 A1 | 2/2004 | McNeely et al. | |
| 2004/0037813 A1 | 2/2004 | Simpson et al. | |
| 2004/0041093 A1 | 3/2004 | Schultz et al. | |
| 2004/0050946 A1 | 3/2004 | Wang et al. | |
| 2004/0053247 A1 | 3/2004 | Cordon-Cardo et al. | |
| 2004/0057906 A1 | 3/2004 | Hsu et al. | |
| 2004/0058450 A1 | 3/2004 | Pamula et al. | |
| 2004/0068019 A1 | 4/2004 | Higuchi et al. | |
| 2004/0071781 A1 | 4/2004 | Chattopadhyay et al. | |
| 2004/0079881 A1 | 4/2004 | Fischer et al. | |
| 2004/0086892 A1 | 5/2004 | Crothers et al. | |
| 2004/0091923 A1 | 5/2004 | Reyes et al. | |
| 2004/0096515 A1 | 5/2004 | Bausch et al. | |
| 2004/0134854 A1 | 7/2004 | Higuchi et al. | |
| 2004/0136497 A1 | 7/2004 | Meldrum et al. | |
| 2004/0142329 A1 | 7/2004 | Erikson et al. | |
| 2004/0146921 A1 | 7/2004 | Eveleigh et al. | |
| 2004/0159633 A1 | 8/2004 | Whitesides et al. | |
| 2004/0180346 A1 | 9/2004 | Anderson et al. | |
| 2004/0181131 A1 | 9/2004 | Maynard et al. | |
| 2004/0181343 A1 | 9/2004 | Wigstrom et al. | |
| 2004/0182712 A1 | 9/2004 | Basol | |
| 2004/0185484 A1 | 9/2004 | Costa et al. | |
| 2004/0188254 A1 | 9/2004 | Spaid | |
| 2004/0209299 A1 | 10/2004 | Pinter et al. | |
| 2004/0224419 A1 | 11/2004 | Zheng et al. | |
| 2004/0229349 A1 | 11/2004 | Daridon | |
| 2004/0241693 A1 | 12/2004 | Ricoul et al. | |
| 2004/0253731 A1 | 12/2004 | Holliger et al. | |
| 2004/0258203 A1 | 12/2004 | Yamano et al. | |
| 2004/0259083 A1 | 12/2004 | Oshima | |
| 2005/0000970 A1 | 1/2005 | Kimbara et al. | |
| 2005/0003380 A1 | 1/2005 | Cohen et al. | |
| 2005/0008592 A1 | 1/2005 | Gardel et al. | |
| 2005/0019776 A1 | 1/2005 | Callow et al. | |
| 2005/0032238 A1 | 2/2005 | Karp et al. | |
| 2005/0032240 A1 | 2/2005 | Lee et al. | |
| 2005/0037392 A1 | 2/2005 | Griffiths et al. | |
| 2005/0037397 A1 | 2/2005 | Mirkin et al. | |
| 2005/0042639 A1 | 2/2005 | Knapp et al. | |
| 2005/0042648 A1 | 2/2005 | Griffiths et al. | |
| 2005/0048467 A1 | 3/2005 | Sastry et al. | |
| 2005/0064460 A1 | 3/2005 | Holliger et al. | |
| 2005/0069920 A1 | 3/2005 | Griffiths et al. | |
| 2005/0079501 A1 | 4/2005 | Koike et al. | |
| 2005/0079510 A1 | 4/2005 | Berka et al. | |
| 2005/0084923 A1 | 4/2005 | Mueller et al. | |
| 2005/0087122 A1 | 4/2005 | Ismagliov et al. | |
| 2005/0095611 A1 | 5/2005 | Chan et al. | |
| 2005/0100895 A1 | 5/2005 | Waldman et al. | |
| 2005/0103690 A1 | 5/2005 | Kawano et al. | |
| 2005/0123937 A1 | 6/2005 | Thorp et al. | |
| 2005/0129582 A1 | 6/2005 | Breidford et al. | |
| 2005/0130173 A1 | 6/2005 | Leamon et al. | |
| 2005/0152908 A1 | 7/2005 | Liew et al. | |
| 2005/0161669 A1 | 7/2005 | Jovanovich et al. | |
| 2005/0164239 A1 | 7/2005 | Griffiths et al. | |
| 2005/0169797 A1 | 8/2005 | Oshima | |
| 2005/0170373 A1 | 8/2005 | Monforte | |
| 2005/0170431 A1 | 8/2005 | Ibrahim et al. | |
| 2005/0172476 A1 | 8/2005 | Stone et al. | |
| 2005/0183995 A1 | 8/2005 | Deshpande et al. | |
| 2005/0202429 A1 | 9/2005 | Trau et al. | |
| 2005/0202489 A1 | 9/2005 | Cho et al. | |
| 2005/0207940 A1 | 9/2005 | Butler et al. | |
| 2005/0208495 A1 | 9/2005 | Joseph et al. | |
| 2005/0214173 A1 | 9/2005 | Facer et al. | |

(56) References Cited

U.S. PATENT DOCUMENTS

| | | |
|---|---|---|
| 2005/0221339 A1 | 10/2005 | Griffiths et al. |
| 2005/0221341 A1 | 10/2005 | Shimkets et al. |
| 2005/0226742 A1 | 10/2005 | Unger et al. |
| 2005/0227264 A1 | 10/2005 | Nobile et al. |
| 2005/0248066 A1 | 11/2005 | Esteban |
| 2005/0260566 A1 | 11/2005 | Fischer et al. |
| 2005/0272159 A1 | 12/2005 | Ismagilov et al. |
| 2005/0287572 A1 | 12/2005 | Mathies et al. |
| 2006/0003347 A1 | 1/2006 | Griffiths et al. |
| 2006/0003429 A1 | 1/2006 | Frost et al. |
| 2006/0003439 A1 | 1/2006 | Ismagilov et al. |
| 2006/0008824 A1 | 1/2006 | Ronaghi et al. |
| 2006/0035386 A1 | 2/2006 | Hattori et al. |
| 2006/0036348 A1 | 2/2006 | Handique et al. |
| 2006/0040197 A1 | 2/2006 | Kabai |
| 2006/0040297 A1 | 2/2006 | Leamon et al. |
| 2006/0046257 A1 | 3/2006 | Pollock et al. |
| 2006/0051329 A1 | 3/2006 | Lee et al. |
| 2006/0068398 A1 | 3/2006 | McMillan |
| 2006/0078475 A1 | 4/2006 | Tai et al. |
| 2006/0078888 A1 | 4/2006 | Griffiths et al. |
| 2006/0078893 A1 | 4/2006 | Griffiths et al. |
| 2006/0094119 A1 | 5/2006 | Ismagilov et al. |
| 2006/0100788 A1 | 5/2006 | Carrino et al. |
| 2006/0108012 A1 | 5/2006 | Barrow et al. |
| 2006/0110759 A1 | 5/2006 | Paris et al. |
| 2006/0115821 A1 | 6/2006 | Einstein et al. |
| 2006/0147909 A1 | 7/2006 | Rarbach et al. |
| 2006/0153924 A1 | 7/2006 | Griffiths et al. |
| 2006/0154298 A1 | 7/2006 | Griffiths et al. |
| 2006/0160762 A1 | 7/2006 | Zetter et al. |
| 2006/0163385 A1 | 7/2006 | Link et al. |
| 2006/0169800 A1 | 8/2006 | Rosell et al. |
| 2006/0177832 A1 | 8/2006 | Brenner |
| 2006/0195269 A1 | 8/2006 | Yeatman et al. |
| 2006/0223127 A1 | 10/2006 | Yip et al. |
| 2006/0234254 A1 | 10/2006 | An et al. |
| 2006/0234259 A1 | 10/2006 | Rubin et al. |
| 2006/0234264 A1 | 10/2006 | Hardenbol |
| 2006/0246431 A1 | 11/2006 | Balachandran |
| 2006/0252057 A1 | 11/2006 | Raponi et al. |
| 2006/0257893 A1 | 11/2006 | Takahashi et al. |
| 2006/0258841 A1 | 11/2006 | Michl et al. |
| 2006/0263888 A1 | 11/2006 | Fritz et al. |
| 2006/0269558 A1 | 11/2006 | Murphy et al. |
| 2006/0269934 A1 | 11/2006 | Woudenberg et al. |
| 2006/0269971 A1 | 11/2006 | Diamandis |
| 2006/0281089 A1 | 12/2006 | Gibson et al. |
| 2006/0281098 A1 | 12/2006 | Miao et al. |
| 2007/0003442 A1 | 1/2007 | Link et al. |
| 2007/0009914 A1 | 1/2007 | Wallace et al. |
| 2007/0020617 A1 | 1/2007 | Trnovsky et al. |
| 2007/0026439 A1 | 2/2007 | Faulstich et al. |
| 2007/0045117 A1 | 3/2007 | Pamula et al. |
| 2007/0048744 A1 | 3/2007 | Lapidus |
| 2007/0053896 A1 | 3/2007 | Ahmed et al. |
| 2007/0054119 A1 | 3/2007 | Garstecki et al. |
| 2007/0056853 A1 | 3/2007 | Aizenberg et al. |
| 2007/0065823 A1 | 3/2007 | Dressman et al. |
| 2007/0077572 A1 | 4/2007 | Tawfik et al. |
| 2007/0077579 A1 | 4/2007 | Griffiths et al. |
| 2007/0092914 A1 | 4/2007 | Griffiths et al. |
| 2007/0111303 A1 | 5/2007 | Inoue et al. |
| 2007/0120899 A1 | 5/2007 | Ohnishi et al. |
| 2007/0123430 A1 | 5/2007 | Pasquier et al. |
| 2007/0141593 A1 | 6/2007 | Lee et al. |
| 2007/0154889 A1 | 7/2007 | Wang |
| 2007/0166705 A1 | 7/2007 | Milton et al. |
| 2007/0172873 A1 | 7/2007 | Brenner et al. |
| 2007/0184439 A1 | 8/2007 | Guilford et al. |
| 2007/0184489 A1 | 8/2007 | Griffiths et al. |
| 2007/0195127 A1 | 8/2007 | Ahn et al. |
| 2007/0202525 A1 | 8/2007 | Quake et al. |
| 2007/0213410 A1 | 9/2007 | Hastwell et al. |
| 2007/0241068 A1 | 10/2007 | Pamula et al. |
| 2007/0242105 A1 | 10/2007 | Srinivasan et al. |
| 2007/0243634 A1 | 10/2007 | Pamula et al. |
| 2007/0259351 A1 | 11/2007 | Chinitz et al. |
| 2007/0259368 A1 | 11/2007 | An et al. |
| 2007/0259374 A1 | 11/2007 | Griffiths et al. |
| 2007/0275415 A1 | 11/2007 | Srinivasan et al. |
| 2007/0292869 A1 | 12/2007 | Becker et al. |
| 2008/0003142 A1 | 1/2008 | Link et al. |
| 2008/0003571 A1 | 1/2008 | McKernan et al. |
| 2008/0004436 A1 | 1/2008 | Tawfik et al. |
| 2008/0009005 A1 | 1/2008 | Kruk |
| 2008/0014589 A1 | 1/2008 | Link et al. |
| 2008/0014590 A1 | 1/2008 | Dahary et al. |
| 2008/0020940 A1 | 1/2008 | Stedronsky et al. |
| 2008/0021330 A1 | 1/2008 | Hwang et al. |
| 2008/0023330 A1 | 1/2008 | Viovy et al. |
| 2008/0032413 A1 | 2/2008 | Kim et al. |
| 2008/0038754 A1 | 2/2008 | Farias-Eisner et al. |
| 2008/0044828 A1 | 2/2008 | Kwok |
| 2008/0050378 A1 | 2/2008 | Nakamura et al. |
| 2008/0050723 A1 | 2/2008 | Belacel et al. |
| 2008/0053205 A1 | 3/2008 | Pollack et al. |
| 2008/0057514 A1 | 3/2008 | Goldenring |
| 2008/0058432 A1 | 3/2008 | Wang et al. |
| 2008/0063227 A1 | 3/2008 | Rohrseitz |
| 2008/0064047 A1 | 3/2008 | Zetter et al. |
| 2008/0081330 A1 | 4/2008 | Kahvejian |
| 2008/0081333 A1 | 4/2008 | Mori et al. |
| 2008/0092973 A1 | 4/2008 | Lai |
| 2008/0113340 A1 | 5/2008 | Schlegel |
| 2008/0118462 A1 | 5/2008 | Alani et al. |
| 2008/0124726 A1 | 5/2008 | Monforte |
| 2008/0138806 A1 | 6/2008 | Chow et al. |
| 2008/0166772 A1 | 7/2008 | Hollinger et al. |
| 2008/0166793 A1 | 7/2008 | Beer et al. |
| 2008/0171078 A1 | 7/2008 | Gray |
| 2008/0176211 A1 | 7/2008 | Spence et al. |
| 2008/0176236 A1 | 7/2008 | Tsao et al. |
| 2008/0181850 A1 | 7/2008 | Thaxton et al. |
| 2008/0206756 A1 | 8/2008 | Lee et al. |
| 2008/0216563 A1 | 9/2008 | Reed et al. |
| 2008/0220986 A1 | 9/2008 | Gormley et al. |
| 2008/0222741 A1 | 9/2008 | Chinnaiyan |
| 2008/0234138 A1 | 9/2008 | Shaughnessy et al. |
| 2008/0234139 A1 | 9/2008 | Shaughnessy et al. |
| 2008/0241830 A1 | 10/2008 | Vogelstein et al. |
| 2008/0261295 A1 | 10/2008 | Butler et al. |
| 2008/0268473 A1 | 10/2008 | Moses et al. |
| 2008/0269157 A1 | 10/2008 | Srivastava et al. |
| 2008/0274513 A1 | 11/2008 | Shenderov et al. |
| 2008/0274908 A1 | 11/2008 | Chang |
| 2008/0280285 A1 | 11/2008 | Chen et al. |
| 2008/0280302 A1 | 11/2008 | Kebebew |
| 2008/0286199 A1 | 11/2008 | Livingston et al. |
| 2008/0286801 A1 | 11/2008 | Arjol et al. |
| 2008/0286811 A1 | 11/2008 | Moses et al. |
| 2008/0293578 A1 | 11/2008 | Shaugnessy et al. |
| 2008/0299565 A1 | 12/2008 | Schneider et al. |
| 2008/0311570 A1 | 12/2008 | Lai |
| 2008/0311604 A1 | 12/2008 | Elting et al. |
| 2009/0004687 A1 | 1/2009 | Mansfield et al. |
| 2009/0005254 A1 | 1/2009 | Griffiths et al. |
| 2009/0009855 A1 | 1/2009 | Nakatsuka et al. |
| 2009/0012187 A1 | 1/2009 | Chu et al. |
| 2009/0017463 A1 | 1/2009 | Bhowmick |
| 2009/0021728 A1 | 1/2009 | Heinz et al. |
| 2009/0023137 A1 | 1/2009 | Van Der Zee et al. |
| 2009/0026082 A1 | 1/2009 | Rothberg et al. |
| 2009/0029372 A1 | 1/2009 | Wewer |
| 2009/0042737 A1 | 2/2009 | Katz et al. |
| 2009/0053700 A1 | 2/2009 | Griffiths et al. |
| 2009/0053732 A1 | 2/2009 | Vermesh et al. |
| 2009/0060797 A1 | 3/2009 | Mathies et al. |
| 2009/0062144 A1 | 3/2009 | Guo |
| 2009/0068170 A1 | 3/2009 | Weitz et al. |
| 2009/0069194 A1 | 3/2009 | Ramakrishnan |
| 2009/0075265 A1 | 3/2009 | Budiman et al. |
| 2009/0075307 A1 | 3/2009 | Fischer et al. |
| 2009/0075311 A1 | 3/2009 | Karl |

(56) References Cited

U.S. PATENT DOCUMENTS

| | | |
|---|---|---|
| 2009/0081237 A1 | 3/2009 | D'Andrea et al. |
| 2009/0081685 A1 | 3/2009 | Beyer et al. |
| 2009/0087849 A1 | 4/2009 | Malinowski et al. |
| 2009/0092973 A1 | 4/2009 | Erlander et al. |
| 2009/0098542 A1 | 4/2009 | Budiman et al. |
| 2009/0098543 A1 | 4/2009 | Budiman et al. |
| 2009/0098555 A1 | 4/2009 | Roth et al. |
| 2009/0105959 A1 | 4/2009 | Braverman et al. |
| 2009/0118128 A1 | 5/2009 | Liu et al. |
| 2009/0124569 A1 | 5/2009 | Bergan et al. |
| 2009/0127454 A1 | 5/2009 | Ritchie et al. |
| 2009/0127589 A1 | 5/2009 | Rothberg et al. |
| 2009/0131353 A1 | 5/2009 | Insel et al. |
| 2009/0131543 A1 | 5/2009 | Weitz et al. |
| 2009/0134027 A1 | 5/2009 | Jary |
| 2009/0191565 A1 | 7/2009 | Lapidus et al. |
| 2009/0197248 A1 | 8/2009 | Griffiths et al. |
| 2009/0197772 A1 | 8/2009 | Griffiths et al. |
| 2009/0215633 A1 | 8/2009 | Van Eijk et al. |
| 2009/0226971 A1 | 9/2009 | Beer et al. |
| 2009/0226972 A1 | 9/2009 | Beer et al. |
| 2009/0233802 A1 | 9/2009 | Bignell et al. |
| 2009/0246788 A1 | 10/2009 | Albert et al. |
| 2009/0317798 A1 | 12/2009 | Heid et al. |
| 2009/0325217 A1 | 12/2009 | Luscher |
| 2009/0325236 A1 | 12/2009 | Griffiths et al. |
| 2010/0003687 A1 | 1/2010 | Simen et al. |
| 2010/0009353 A1 | 1/2010 | Barnes et al. |
| 2010/0015617 A1 | 1/2010 | Toyama |
| 2010/0021984 A1 | 1/2010 | Edd et al. |
| 2010/0022414 A1 | 1/2010 | Link et al. |
| 2010/0035252 A1 | 2/2010 | Rothberg et al. |
| 2010/0075436 A1 | 3/2010 | Urdea et al. |
| 2010/0105112 A1 | 4/2010 | Holtze et al. |
| 2010/0111768 A1 | 5/2010 | Banerjee et al. |
| 2010/0124759 A1 | 5/2010 | Wang et al. |
| 2010/0130369 A1 | 5/2010 | Shenderov et al. |
| 2010/0136544 A1 | 6/2010 | Agresti et al. |
| 2010/0137143 A1 | 6/2010 | Rothberg et al. |
| 2010/0137163 A1 | 6/2010 | Link et al. |
| 2010/0159592 A1 | 6/2010 | Holliger et al. |
| 2010/0172803 A1 | 7/2010 | Stone et al. |
| 2010/0173293 A1 | 7/2010 | Woudenberg et al. |
| 2010/0173394 A1 | 7/2010 | Colston, Jr. et al. |
| 2010/0188073 A1 | 7/2010 | Rothberg et al. |
| 2010/0197507 A1 | 8/2010 | Rothberg et al. |
| 2010/0210479 A1 | 8/2010 | Griffiths et al. |
| 2010/0213628 A1 | 8/2010 | Bausch et al. |
| 2010/0233026 A1 | 9/2010 | Ismagliov et al. |
| 2010/0240101 A1 | 9/2010 | Lieberman et al. |
| 2010/0273173 A1 | 10/2010 | Hirai et al. |
| 2010/0282617 A1 | 11/2010 | Rothberg et al. |
| 2010/0285975 A1 | 11/2010 | Mathies et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0000560 A1 | 1/2011 | Miller et al. |
| 2011/0024455 A1 | 2/2011 | Bethuy et al. |
| 2011/0033854 A1 | 2/2011 | Drmanac et al. |
| 2011/0045462 A1 | 2/2011 | Fu et al. |
| 2011/0053151 A1 | 3/2011 | Hansen et al. |
| 2011/0053798 A1 | 3/2011 | Hindson et al. |
| 2011/0142734 A1 | 6/2011 | Ismagliov et al. |
| 2011/0151444 A1 | 6/2011 | Albers et al. |
| 2011/0174622 A1 | 7/2011 | Ismagliov et al. |
| 2011/0176966 A1 | 7/2011 | Ismagliov et al. |
| 2011/0177494 A1 | 7/2011 | Ismagliov et al. |
| 2011/0177586 A1 | 7/2011 | Ismagliov et al. |
| 2011/0177609 A1 | 7/2011 | Ismagliov et al. |
| 2011/0188717 A1 | 8/2011 | Baudry et al. |
| 2011/0190146 A1 | 8/2011 | Boehm et al. |
| 2011/0218123 A1 | 9/2011 | Weitz et al. |
| 2011/0223314 A1 | 9/2011 | Zhang et al. |
| 2011/0244455 A1 | 10/2011 | Larson et al. |
| 2011/0250597 A1 | 10/2011 | Larson et al. |
| 2011/0257031 A1 | 10/2011 | Bodeau et al. |
| 2011/0267457 A1 | 11/2011 | Weitz et al. |
| 2011/0275063 A1 | 11/2011 | Weitz et al. |
| 2011/0311978 A1 | 12/2011 | Makarewicz, Jr. et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0021930 A1 | 1/2012 | Schoen et al. |
| 2012/0122714 A1 | 5/2012 | Samuels et al. |
| 2012/0167142 A1 | 6/2012 | Hey |
| 2012/0190032 A1 | 7/2012 | Ness et al. |
| 2012/0220494 A1* | 8/2012 | Samuels et al. ........ C40B 50/08 506/26 |
| 2012/0244043 A1 | 9/2012 | Leblanc et al. |
| 2012/0258516 A1 | 10/2012 | Schultz et al. |
| 2012/0288857 A1 | 11/2012 | Livak |
| 2012/0302448 A1 | 11/2012 | Hutchison et al. |
| 2013/0099018 A1 | 4/2013 | Miller et al. |
| 2013/0109577 A1 | 5/2013 | Korlach et al. |
| 2013/0143745 A1 | 6/2013 | Christen et al. |
| 2013/0157872 A1 | 6/2013 | Griffiths et al. |
| 2013/0178368 A1 | 7/2013 | Griffiths et al. |
| 2013/0178378 A1 | 7/2013 | Hatch et al. |
| 2013/0217601 A1 | 8/2013 | Griffiths et al. |
| 2013/0224751 A1 | 8/2013 | Olson et al. |
| 2013/0274117 A1 | 10/2013 | Church et al. |
| 2013/0295567 A1 | 11/2013 | Link et al. |
| 2013/0295568 A1 | 11/2013 | Link |
| 2013/0296535 A1 | 11/2013 | Church et al. |
| 2014/0065631 A1 | 3/2014 | Froehlich et al. |
| 2014/0256568 A1 | 9/2014 | Link |
| 2014/0256585 A1 | 9/2014 | McCoy |
| 2014/0274786 A1 | 9/2014 | McCoy et al. |
| 2014/0323317 A1 | 10/2014 | Link et al. |
| 2014/0329239 A1 | 11/2014 | Larson et al. |
| 2015/0018236 A1 | 1/2015 | Green et al. |
| 2015/0126400 A1 | 5/2015 | Watson et al. |
| 2015/0184256 A1 | 7/2015 | Samuels et al. |
| 2015/0197790 A1 | 7/2015 | Tzonev |
| 2015/0336072 A1 | 11/2015 | Weitz et al. |
| 2016/0289670 A1 | 10/2016 | Samuels et al. |
| 2016/0304954 A1 | 10/2016 | Lin et al. |
| 2017/0304785 A1 | 10/2017 | Link et al. |
| 2018/0057863 A1 | 3/2018 | Larson et al. |
| 2018/0223348 A1 | 8/2018 | Link et al. |
| 2018/0272296 A1 | 9/2018 | Link et al. |
| 2018/0272299 A1 | 9/2018 | Griffiths et al. |
| 2018/0353913 A1 | 12/2018 | Link et al. |
| 2018/0355350 A1 | 12/2018 | Link et al. |
| 2018/0361346 A1 | 12/2018 | Griffiths et al. |
| 2018/0363050 A1 | 12/2018 | Hutchison et al. |
| 2019/0024261 A1 | 1/2019 | Griffiths et al. |
| 2019/0107489 A1 | 4/2019 | Griffiths et al. |
| 2019/0134581 A1 | 5/2019 | Yurkovetsky et al. |
| 2019/0316119 A1 | 10/2019 | Samuels et al. |

FOREIGN PATENT DOCUMENTS

| | | | |
|---|---|---|---|
| AT | 155711 | T | 8/1997 |
| AT | 167816 | T | 7/1998 |
| AU | 4032078 | A | 4/1980 |
| AU | 6415380 | A | 5/1981 |
| AU | 1045983 | A | 6/1984 |
| AU | 2177292 | A | 1/1993 |
| AU | 4222393 | A | 11/1993 |
| AU | 4222593 | A | 11/1993 |
| AU | 4222693 | A | 11/1993 |
| AU | 4222793 | A | 11/1993 |
| AU | 4223593 | A | 11/1993 |
| AU | 677197 | B2 | 4/1997 |
| AU | 677781 | B2 | 5/1997 |
| AU | 680195 | B2 | 7/1997 |
| AU | 2935197 | A | 1/1998 |
| AU | 3499097 | A | 1/1998 |
| AU | 3501297 | A | 1/1998 |
| AU | 1276099 | A | 6/1999 |
| AU | 4955799 | A | 12/1999 |

(56) References Cited

FOREIGN PATENT DOCUMENTS

| | | |
|---|---|---|
| AU | 3961100 A | 10/2000 |
| AU | 4910300 A | 11/2000 |
| AU | 747464 B2 | 5/2002 |
| AU | 768399 B2 | 12/2003 |
| AU | 2004225691 B2 | 6/2010 |
| AU | 2010224352 A1 | 10/2010 |
| CA | 1093344 A1 | 1/1981 |
| CA | 2258481 A1 | 1/1998 |
| CA | 2520548 A1 | 10/2004 |
| CH | 563 087 A5 | 6/1975 |
| CH | 563807 A5 | 7/1975 |
| DE | 2100685 A1 | 7/1972 |
| DE | 3042915 A1 | 9/1981 |
| DE | 43 08 839 C2 | 4/1997 |
| DE | 69126763 T2 | 2/1998 |
| DE | 199 61 257 A1 | 7/2001 |
| DE | 100 15 109 A1 | 10/2001 |
| DE | 100 41 823 A1 | 3/2002 |
| EP | 0047130 B1 | 2/1985 |
| EP | 0402995 A2 | 12/1990 |
| EP | 0249007 A3 | 3/1991 |
| EP | 0418635 A1 | 3/1991 |
| EP | 0476178 A1 | 3/1992 |
| EP | 0618001 | 10/1994 |
| EP | 0637996 A1 | 2/1995 |
| EP | 0637997 A1 | 2/1995 |
| EP | 0718038 A2 | 6/1996 |
| EP | 0540281 B1 | 7/1996 |
| EP | 0528580 B1 | 12/1996 |
| EP | 0486351 B1 | 7/1997 |
| EP | 0895120 | 2/1999 |
| EP | 1362634 A1 | 11/2003 |
| EP | 04782399.2 | 5/2006 |
| EP | 1741482 | 1/2007 |
| EP | 2017910 A1 | 1/2009 |
| EP | 2127736 | 12/2009 |
| EP | 13165665.4 | 11/2013 |
| EP | 13165667.0 | 11/2013 |
| EP | 2363205 A3 | 6/2014 |
| ES | 2 095 413 T3 | 2/1997 |
| FR | 2 404 834 A1 | 4/1979 |
| FR | 2 451 579 A1 | 10/1980 |
| FR | 2 469 714 A1 | 5/1981 |
| FR | 2 470 385 A1 | 5/1981 |
| FR | 2 650 657 A1 | 2/1991 |
| FR | 2 669 028 A1 | 5/1992 |
| FR | 2 703 263 A1 | 10/1994 |
| GB | 1148543 | 4/1969 |
| GB | 1 446 998 | 8/1976 |
| GB | 2 005 224 | 4/1979 |
| GB | 2 047 880 | 12/1980 |
| GB | 2 062 225 | 5/1981 |
| GB | 2 064 114 | 6/1981 |
| GB | 2097692 A | 11/1982 |
| GB | 2 210 532 | 6/1989 |
| IE | 922432 A1 | 2/1993 |
| JP | S5372016 A | 6/1978 |
| JP | S5455495 A | 5/1979 |
| JP | 55125472 | 9/1980 |
| JP | S5636053 A | 4/1981 |
| JP | 56-124052 | 9/1981 |
| JP | 59-49832 A | 3/1984 |
| JP | 59-102163 | 6/1984 |
| JP | H0665609 A | 3/1994 |
| JP | 6-265447 A | 9/1994 |
| JP | 7-489 A | 1/1995 |
| JP | 8-153669 | 6/1996 |
| JP | 10-217477 | 8/1998 |
| JP | 3-232525 | 10/1998 |
| JP | 2000-271475 | 10/2000 |
| JP | 2001-301154 A | 10/2001 |
| JP | 2001-517353 A | 10/2001 |
| JP | 2002-085961 A | 3/2002 |
| JP | 2003-501257 A | 1/2003 |
| JP | 2003-502656 A | 1/2003 |
| JP | 2003-222633 A | 8/2003 |
| JP | 2005-037346 A | 2/2005 |
| JP | 2009-265751 A | 11/2009 |
| JP | 2010-198393 A | 9/2010 |
| JP | 2012-204765 A | 10/2012 |
| JP | 2016063824 A | 4/2016 |
| NZ | 264353 A | 5/1996 |
| WO | 84/02000 | 5/1984 |
| WO | 91/05058 A1 | 4/1991 |
| WO | 91/07772 | 5/1991 |
| WO | 91/16966 A1 | 11/1991 |
| WO | 92/03734 | 3/1992 |
| WO | 92/21746 | 12/1992 |
| WO | 93/03151 | 2/1993 |
| WO | 93/08278 | 4/1993 |
| WO | 93/22053 | 11/1993 |
| WO | 93/22054 | 11/1993 |
| WO | 93/22055 | 11/1993 |
| WO | 93/22058 | 11/1993 |
| WO | 93/22421 | 11/1993 |
| WO | 94/16332 | 7/1994 |
| WO | 94/23738 | 10/1994 |
| WO | 94/24314 | 10/1994 |
| WO | 94/26766 | 11/1994 |
| WO | 98/00705 | 1/1995 |
| WO | 95/11922 | 5/1995 |
| WO | 95/19922 | 7/1995 |
| WO | 95/24929 | 9/1995 |
| WO | 95/33447 | 12/1995 |
| WO | 96/34112 | 10/1996 |
| WO | 96/38730 | 12/1996 |
| WO | 96/40062 | 12/1996 |
| WO | 96/40723 | 12/1996 |
| WO | 97/00125 | 1/1997 |
| WO | 97/00442 | 1/1997 |
| WO | 97/04297 | 2/1997 |
| WO | 97/04748 | 2/1997 |
| WO | 97/23140 | 7/1997 |
| WO | 97/28556 | 8/1997 |
| WO | 97/38318 A1 | 10/1997 |
| WO | 97/39814 | 10/1997 |
| WO | 97/40141 | 10/1997 |
| WO | 97/45644 | 12/1997 |
| WO | 97/47763 A1 | 12/1997 |
| WO | 98/00231 | 1/1998 |
| WO | 98/02237 | 1/1998 |
| WO | 98/10267 | 3/1998 |
| WO | 98/13502 | 4/1998 |
| WO | 98/23733 | 6/1998 |
| WO | 98/31700 | 7/1998 |
| WO | 98/33001 | 7/1998 |
| WO | 98/34120 | 8/1998 |
| WO | 98/37186 | 8/1998 |
| WO | 98/41869 | 9/1998 |
| WO | 98/52691 | 11/1998 |
| WO | 98/58085 | 12/1998 |
| WO | 99/02671 | 1/1999 |
| WO | 99/22858 | 5/1999 |
| WO | 99/28020 | 6/1999 |
| WO | 99/31019 | 6/1999 |
| WO | 99/42539 A1 | 8/1999 |
| WO | 99/54730 | 10/1999 |
| WO | 99/61888 | 12/1999 |
| WO | 00/04139 A1 | 1/2000 |
| WO | 00/47322 | 2/2000 |
| WO | 00/52455 | 2/2000 |
| WO | 00/40712 | 6/2000 |
| WO | 00/54735 | 9/2000 |
| WO | 00/61275 | 10/2000 |
| WO | 00/70080 | 11/2000 |
| WO | 00/76673 | 12/2000 |
| WO | 00/078455 A1 | 12/2000 |
| WO | 01/12327 | 2/2001 |
| WO | 01/14589 | 3/2001 |
| WO | 01/18244 | 3/2001 |
| WO | 01/64332 | 9/2001 |
| WO | 01/68257 | 9/2001 |
| WO | 01/69289 | 9/2001 |
| WO | 01/72431 | 10/2001 |

(56) References Cited

FOREIGN PATENT DOCUMENTS

| | | |
|---|---|---|
| WO | 01/80283 | 10/2001 |
| WO | 01/089787 A2 | 11/2001 |
| WO | 01/89788 A2 | 11/2001 |
| WO | 01/94635 A2 | 12/2001 |
| WO | 02/16017 | 2/2002 |
| WO | 02/18949 | 3/2002 |
| WO | 02/22869 | 3/2002 |
| WO | 02/23163 A1 | 3/2002 |
| WO | 02/31203 | 4/2002 |
| WO | 2002/036815 A2 | 5/2002 |
| WO | 02/47665 | 8/2002 |
| WO | 02/060275 | 8/2002 |
| WO | 02/060591 A1 | 8/2002 |
| WO | 02/068104 A1 | 9/2002 |
| WO | 02/078845 | 10/2002 |
| WO | 02/103011 | 12/2002 |
| WO | 02/103363 | 12/2002 |
| WO | 03/011443 | 2/2003 |
| WO | 03/026798 A1 | 4/2003 |
| WO | 03/037302 | 5/2003 |
| WO | 03/044187 | 5/2003 |
| WO | 03/078659 | 9/2003 |
| WO | 2003/003015 | 10/2003 |
| WO | 03/099843 | 12/2003 |
| WO | 2004/002627 | 1/2004 |
| WO | 2004/018497 A2 | 3/2004 |
| WO | 2004/024917 | 3/2004 |
| WO | 2004/037374 A2 | 5/2004 |
| WO | 2004/038363 | 5/2004 |
| WO | 04/071638 A2 | 8/2004 |
| WO | 2004/069849 A2 | 8/2004 |
| WO | 2004/074504 | 9/2004 |
| WO | 2004/083443 | 9/2004 |
| WO | 2004/087308 | 10/2004 |
| WO | 2004/088314 | 10/2004 |
| WO | 2004/091763 | 10/2004 |
| WO | 2004/102204 | 11/2004 |
| WO | 2004/103565 | 12/2004 |
| WO | 2005/000970 | 1/2005 |
| WO | 2005/002730 | 1/2005 |
| WO | 2005/003375 A2 | 1/2005 |
| WO | 2005/11867 A2 | 2/2005 |
| WO | 05/021151 | 3/2005 |
| WO | 2005/023427 A1 | 3/2005 |
| WO | 2005/041884 A2 | 5/2005 |
| WO | 05/049787 A2 | 6/2005 |
| WO | 2005/103106 | 11/2005 |
| WO | 2005/118138 | 12/2005 |
| WO | 2005/118867 A2 | 12/2005 |
| WO | 2006/002641 | 1/2006 |
| WO | 2006/009657 | 1/2006 |
| WO | 2006/027757 | 3/2006 |
| WO | 2006/038035 A2 | 4/2006 |
| WO | 2006/040551 | 4/2006 |
| WO | 2006/040554 | 4/2006 |
| WO | 2006/078841 | 7/2006 |
| WO | 2006/096571 | 9/2006 |
| WO | 2006/101851 | 9/2006 |
| WO | 2007/012638 A1 | 2/2007 |
| WO | 2007/021343 | 2/2007 |
| WO | 2007/030501 | 3/2007 |
| WO | 2007/081385 | 7/2007 |
| WO | 2007/081387 | 7/2007 |
| WO | 2007/089541 | 8/2007 |
| WO | 2007/114794 A1 | 10/2007 |
| WO | 2007/123744 A2 | 11/2007 |
| WO | 2007/133710 | 11/2007 |
| WO | 2007/138178 | 12/2007 |
| WO | 2007/140015 A2 | 12/2007 |
| WO | 2008/021123 | 2/2008 |
| WO | 2008/063227 | 5/2008 |
| WO | 2008/097559 | 8/2008 |
| WO | 2008/115626 A2 | 9/2008 |
| WO | 2008/121342 | 10/2008 |
| WO | 2008/130623 | 10/2008 |
| WO | 2007/092473 | 11/2008 |
| WO | 2008/134153 A1 | 11/2008 |
| WO | 2009/015296 A1 | 1/2009 |
| WO | 2009/029229 | 3/2009 |
| WO | 2009/049889 A1 | 4/2009 |
| WO | 2009/059430 A1 | 5/2009 |
| WO | 2009/085929 A1 | 7/2009 |
| WO | 2009/137415 A2 | 11/2009 |
| WO | 2009/137606 A1 | 11/2009 |
| WO | 2010/009365 A1 | 1/2010 |
| WO | 2010/056728 A1 | 5/2010 |
| WO | 2010/040006 | 8/2010 |
| WO | 2010/115154 A1 | 10/2010 |
| WO | 2010/151776 | 12/2010 |
| WO | 2011/042564 | 4/2011 |
| WO | 2011/079176 | 6/2011 |
| WO | 2011/100604 A2 | 8/2011 |
| WO | 2012/022976 A1 | 2/2012 |
| WO | 2012/045012 A2 | 4/2012 |
| WO | 2012/048341 A1 | 4/2012 |
| WO | 2012/083225 A2 | 6/2012 |
| WO | 2012/167142 A2 | 12/2012 |
| WO | 2013/14356 A2 | 1/2013 |
| WO | 2013/165748 A1 | 11/2013 |
| WO | 2014/026031 A1 | 2/2014 |
| WO | 2014/065756 A1 | 5/2014 |
| WO | 2014/165559 A2 | 10/2014 |
| WO | 2014/204939 A2 | 12/2014 |
| WO | 2015/013681 A1 | 1/2015 |
| WO | 2015/200893 A2 | 12/2015 |
| WO | 2017/117358 A1 | 7/2017 |

OTHER PUBLICATIONS

Peng, 1998, Controlled Production of Emulsions Using a Crossflow Membrane, Particle & Particle Systems Characterization 15:21-25.
Pepe, 2004, Limitations of the odds ratio in gauging the performance of a diagnostic, prognostic, or screening marker, American Journal of Epidemiology 159(9):882-890.
Perelson, 1979, Theorectical studies of clonal selection: minimal antibody repertoire size and relaibility of self-non-self discrimination. J Theor Biol 81(4):645-70.
Perez-Gilabert, 1992, Application of active-phase plot to the kinetic analysis of lipoxygenase in reverse micelles, Biochemistry J. 288:1011-1015.
Petrounia, 2000, Designed evolution of enzymatic properties, Curr Opin Biotechnol, 11:325-330.
Pirrung, 1996, A General Method for the Spatially Defined Immobilization of Biomolecules on Glass Surfaces Using Caged' Biotin, Bioconjug Chem 7: 317-321.
Ploem, 1993, in Fluorescent and Luminescent Probes for Biological Activity Mason, T. G. Ed., Academic Press, Landon, pp. 1-11.
Pluckthun, 2000, In vitro selection and evolution of proteins, Adv Protein Chem, 55: 367-403.
Pollack, 1986, Selective chemical catalysis by an antibody, Science 234(4783):1570-3.
Pollack, 2002, Electrowetting-based actuation of droplets for integrated microfluidics, Lab Chip 2:96-101.
Pons, 2009, Synthesis of Near-Infrared-Emitting, Water-Soluble CdTeSe/CdZnS Core/Shell Quantum Dots, Chemistry of Materials 21(8):1418-1424.
Posner, 1996, Engineering specificity for folate into dihydrofolate reductase from *Escherichia coli*, Biochemistry, 35:1653-63.
Priest, 2006, Generation of Monodisperse Gel Emulsions in a Microfluidic Device, Applied Physics Letters, 88:024106, 3 pages.
Qi, 1998, Acid Beta-Glucosidase: Intrinsic Fluorescence and Conformational Changes Induced by Phospholipids and Saposin C, Biochem., 37(33): 11544-11554.
Raghuraman, 1994, Emulston Liquid Membranes for Wastewater Treatment: Equillibrium Models for Some Typical Metal-Extractant Systems,Environ. Sci. Technol 28:1090-1098.
Ralhan, 2008, Discovery and Verification of Head-and-neck Cancer Biomarkers by Differential Protein Expression Analysis Using iTRAQ Labeling, Multidimensional Liquid Chromatography, and Tandem Mass Spectrometry, Mol Cell Proteomics 7(6):1162-1173.

(56) References Cited

OTHER PUBLICATIONS

Ramanan, 2016, Algae-bacteria interactions, Biotech ADv 34:14-29.
Ramsey, 1999, The burgeoning power of the shrinking laboratory, Nat Biotechnol 17(11):1061-2.
Ramstrom, 2002, Drug discovery by dynamic combinatorial libraries, Nat Rev Drug Discov 1:26-36.
Rasmussen, 2013, Comparison of HDAC inhibitors in clinical development, Human Vacc Immunother 9(5):993-1001.
Raushel, 2000, Phosphotriesterase: an enzyme in search of its natural substrate, Adv Enzymol Relat Areas Mol Biol, 74: 51-93.
Rech, 1990, Introduction of a yeast artificial chromosome vector into *Sarrachomyeces cervesia* by electroporation, Nucleic Acids Res 18:1313.
Reyes, 2002, Micro Total Analysis Systems. 1. Introduction, Theory and Technology, Anal Chem 74(12):2623-2636.
Riechmann, 1988, Reshaping human antibodies for therapy, Nature, 332:323-327.
Riess, 2002, Fluorous micro- and nanophases with a biomedical perspective, Tetrahedron 58(20):4113-4131.
Roach, 2005, Controlling nonspecific protein adsorption in a plug-based microfluidic system by controlling inteifacial chemistry using fluorous-phase surfactants, Anal. Chem. 77:785-796.
Roberts, 1969, Termination factor for RNA synthesis, Nature, 224:1168-74.
Roberts, 1975, Simian virus 40 DNA directs synthesis of authentic viral polypeptides in a linked transcription-translation cell-free system 72(5):1922-1926.
Roberts, 1997, RNA-peptide fusion for the in vitro selection of peptides and proteins, PNAS 94:12297-302.
Roberts, 1999, In vitro selection of nucleic acids and proteins: What are we learning, Curr Opin Struct Biol 9(4): 521-9.
Roberts, 1999, Totally in vitro protein selection using mRNA-protein fusions and ribosome display. Curr Opin Chem Biol 3(3), 268-73.
Roche, 2011, 454 Sequencing System Guidelines for Amplicon Experimental Design, 50 pages.
Rodriguez-Antona, 2000, Quantitative RT-PCR measurement of human cytochrome P-450s: application to drug induction studies. Arch. Biochem. Biophys., 376:109-116.
Rolland, 1985, Fluorescence Polarization Assay by Flow Cytometry, J. Immunol. Meth., 76(1): 1-10.
Rosenberg, 1975, Inhibition of Human Factor IX by Human Antithrombin, J Biol Chem, 250: 4755-64.
Rosenberry, 1975, Acetylcholinesterase, Adv Enzymol Relat Areas Mol Biol, 43: 103-218.
Rotman, 1961, Measurement of activities of single molecules of beta-galactosidase, PNAS, 47:1981-91.
Rouzioux, 2013, How to best measure HIV reservoirs, Curr Op HIV AIDS 8(3):170-175.
Russon et al., Single-nucleotide polymorphism analysis by allele-specific extension of fluorescently labeled nucleotides in a microfluidic flow-through device, Electrophoresis, 24:158-61 (2003).
Saarela, 2006, Re-usable multi-inlet PDMS fluidic connector, Sensors Actuators B 114(1):552-57.
Sadtler, 1996, Achieving stable, reverse water-in-fluorocarbon emulsions, Angew Chem Int Ed 35(17):1976-1978.
Sadtler, 1999, Reverse water-In-fluorocarbon emulsions as a drug delivery system: an in vitro study, Colloids & Surfaces A: Phys Eng Asp 147:309-315.
Saiki, 1988, Primer directed enzymatic amplification of DNA with a thermostable DNA polymerase, Science 239(4839):487-91.
Sakamoto, 2005, Rapid and simple quantification of bacterial cells by using a microfluidic device, Appl Env Microb 71:2.
Sano, 1992, Immuno-PCR: very sensitive antigen-detection by means of sepcific Ab-DNA conjugates, Science 258(5079):120-122.
Santalucia, 1998, A unified view of polymer, dumbbell, and oligonucleotide DNA nearest-neighbor thermodynamics, PNAS 95(4):1460-5.
Santra, 2006, Fluorescence lifetime measurements to determine the core-shell nanostructure of FITC-doped silica nanoparticles, J Luminescence 117(1):75-82.
Sawada, 1996, Synthesis and surfactant properties of novel fluoroalkylated amphiphilic oligomers, Chem Commun 2:179-190.
Lunderberg, 1995, Solid-phase technology: magnetic beads to improve nucleic acid detection and analysis, Biotech Ann Rev 1:373-401.
Lundstrom, 2002, Breakthrough in cancer therapy: Encapsulation of drugs and viruses, Curr Drug Disc 19-23.
Lyne, 2002, Structure-based virtual screening: an overview, Drug Disc Tod 7(20):1047-1055.
Ma, 1993, In vitro protein engineering using synthetic tRNA(Ala) with different anticodons, Biochemistry 32(31):7939-45.
Mackenzie, 1985, IABS Symposium on Reduction of Animal Usage in the Development and Control of Biological Products, London, UK, 16 pages.
Mackenzie, 1986, The application of flow microfluorimetry to biomedical research and diagnosis: a review, Dev Biol Stand 64:181-193.
Maclean, 1999, Glossary of terms used in combinatorial chemistry, Pure Appl. Chem. 71(12):2349-2365.
Magdassi, 1984, Multiple Emulsions: HLB Shift Caused by Emulsifier Migration to External Interface, J. Colloid Interface Sci 97:374-379.
Mahajan, 1998, Bcl-2 and Bax Interactions in Mitochondria Probed with Green Florescent Protein and Fluorescence Resonance Energy Transfer, Nat. Biotechnol. 16(6): 547-552.
Mahjoob, 2008, Rapid microfluidic thermal cycler for polymerase chain reaction nucleic acid amplification. Int J HeatMass Transfer;51:2109-22.
Manafi, 2000, New developments in chromogenic and fluorogenic culture media, 2000, International Journal of Food Microbiology, 60, 205-218.
Manley, 1983, In vitro transcription: whole cell extract, Methods Enzymol, 101:568-82.
Manz, 1991, Micromachining of monocrystalline silicon and glass for chemical analysis systems A look into next century's technology or just a fashionable craze, Trends in Analytical Chemistry 10(5):144-149.
Mao, 1991, Substrate effects on the enzymatic activity of alphachymotrypsin in reverse micelles, Biochem Biophys Res Commun, 178(3):1105-12.
Mao, 1992, Kinetic behaviour of alpha-chymotrypsin in reverse micelles: a stopped-flow study, Eur J Biochem 208 (1):165-70.
Mardis, 2008, The impact of next-generation sequencing technology on genetics, Trends Genet 24:133-141.
Margulies, 2005, Genome sequencing in microfabricated high-density picolitre reactors, Nature 437(7057):376-380.
Marks, 1992, Bypassing immunization: building high affinity human antibodies by chain shuffling, BioTechnol 10:779-783.
Marques, 1996, Porous Flow within Concentric Cylinders, Bull Am Phys Soc Div Fluid Dyn 41:1768, 1 page.
Maruno, 1991, Fluorine containing optical adhesives for optical communications systems, J. Appl. Polymer. Sci. 42:2141-2148.
Mason, 1997, Shear Rupturing of Droplets in Complex Fluids, Langmuir, 13(17):4600-4613.
Mastrobattista, 2005, High-throughput screening of enzyme libraries: in vitro evolution of a beta-galactosidase by fuorescence-activated sorting of double emulsions, Chem. Biol. 12(12): 1291-1300.
Masui, 1998, Probing of DNA-Binding Sites of *Escherichia coli* RecA Protein Utilizing 1-anilinonaphthalene-8-Sulfonic Acid, Biochem 37(35):12133-12143.
Matayoshi, 1990, Novel fluorogenic substrates for assaying retroviral proteases by resonance energy transfer, Science 247:954.
Matsubara, 2003, Detection of Single Nucleotide Substitution by Competitive Allele-Specific Short Oligonucleotide Hybridization (CASSOH) With Ummunochromatographic Strip, Human Mutation 22:166-172.
Mattheakis, 1994, An in vitro polysome display system for identifying ligands from very large peptide libraries, PNAS 91:9022-6.
Mayr, 2008, The Future of High-Throughput Screening, JBiomol Screen 13:443-448.

(56) References Cited

OTHER PUBLICATIONS

Mazutis, 2009, Droplet-Based Microfluidic Systems for High-Throughput Single DNA Molecule Isothermal Amplification and Analysis, Anal Chem 81(12):4813-4821.
Mazutis, 2009, Multi-step microfluidic droplet processing: kinetic analysis of an in vitro translated enzyme, Lab Chip 9:2902-2908.
McDonald, 2000, Fabrication of microfluidic systems in poly(dimethylsiloxane), Electrophoresis 21(1):27-40.
McDonald, 2002, Poly(dimethylsiloxane) as a material for fabricating microfluidic devices, Account Chem. Res. 35:491-499.
Melton, 1984, Efficient in vitro synthesis of biologically active RNA and RNA hybridization probes from plasmids containing a bacteriophage SP6 promoter, Nucl. Acids Res. 12(18):7035-7056.
Mendel, 1995, Site-Directed Mutagenesis with an Expanded Genetic Code, Annu Rev Biophys Biomol Struct, 24:435-62.
Mendieta, 1996, Complementary sequence correlations with applications to reflectometry studies, Instrumentation and Development 3(6):37-46.
Metzker, 2010, Sequencing Technologies—the next generation, Nature Reviews, vol. 11, pp. 31-46.
Meylan, 1995, Atom/fragment contribution method for estimating octanol-water partition coefficients, J Pharm Sci. 84(1):83-92.
Michalatos-Beloin, 1996, Molecular haplotyping of genetic markers 10 kb apart by allele-specific long-range PCR, Nucleic Acids Research, 24:4841-4843.
Miele, 1983, Autocatalytic replication of a recombinant RNA, J Mol Biol, 171:281-95.
Milstein, 1983, Hybrid hybridomas and their use in immunohistochemistry, Nature 305:537-540.
Mindlin, 1936, A force at a point of a semi-infinite solid, Physics, 7:195-202.
Minshuil, 1999, Protein evolution by molecular breeding, Curr Opin Chem Biol 3(3): 284-90.
Miroux, 1996, Over-production of proteins in *Escherichia coli*: mutant hosts that allow synthesis of some membrane proteins and globular proteins at high levels, J of Mol Biol 260(3):289-98.
Miyawaki, 1997, Fluorescent Indicators for Ca2+ Based on Green Fluorescent Proteins and Calmodulin, Nature, 388:882-887.
Mize, 1989, Dual-enzyme cascade—an amplified method for the detection of alkaline phosphatase, Anal Biochem 179(2): 229-35.
Mock, 1985, A fluorometric assay for the biotin-avidin interaction based on displacement of the fluorescent probe 2-anilinonaphthalene-6-sulfonic acid, Anal Biochem, 151:178-81.
Moldavan, 1934, Photo-electric technique for the counting of microscopical cells, Science 80:188-189.
Monie, 2005, A Novel Assay Allows Genotyping of the Latent Reservoir for Human Imnunodefi ciency Virus Type 1 in the Resting CD4+ T Cells of Viremic Patients, Journal of Virology, 79(8):5185-5202.
Montigiani, 1996, Alanine substitutions in calmodulin-binding peptides result in unexpected affinity enhancement, J Mol Biol, 258:6-13.
Moore, 1995, Exploration by lamp light, Nature, 374:766-7.
Morrison, 1984, Chimeric human antibody molecules: mouse antigen-binding domains with human constant region domains, PNAS 81:6851-6855.
Unger, 2000, Monolithic microfabricated valves and pumps by multylayersoft lithography, Science 288(5463):113-116.
Utada, 2005, Monodisperse double emulsions generated from a microcapillary device, Science, 308:537-541.
Vainshtein, 1996, Peptide rescue of an N-terminal truncation of the stoffel fragment of Taq DNA polymerase, Protein Science, 5:1785-92.
Van der Sluis, 2013, Dendritic Cell-induced Activation of Latent HIV-1 Provirus in Actively Proliferating Primary T Lymphocytes, PLOS Pathog. 9(3): 16 pages.
Van Dilla, 1968, The fluorescent cell photometer: a new method for the rapid measurement of biological cells stained with fluorescent dyes, Annual Report of the Los Alamos Scientific Laboratory of the University of California (Los Alamos, NM), Biological and Medical Research Groupp (H-4) of the Health Division, Compiled by D. G. Ott, pp. 100-105.
Van Dilla, 1969, Cell Microfluorometry: A Method for Rapid Fluorescence Measurement, Science 163(3872):1213-1214.
Vanhooke, 1996, Three-dimensional structure of the zinc-containing phosphotrieesterase with the bound substrate analog diethy 4-methylbenzylphosphonate, Biochemistry 35:6020-6025.
Varga, 1991, Mechanism of allergic cross-reactions-I. Multispecific binding of ligands to a mouse monoclonal anti-DNP IgE antibody. Mol Immunol 28(6), 641-54.
Vary, 1987, A homogeneous nucleic acid hybridization assay based on strand displacement, Nucl Acids Res 15 (17):6883-6897.
Venkateswaran, 1992, Production of Anti-Fibroblast Growth Factor Receptor Monoclonal Antibodies by In Vitro Immunization, Hybirdoma, 11(6):729-739.
Verhoeyen, 1988, Reshaping human antibodies: grafting an antilysozyme activity, Science, 239:1534-1536.
Vogelstein, 1999, Digital PCR, PNAS 96(16):9236-9241.
Voss, 1993, Kinetic measurements of molecular interactions by spectrofluorometry, J Mol Recognit, 6:51-58.
Wahler, 2001, Novel methods for biocatalyst screening. Curr Opin Chem Biol, 5: 152-158.
Walde, 1988, Structure and activity of trypsin in reverse micelles, Eur J Biochem, 173(2):401-9.
Walde, 1993, Spectroscopic and kinetic studies of lipases solubilized in reverse micelles, Biochemistry, 32(15):4029-34.
Walde, 1994, Oparin's reactions revisited: enzymatic synthesis of poly(adenylic acid) in micelles and self-reproducing vesicles. J Am Chem Soc, 116: 7541-7547.
Walker, 1992, Isothermal in vitro amplification of DNA by a restriction enzyme/DNA polymerase system, PNAS 89(1):392-6.
Walker, 1992, Strand displacement amplification—an isothermal, in vitro DNA amplification technique, Nucleic Acid Res, 20(7):1691-6.
Wang, 1989, Quantitation of mRNA by the polymerase chain reaction. Proc natl Acad Sci USA 86(24), 9717-21.
Wang, 1990, Design and synthesis of new fluorogenic HIV protease substrates based on resonance energy transfer, Tetrahedron Lett., 31:6493.
Wang, 2002, Preparation of Titania Particles Utilizing the Insoluble Phase Interface in a MicroChannel Reactor, Chemical Communications 14:1462-1463.
Wang, 2008, DEP actuated nanoliter droplet dispensing using feedback control, Lab on a Chip 9:901-909.
Wang, 2010, Quantifying EGFR Alterations in the Lung Cancer Genome with Nanofluidic Digital PCR Arrays, Clinical Chemistry 56:4.
Warburton, 1993, Microcapsules for Multiple Emulsions, Encapsulation and Controlled Release, Spec Publ R Soc Chem, 35-51.
Wasserman, 1989, Structure and reactivity of allyl-siloxane monolayers formed by reaction of allcyltrichlorosilanes on silicon substrates, Langmuir 5:1074-1087.
Weaver, 2010, Taking qPCR to a higher level: Analysis of CNV reveals the power of high throughput qPCR to enhance quantitative resolution, Methods 50, 271-276.
Weil, 1979, Selective and accurate initiation of transcription at the Ad2 major late promotor in a soluble system dependent on purified RNA polymerase II and DNA, Cell, 18(2):469-84.
Werle, 1994, Convenient single-step, one tube purification of PCR products for direct sequencing, Nucl Acids Res 22(20):4354-4355.
Wetmur, 2005, Molecular haplotyping by linking emulsion PCR: analysis of paraoxonase 1 haplotypes and phenotypes. Nucleic Acids Res 33(8):2615-2619.
White, 2009, Digital PCR provides sensitive and absolute calibration for high throughput sequencing, BMC Genomics 10:116.
Wick, 1996, Enzyme-containing liposomes can endogenously produce membrane-constituting lipids, Chem Biol 3(4):277-85.
Wiggins, 2004, Foundations of chaotic mixing, Philos Transact A Math Phys Eng Sci 362(1818):937-70.
Williams, 1979, Methotrexate, a high-affinity pseudosubstrate of dihydrofolate reductase, Biochemistry, 18(12):2567-73.

(56) References Cited

OTHER PUBLICATIONS

Williams, 2006, Amplification of complex gene libraries by emulsion PCR, Nature Methods 3(7):545-550.
Wilson, 1999, In vitro selection of functional nucleic acids, Ann. Rev. Biochem. 68: 611-647.
Wittrup, 2001, Protein engineering by cell-surface display. Curr Opin Biotechnology, 12: 395-399.
Wittwer, 1989, Automated polymerase chain reaction in capillary tubes with hot air, Nucleic Acids Res., 17(11) 4353-4357.
Wittwer, 1990, Minimizing the Time Required for DNA Amplification by Efficient Heat Transfer to Small Samples, Anal. Biochem., 186, 328-331.
Wolff, 2003, Integrating advanced functionality in a microfabricated high-throughput fluorescent-activated cell sorter, Lab Chip, 3(1): 22-27.
Woolley, 1994, Ultra-high-speed DNA fragment separations using microfabricated capillary array electrophoresis chips, Proc. Natl. Acad. Sci. USA, 91, 11348-11352.
Woolley, 1996, Functional Integration of PCR Amplification and Capillary Electrophoresis in a Microfabricated DNA Analysis Device, Anal. Chem. 68, 4081-4086.
Wronski, 2002, Two-color, fluorescence-based microplate assay for apoptosis detection. Biotechniques, 32:666-668.
Wu, 1989, The ligation amplification reaction (LAR)-amplification of specific DNA sequences using sequential rounds of template-dependent ligation, Genomics 4(4):560-9.
Wyatt, 1991, Synthesis and purification of large amounts of RNA oligonucleotides, Biotechniques 11(6):764-9.
Xia, 1998, Soft Lithography, Angew. Chem. Int. Ed. 37:550-575.
Xia, 1998, Soft Lithography, Ann. Rev. Mat. Sci. 28:153-184.
Xiao, 2007, Rapid DNA mapping by fluorescent single molecule detection, Nucleic Acids Research 35:1-12.
Xing, 2011, Novel structurally related compounds reactivate latent HIV-1 in a bcl-2-transduced primary CD4+ T cell model without inducing global T cell activation, Journal of Antimicrobial Chemotherapy, 67(2):398-403.
Xu, 2005, Generation of monodisperse particles by using microfluidics: control over size, shape, and composition, Angew. Chem. Int. Ed. 44:724-728.
Joyce, 1994, In vitro Evolution of Nucleic Acids, Curr. Opp. Structural Biol, 4: 331-336.
Kadir, 1990, Haem binding to horse spleen ferritin, Febs Lett, 276: 81-4.
Kallen, 1966, The mechanism of the condensation of formaldehyde with tetrahydrofolic acid, J. Biol. Chem., 241:5851-63.
Kambara, 1988, Optimization of Parameters in a DNA Sequenator Using Fluorescence Detection, Nature Biotechnology 6:816-821.
Kamensky, 1965, Spectrophotometer: new instrument for ultrarapid cell analysis, Science 150(3696):630-631.
Kanouni, 2002, Preparation of a stable double emulsion (W1/0/W2): role of the interfacial films on the stability of the system, Adv. Collid. Interf. Sci., 99(3): 229-254.
Karapatis, 1998, Direct rapid tooling:a review of current research, Rapid Prototyping Journal, 4(2):77-89.
Katanaev, 1995, Viral Q beta RNA as a high expression vector for mRNA translation in a cell-free system, Febs Lett, 359:89-92.
Katsura, 2001, Indirect micromanipulation of single molecules in water-in-oil emulsion, Electrophoresis, 22:289-93.
Kawakatsu, 1997, Regular-sized cell creation in microchannel emulsification by visual microprocessing method, Journal of the American Oil Chemists Society, 74:317-21.
Keana, 1990, New reagents for photoaffinity labeling: synthesis and photolysis of functionalized perfluorophenyl azides, J. Org. Chem. 55(11):3640-3647.
Keefe, 2001, Functional proteins from a random-sequence library, Nature, 410: 715-718.
Keij, 1994, High-speed photodamage cell sorting: An evaluation of the ZAPPER prototype, Methods in cell biology, 42:371-358.

Kelly, 2005, Detection of Vascular Adhesion Molecule-1 Expression Using a Novel Multimodal Nanoparticle, Circulation Research 96:327-336.
Kelly, 2007, Miniaturizing chemistry and biology in microdroplets, Chem Commun 18:1773-1788.
Kerker, 1983, Elastic and inelastic light scattering in flow cytometry, Cytometry, 4:1-10.
Khandjian, 1986, UV crosslinking of RNA to nylon membrane enhances hybridization signals, Mol. Bio. Rep. 11:107-115.
Kheir, 2012, Oxygen Gas-Filled Microparticles Provide Intravenous Oxygen Delivery, Science Translational Medicine 4(140):140ra88 (10 pages).
Kim, 2003, Type II quantum dots: CdTe/CdSe (core/shell) and CdSe/ZnTe (core/shell) heterostructures, J. Am Chem Soc. 125:11466-11467.
Kim, 2004, Comparative study on sustained release of human growth hormone from semi-crystalline poly(L-lactic acid) and amorphous poly(D,L-lactic-co-glycolic acid) microspheres: morphological effect on protein release, Journal of Controlled Release, 98(1):115-125.
Kircher, 2010, High-throughput DNA sequencing-concepts and limitations, Bioessays 32(6):524-536.
Kiss, 2008, High-throughput quantitative polymerase chain reaction in picoliter droplets, Anal. Chem 80:8975-8981.
Kitagawa, 1995, Manipulation of a single cell with microcapillary tubing based on its electrophoretic mobility, Electrophoresis 16:1364-1368.
Klug, 1994, All you wanted to know about selex, Molecular Biology Reports, 20:97-107.
Klug, 1995, Gene Regulatory Proteins and Their Interaction with DNA, Ann NY Acad Sci, 758: 143-60.
Klug, 1995, Protein motifs 5. Zinc fingers, FASEB J 9(8):597-604.
Knaak, 1995, Development of partition coefficients, Vmax and Km values, and allometric relationships, Toxicol Lett. 79(I-3):87-98.
Knight, 1998, Hydrodynamic Focusing on a Silicon Chip: Mixing Nanoliters in Microseconds, Physical Review Lett 80(17):3863-3866.
Koeller, 2001, Enzymes for chemical synthesis, Nature 409:232-240.
Kohler, 1975, Continuous cultures of fused cells secreting antibody of predefined specificity, Nature, 256:495-7.
Kojima, 2005, PCR amplification from single DNA molecules on magnetic beads in emulsion: application for high-throughput screening of transcription factor targets. Nucleic Acids Res. 33:e150, 9 pages.
Kolb, 1995, Cotranslational folding of proteins, Biochem Cell Biol, 73:1217-20.
Komatsu, 2001, Roles of cytochromes P450 1A2, 2A6, and 2C8 in 5-fluorouracil formation ram tegafur, an anticancer prodrug, in human liver microsomes. Drug Met. Disp., 28:1457-1463.
Kopp, 1998, Chemical amplification: continuous flow PCR on a chip, Science, 280:1046-48.
Koster, 2008, Drop-based microfluidic devices for encapsulation of single cells, Lab on a Chip 8:1110-1115.
Kowalczykowski, 1994, Biochemistry of homologous recombination in *Escherichia coli*, Microbiol Rev 58(3):401-65.
Kozbor, 1984, A human hybrid myeloma for production of human monoclonal antibodies, J. Immunol., 133:3001-3005.
Krafft, 1991, Synthesis and preliminary data on the biocompatibility and emulsifying properties of perfluoroalkylated phosphoramidates as injectable surfactants, Eur. J. Med. Chem., 26:545-550.
Krafft, 2001, Fluorocarbons and fluorinated amphiphiles in drug delivery and biomedical research, Adv Rev Drug Disc 47:209-228.
Krafft, 2003, Emulsions and microemulsions with a fluorocarbon phase, Colloid and Interface Science 8(3):251-258.
Kralj, 2005, Surfactant-enhanced liquid-liquid extraction in microfluidic channels with inline electric-field enhanced coalescence, Lab Chip 5:531-535.
Kricka, 1996, Micromachining: a new direction for clinical analyzers, Pure and Applied Chemistry 68(10):1831-1836.
Kricka, 2003, Microchip PCR, Anal Bioanal Chem 377(5):820-825.
Kritikou, 2005, "It's cheaper in the Picolab," Nature, September, vol. 6, 1 page.

(56) References Cited

OTHER PUBLICATIONS

Krumdiek, 1980, Solid-phase synthesis of pteroylpolyglutamates, Methods Enzymol, 524-29.
Kruth, 2003, Lasers and materials in selective laser sintering, Assembly Automation, 23(4):357-371.
Kumagai, 1994, Ablation of polymer films by a femtosecond high-peak-power Ti:sapphire laser at 798 nm, Applied Physics Letters, 65(14):1850-1852.
Kumar, 1989, Activity and kinetic characteristics of glutathione reductase in vitro in reverse micellar waterpool, Biochem Biophys Acta, 996(1-2):1-6.
Kumaresan, 2008, High-throughput single copy DNA amplification and cell analysis in engineered nanoliter droplets, Anal Chem, 80:3522-3529.
Lage, 2003, Whole genome analysis of genetic alterations in small DNA samples using hyperbranched strand displacement amplification and array-CGH, Genome Res 13:294-307.
Adang, 2001, The contribution of combinatorial chemistry to lead generation: an interim analysis, Curr Med Chem 8:985-998.
Affholter 1999, Engineering a Revolution, Chemistry in Britain 48-51.
Agrawal, 1990, Site-specific functionalization of oligodeoxynucleotides for non-radioactive labelling, Tetrahedron Let 31:1543-1546.
Aharoni, 2005, High-Throughput screens and selections of enzyme-encoding genes, Curr Opin Chem Biol, 9(2):210-6.
Ahn, 2006, Dielectrophoretic manipulation of drops for high-speed microluidic sorting devices, Applied Phys Lett 88:024104.
Akasheh, 2004, Development of piezoelectric micromachined ultrasonic transducers, Sensors and Actuators A Physical, 111:275-287.
Allen, 2000, High throughput fluorescence polarization: a homogeneous alternative to radioligand binding for cell surface receptors J Biomol Screen. 5(2):63-69.
Ammar, 2003, UV/Vis absorption and fluorescence spectroscopic study of novel symmetrical biscoumarin dyes, Dyes and Pigments 57:259-265.
Amstutz, 2001, In vitro display technologies: novel developments and applications. Curr Opin Biotech 12:400-405.
Anarbaev, 1998, Klenow fragment and DNA polymerase alpha-primase fromserva calf thymus in water-in-oil microemulsions, Biochim Biophy Acta 1384:315-324.
Anderson, 1983, Preparation of a cell-free protein-synthesizing system from wheat germ, Methods Enz 101:635-644.
Anderson, 1993, Restriction endonucleases and modification methylases, Curr Op Struct Biol 3:24-30.
Ando, 1999, PLGA microspheres containing plasmid DNA: preservation of supercoiled DNA via cryopreparation and carbohydrate stabilization, J Pharm Sci 88(1):126-130.
Angell, 1983, Silicon micromechanical devices, Scientific Am 248:44-55.
Anhuf, 2003, Determination of SMN1 and SMN2 copy number using TaqMan technology, Hum Mutat 22(1):74-78.
Anna, 2003, Formation of dispersions using flow focusing in microchannels, Appl Phys Lett82(3):364-366.
Armstrong, 1996, Multiple-Component condensation strategies for combinatorial library synthesis, Acc Chem Res 29(3):123-131.
Ashkin, 1987, Optical trapping and manipulation of single cells using infrared laser beams, Nature 330:769-771.
Ashkin, 1987, Optical trapping and manipulation of viruses and bacteria, Science 235(4795):1517-20.
Auroux, 2002, Micro Total Analysis Systems 2: Analytical standard operations and applications, Anal Chem 74(12):2637-2652.
Baccarani, 1977, *Escherichia coli* dihydrofolate reductase: isolation and characterization of two isozymes, Biochemistry 16(16):3566-72.
Bagwe, 2001, Improved drug delivery using microemulsions: rationale, recent progress, and new horizons, Crit Rev Ther Drug Carr Sys 18(1):77-140.
Baker, 2010, Clever PCR: more genotyping, smaller volumes Nat Meth 7:351-356.

Ballantyne, 1973, Selective area metallization by electron-beam controlled direct metallic deposition, J Vac Sci Tech 10:1094.
Barany, 1991, Genetic disease detection and DNA amplification using cloned thermostable ligase, PNAS 88(1):189-93.
Barany, 1991, The ligase chain reaction in a PCR World, PCR Meth App 1(1):5-16.
Baret, 2009, Fluorescence-activated droplet sorting (FADS): efficient microfluidic cell sorting based on enzymatic activity, Lab Chip 9:1850-1858.
Baret, 2009, Kinetic aspects of emulsion stabilization by surfactants: a microfluidic analysis, Langmuir 25:6088-6093.
Baroud, 2004, Multiphase flows in microfluidics, Physique 5:547-555.
Bauer, 1999, Advances in cell separation: recent developments in counterflow centrifugal elutriation and continuous flow cell separation, J Chromot 722:55-69.
Beebe, 2000, Functional hydrogel structures for autonomous flow control inside microfluidic channels, Nature 404:588-590.
Beer, 2007, On-chip, real-time, single-copy polymerase chain reaction in picoliter droplets, Anal Chem 79 (22):8471-8475.
Beer, 2008, On-chip single-copy real-time reverse transcription PCR in isolated picoliter droplets, Anal Chem 80(6):1854-1858.
Bein, 1999, Efficient assays for combinatorial methods for the eiscovery of catalysts, Agnew Chem Int Ed 38:3:323-26.
Benichou, 2002, Double emulsions stabilized by new molecular recognition hybrids of natural polymers, Polym Adv Tech 13:1019-1031.
Benner, 1994, Expanding the genetic lexicon, Trends Biotech 12:158-63.
Benning, 2000, The binding of substrate analogs to phosphotriesterase. J Biol Chem 275:30556-30560.
Berman, 1987, An agarose gel electrophoresis assay for the detection of DNA-binding activities in yeast cell extracts, Meth Enz 155:528-37.
Bernath, 2004, In Vitro Compartmentalization by double emulsions: sorting and gene enrichment by FACS Anal Biochem 325:151-157.
Bernath, 2005, Directed evolution of protein inhibitors of DNA-nucleases by in vitro compartmentalization (IVC) and nano-droplet delivery, J Mol Biol 345(5):1015-26.
Betlach, 1976, A restriction endonuclease analysis of the bacterial plasmid controlling the EcoRI restriction and modification of DNA, Fed Proc 35:2037-2043.
Bibette, 1999, Emulsions: basic principles, Rep Prog Phys 62:969-1033.
Bico, 2002, Rise of liquids and bubbles in angular capillary tubes, J Colloid & Interface Sc 247:162-166.
Bico, 2002, Self-Propelling Slugs, J Fluid Mech 467:101-127.
Binder, 2009, Mismatch and G-stack modulated probe signals on SNP microarrays, PLoS One, 4(11):e7862.
Binladen, 2007, The use of coded PCR primers enables high-throughput sequencing of multiple homolog amplification products by 454 parallel sequencing, PLoSOne 2(2):e197.
Blanchet, 1993, Laser Ablation and the Production of Polymer Films, Science, 262(5134):719-721.
Boder, 1997, Yeast surface display for screening combinatorial polypeptide libraries, Nat Biotech 15(6):553-7.
Bosque, 2009, Induction of HIV-1 latency and reactivation in primary memory CD4+ T cells, Blood, 113(1):58-65.
Bougueleret, 1984, Characterization of the gene coding for the EcoRV restriction and modification system of *E coli*, Nucleic Acids Res 12(8):3659-76.
Stauber, 1993, Rapid generation of monoclonal antibody-secreting hybridomas against African horse sickness virus by in vitro immunization and the fusion/cloning technique, J Immunol Meth 161(2):157-168.
Stemmer, 1994, DNA shuffling by random fragmentation and reassembly: in vitro recombination for molecular evolution. PNAS 91(22):10747-51.
Stemmer, 1994, Rapid evolution of a protein in vitro by DNA shuffling, Nature 370(6488):389-91.
Stober, 1998, Controlled growth of monodisperse silica spheres in the micron size range, J Colloid Interface Sci 26(1):62-69.

(56) References Cited

OTHER PUBLICATIONS

Stofko, 1992, A single step purification for recombinant proteins, Febs Lett 302:274-278.
Stone, 2004, Engineering flows in small devices: microfluidics toward a lab-on-a-chip, Ann Rev Fluid Mech 36:381-441.
Strizhkov, 2000, PCR amplification on a microarray of gel-immobilized oligonucleotides: Detection of bacterial toxin- and drug-resistant genes and their mutations, BioTechniques 29(4):844-857.
Strommenger, 2003, Multiplex PCR assay for simultaneous detection of nine clinicly relevant antibiotic resistance genes in *S aureus*, J Clin Microb 41(9):4089-4094.
Stroock, 2002, Chaotic mixer for microchannels, Science 295(5555):647-651.
Studer, 1997, Fluorous synthesis: a fluorous-phase strategy for improving separation efficiency in organic synthesis, Science 275:823-826.
Sugiura, 2001, Interfacial tension driven monodispersed droplet formation from mtcrofabricated channel array, Langmuir 17:5562-5566.
Sugiura, 2002, Effect of channel structure on microchannel emuisification, Langmuir 18:5708-5712.
Sundberg, 1995, Spatially-addressable immobilisation of macromolecules on solid supports, J Am Chem Soc 117:12050-12057.
Sung, 2005, Chip-based microfluidic devices coupled with electrospray ionization-mass spectrometry, Electrophoresis 26:1783-1791.
Sutcliffe, 1986, Dynamics of UV laser ablation of organic polymer surfaces, J Appl Phys 60(9):3315-3322.
Suzuki, 1996, Random mutagenesis of thermus aquaticus DNA polmerase I: concordance of immutable sites in vivo with the crystal structure, PNAS 93:96701-9675.
Syed, 2009, Next-generation sequencing library preparation: simultaneous fragmentation and tagging using in vitro transposition, Nat Meth 6:1-2.
Takayama, 1999, Patterning cells and their environmnets using multiple laminar fluid flows in cappillary networks, PNAS 96:5545-5548.
Takeuchi, 2005, An axisymmetric flow-focusing microfluidic device, Adv Mater 17(8):1067-1072.
Taly, 2007, Droplets as microreactors for high-throughput biology, Chembiochem 8(3):263-272.
Tan, 2003, Controlled fission of droplet emulsions in bifurcating microfluidic channels, 12th Int Conf SSAM 28-31.
Tan, 2003, Microfluidic liposome generation from monodisperse droplet emulsion, Summer Bioeng Conf, Florida, 2 pages.
Tan, 2003, Monodisperse droplet emulsions in co-flow microfluidic channels, Micro TAS, 2 pages.
Tan, 2004, Design of microluidic channel geometries for the control of droplet volume, chemical concentration, and sorting, Lab Chip 4(4):292-298.
Tang, 2009, A multi-color fast-switching microfluidic droplet dye laser, Lab Chip 9:2767-2771.
Taniguchi, 2002, Chemical reactions in microdroplets by electrostatic manipulation of droplets in liquid media, Lab Chip 2:19-23.
Tawfik, 1998, Man-made cell-like compartments for molecular evolution, Nat Biotech 7(16):652-56.
Taylor, 1934, The formation of emulsions in definable field of flow, Proc R Soc London A 146(858):501-523.
Taylor, 1991, Characterization of chemisorbed monolayers by surface potential measurments, J Phys D Appl Phys 24:1443.
Tencza, 2000, Development of a fluorescence polarization-based diagnostic assay for equine infectious anemia virus, J Clin Microbiol 38(5):1854-185.
Terray, 2002, Fabrication of linear colloidal structures for microfluidic applications, Applied Phys Lett 81(9):1555-1557.
Terray, 2002, Microfluidic control using colloidal devices, Science 296(5574):1841-1844.
Tewhey, 2009, Microdroplet based PCR environment for large scale targeted sequence, Nat Biotech 27(11):1025-1031.
Theberge, 2010, Microdroplets in microfluidics: an evolving platform for discoveries in chemistry and biology, Angew Chem Int Ed 49(34):5846-5868.
Thompson, 1983, Introduction to Lithography, ACS Symp Ser 219:1-13.
Thorsen, 2001, Dynamic pattern formation in a vesicle-generating microfluidic device, Phys Rev Lett 86(18):4163-4166.
Thorsen, 2002, Microfluidic large-scale integration, Science 298:580-584.
Thorsen, 2003, Microfluidic technologies for highthroughput screening applications, California Institute of Technology.
Tice, 2003, Formation of droplets and mixing in multiphase microfluidics at low values of the reynolds and the capillary numbers, Langmuir 19:9127-9133.
Tice, 2004, Effects of viscosity on droplet formation and mixing in microfluidic channels, Analytica Chimica Acta 507:73-77.
Titomanlio, 1990, Capillary experiments of flow induced crystallization of HDPE, AIChe J 36(1):13-18.
Tleugabulova, 2004, Evaluating formation and growth mechanisms of silica particles using fluorescence anisotropy decay analysis, Langmuir 20(14):5924-5932.
Tokatlidis, 1995, Nascent chains: folding and chaperone infraction during elongation on ribosomes, Philos Trans R Soc Lond B Biol Sci, 348:89-95.
Tokeshi, 2002, Continuous-flow chemical processing on a microchip by combining microunit operations and a multiphase flow network, Anal Chem 74(7):1565-1571.
Tokumitsu, 1999, Preparation of gadopentetic acid-loaded chitosan microparticles for gadolinium neutron-capture therapy of cancer by a novel emulsion-droplet coalescence technique, Chem Pharm Bull 47(6):838-842.
Tonelli et al., 2002, Perfluoropolyether functional oligomers: unusual reactivity in organic chemistry, Journal of fluorine Chemistry, 118; 107-121.
Trolier-McKinstry, 2004, Thin Film Piezoelectric for MEMS, Journal of Electroceramics 12:7-17.
Tsuchiya, 2007, On-chip polymerase chain reaction microdevice employing a magnetic droplet-manipulation system, Sens Actuators B 130:583-588.
Tuzel, 2006, Region Covariance: A Fast Descriptor for Detection and Classification, European Conference on Computer Vision (ECCV), 14 pages.
Umbanhowar, 2000, Monodisperse Emulsion Generation via Drop Break Off in a Coflowing Stream, Langmuir 16(2):347-351.
Ellman, 1991, Biosynthetic method for introducing unnatural amino acids site-specifically into proteins, Methods Enzymol, 202:301-36.
Endo, 1996, Autocatalytic decomposition of cobalt complexes as an indicator system for the determination of trace amounts of cobalt and effectors, Analyst 121:391-394.
Endo, 1998, Kinetic determination of trace cobalt by visual autocatalytic indication, Talanta 47:349-353.
Engl, 2005, Droplet Traffic at a Simple Junction at Low Capillary Numbers Physical Review Letters, vol. 95, 208304, 1 page.
Eow, 2002, Electrocoalesce-separators for the separation of aqueous drops from a flowing dielectric viscous liquid, Separation and Purification Tech 29:63-77.
Eow, 2002, Electrostatic and hydrodynamic separation of aqueous drops in a flowing viscous oil, Chemical Eng Proc 41:649-657.
Eow, 2002, Electrostatic enhancement of coalescence of water droplets in oil: a review of the technology, Chemical Engineeing Journal 85:357-368.
Eow, 2003, Motion, deformation and break-up of aqueous drops in oils under high electric field strengths, Chemical Eng Proc 42:259-272.
Eow, 2003, The behavior of a liquid-liquid interface and drop-interface coalescence under the influence of an electric field, Colloids and Surfaces A: Physiochern. Eng. Aspects 215:101-123.
Eriksson, 2013, Comparative analysis of measures of viral reservoirs in HIV-1 eradication studies, PLoS Pathogens 9(2):e1003174, 17 pages.
Faca, 2008, A mouse to human search for plasma proteome changes associated with pancreatic tumor development, PLoS Med 5(6):e123:0953-0967.

(56) References Cited

OTHER PUBLICATIONS

Fahy, 1991, Self-sustained sequence replication (3SR): an isothermal transcription-based amplification system alternative to PCR, PCR Methods Appl 1:25-33.
Fan, 1994, Micromachining of capillary electrophoresis injectors and separators on glass chips and evaluation of flow at capillary intersections. Anal Chem 66:177-184.
Fan, 2007, Detection of Aneuploidy with Digital PCR, available at https://arxiv.org/ftp/arxiv/papers /0705/0705.1 030.pdf, 16 pages.
Fastrez, 1997, In vivo versus in vitro screening or selection for catalytic activity in enzymes and abzymes, Mol Biotechnol 7(1):37-55.
Fettinger, 1993, Stacked modules for micro flow systems in chemical analysis: concept and studies using an enlarged model. Sens Actuat B. 17:19-25.
Fiedler, 1998, Dielectrophoretic sorting of particles and cells in a microsystem, Anal Chem 70(9):1909-1915.
Field, 1988, Purification of a RAS-responsive adenylyl cyclase complex from *Saccharomyces cervisiae* by use of an epitope addition method. Mol Cell Biol, 8: 2159-2165.
Fields, 1989, A novel genetic system to detect protein-protein interactions, Nature 340(6230):245-6.
Filella, 1994, TAG-72, CA 19.9 and CEA as tumor markers in gastric cancer, Acta Oncol. 33(7):747-751.
Finch, 1993, Encapsulation and controlled release, Spec Publ R Soc Chem, 138:35, 12 pages.
Fingas, 1997, Studies of Water-In-Oil Emulsions: Stability Studies, Environment Canada, Proceedings of the Twentieth Arctic Marine Oilspill Program Technical Seminer, 1-20.
Fire, 1995, Rolling replication of short DNA circles, PNAS 92(10):4641-5.
Firestine, 2000, Using an AraC-based three hybrid system to detect biocatalysts in vivo, Nat Biotechnol 18: 544-547.
Fisher, 2004, Cell Encapsulation on a Microfluidic Platform, The Eighth International Conference on Miniaturised Systems for Chemistry and Life Scieces, MicroTAS, Malmo, Sweden.
Fletcher, 2002, Micro reactors: principles and applications in organic synthesis, Tetrahedron 58:4735-4757.
Fluri, 1996, Integrated capillary electrophoresis devices with an efficient postcolumn reactor in planar quartz and glass chips, Anal Chem 68:4285-4290.
Fornusek, 1986, Polymeric microspheres as diagnostic tools for cell surface marker tracing, Crit Rev Ther Drug Carrier Syst, 2:137-74.
Fowler, 2002, Enhancement of Mixing By Droplet-Based Microfluidics, Int Conf MEMS 97-100.
Frenz, 2008, Reliable microfluidicon-chip incubation of droplets in delay-lines, Lab on a Chip 9:1344-1348.
Fu, 1999, A microfabricated fluorescence-activated cell sorter, Nature Biotechnology, 17(11):1109-1111.
Fu, 2002, An Integrated Microfabricated Cell Sorter, Anal. Chem., 74: 2451-2457.
Fulton, 1997, Advanced multiplexed analysis with the FlowMetrix system, Clin Chem 43:1749-1756.
Fulwyler, 1965, Electronic Separation of Biological Cells by Volume, Science 150(3698):910-911.
Galan, 2010, A 454 multiplex sequencing method for rapid and reliable genotyping of highly polymorphic genes in large-scale studies., BMC Genomics 11(296):1-15.
Gallarate, 1999, On the stability of ascorbic acid in emulsified systems for topical and cosmetic use, Int J Pharm 188(2):233-241.
Ganan-Calvo, 1998, Generation of Steady Liquid Microthreads and Micron-Sized Monodisperse Sprays and Gas Streams, Phys Rev Lett 80(2):285-288.
Ganan-Calvo, 2001, Perfectly Monodisperse Microbubbling by Capillary Flow Focusing, Phys Rev Lett 87(27) :274501-1-4.
Garcia-Ruiz, 1994, Investigation on protein crystal growth by the gel acupuncture method, Acta, Cryst., D50, 99. pp. 484-490.
Garcia-Ruiz, 2001, A super-saturation wave of protein crystallization, J. Crystal Growth, 232:149-155.
Garstecki, 2004, Formation of monodisperse bubbles in a microfiuidic flow-focusing device, Appl Phys Lett 85(13):2649-2651.
Gasperlin, 1994, The structure elucidation of semisolid w/o emulsion systems containing silicone surfactant, Intl J Pharm, 107:51-6.
Gasperlin, 2000, Viscosity prediction of lipophillic semisolid emulsion systems by neural network modeling, Intl J Pharm, 196:37-50.
Gelderblom, 2008, Viral complemntation allows HIV-1 replication without integration, Retrovirology 5:60.
Georgiou, 1997, Display of heterologous proteins on the surface of microorganisms: from the screenign of combinational libraires to live recombinant vaccines Nat Biotechnol 15(1), 29-34.
Georgiou, 2000, Analysis of large libraries of protein mutants using flow cytometry, Adv Protein Chem, 55: 293-315.
Gerdts, 2004, A Synthetic Reaction NetWork: Chemical Amplification Using Nonequilibrium Autocatalytic Reactions Coupled in Time, J. Am. Chem. Soc 126:6327-6331.
Ghadessy, 2001, Directed Evolution of Polymerase Function by Compartmentalized Self-Replication, PNSAS 98(8):4552-4557.
Gibbs, 1989, Detection of single DNA base differences by competitive oligonucleotide priming, Nucleic Acids Res. 17(7):2437-48.
Gilliland, 1990, Analysis of cytokine mRNA and DNA: Detection and quantitation by competitive polymerase chain reaction, PNAS, 87(7):2725-9.
Heyries, 2011, Megapixel digital PCR, Nat. Methods 8, 649-651.
Hildebrand, 1949, Liquid-Liquid Solubility of Perfluoromethylcyclohexane with Benzene, Carbon Tetrachloride, Chlorobenzene, Chloroform and Toluene, J. Am. Chem. Soc, 71:22-25.
Hindson, 2011, High-Throughput Droplet Digital PCR System for Absolute Quantitation of DNA Copy Number Anal Chem., 83, 8604-8610.
Hjelmfelt, 1993, Pattern-Recognition in Coupled Chemical Kinetic Systems, Science, 260(5106):335-337.
Ho, 1989, Site-directed mutageneiss by overlap extension using the polymerase chain reaction, Gene, 77(1):51-9.
Hochuli, 1987, New metal chelate adsorbent selective for proteins and peptides containing neighbouring histidine residues, J Chromatogr 411: 177-84.
Holmes, 1995, Reagents for Combinatorial Organic Synthesis: Development of a New O-Nitrobenzyl Photolabile Linder for Solid Phase Synthesis, J. OrgChem., 60: 2318-2319.
Holtze, 2008, Biocompatible surfactants for water-in-fluorocarbon emulsions, Lab Chip, 8, 1632-1639.
Hong, 1999, Stereochemical constraints on the substrate specificity of phosphodiesterase, Biochemistry, 38:1159-1165.
Hoogenboom, 1997, Designing and optimizing library selection strategies for generating high-affinity antibodies, Trends Biotechnol, 15:62-70.
Hopfinger, 1996, Explosive Breakup of a Liquid Jet by a Swirling Coaxial Jet, Physics of Fluids 8(7):1696-1700.
Hopman, 1998, Rapid synthesis of biotin-, digoxigenin-, trinitrophenyl-, and fluorochrome-labeled tyramides and their application for In situ hybridization using CARD amplification, J of Histochem and Cytochem, 46(6):771-77.
Horton, 1989, Engineering hybrid genes without the use of restriction enzymes: gene splicing by overlap extension, Gene 77(1):61-8.
Hosokawa, 1999, Handling of Picoliter Liquid Samples in a Poly(dimethylsiloxane)-Based Microfluidic Device, Analytical Chemistry, 71(20):4781-4785.
Hsieh, 2009, Rapid label-free DNA analysis in picoliter microfluidic droplets using FRET probes, Microfluidics and nanofluidics 6(3):391-401.
Hsu, 1999, et al., Comparison of process parameters for microencapsulation of plasmid DNA in poly(D, L-lactic-co-glycolic acid microspheres, J Drug Target, 7:313-23.
Hua, 2010, Multiplexed Real-Time Polymerase Chain Reaction on a Digital Microfluidic Platform, Analytical Chemistry 82(6):2310-2316.
Huang, 1991, Kinetic assay of fluorescein mono-beta-D-galactosidase hydrolysis by beta-galactosidase: a front-face measurement for strongly absorbing fluorogenic substrates, Biochemistry, 30:8530-4.

(56) References Cited

OTHER PUBLICATIONS

Huang, 1992, A sensitive competitive ELISA for 2,4-dinitrophenol using 3,6-fluorescein diphosphate as a fluorogenic substrate, J Immunol Meth, 149:261.
Huang, 2004, Continuous particle separation through deterministic lateral displacement, Science 304(5673):987-990.
Huang, 2007, Identification of 8 foodborne pathogens by multicolor combinational probe coding technology in a single real-time PCR, Clin Chem., 53(10):1741-8.
Hubert, 2003, Data Concordance from a Comparison between Filter Binding and Fluorescence Polarization Assay Formats for Identification of RUOCK-II Inhibitors, J biomol Screen 8(4):399-409.
Huebner, 2007, Quantitative detection of protein expression in single cells using droplet microfluidics, Chem Com 12:1218-1220.
Hug, 2003, Measurement of the number of molecules of a single mRNA species in a complex mRNA preparation. J Theor Biol.; 221(4):615-24.
Hung, 2004, Controlled Droplet Fusion in Microfluidic Devices, MicroTAS 2004, Sep. 26-30, Malmo, Sweden.
Hung, 2004, Optimization of Droplet Generation by controlling PDMS Surface Hydrophobicity, 2004 ASME International Mechanical Engineering Congress and RD&D Expo, Nov. 13-19, Anaheim, CA, 47-48.
Hutchison, 2005, Cell-free cloning using Phi29 polymerase, PNAS 102(48):17332-17336.
Ibrahim, 2003, High-speed cell sorting: fundamentals and recent advances, Curr Opin Biotchnol, 14(1):5-12.
Ikeda, 2000, Bioactivation of tegafur to 5-fluorouracil is catalyzed by cytochrome P-450 2A6 in human liver microsomes in vitro, Clin Cancer Res 6(11):4409-4415.
Illumina, 2010, Genomic Sequencing, data Sheet, 6 pages.
Inai, 1993, Immunohistochemical detection of an enamel protein-related epitope in rat bone at an early stage of osteogenesis. Histochemistry 99(5):335-362.
Invitrogen, 2008, Specification sheet for Dynabeads® Oligo (dT)25, http://www.invitrogen.com, 2 pages.
Ismagilov, 2003, Integrated Microfluidic Systems, Angew. Chem. Int. Ed 42:4130-4132.
Jakobovits, 1993, Analysis of homozygous mutant chimeric mice:deletion of the immunoglobulin heavy-chain joining region blocks B-cell development and antibody production, PNAS USA 90:2551-255.
Jakobovits, 1993, Germ-line transmission and expression of a human-derived yeast artificial chromosome, Nature 362:255-258.
Janda, 1997, Chemical selection for catalysis in combinatorial antibody libraries, Science, 275:945-948.
Jang, 2003, Controllable delivery of non-viral DNA from porous scaffold, J Controlled Release 86(1):157-168.
Jarvie, 2007, Amplicon Sequencing, Roche Dx Application Note No. 5 (16 pages).
Jermutus, 1998, et al., Recent advances in producing and selecting functional proteins by using cell-free translation, Curr Opin Biotechnol 9(5): 534-48.
Jo, 2003, Encapsulation of Bovine Serum Albumin in Temperature-Programmed Shell-in-Shell Structures, Macromol. Rapid Comm 24:957-962.
Joerger, 1995, Analyte detection with DNA-labeled antibodies and polymerase chain reaction, Clin. Chem. 41(9):1371-7.
Johannsson, 1988, Amplification by Second Enzymes, In ELISA and Other Solid Phase Immunoassays, Kemeny et al (ed.), Chapter 4, pp. 85-106 John Wiley.
Johannsson, 1991, Heterogeneous Enzyme Immunoassays, In Principles and Practice of Immunoassay, pp. 295-325 Stockton Press.
Johnson, 1993, Human antibody engineering: Current Opinion in Structural Biology, 3:564-571.
Johnson, 2002, Protein tyrosine phosphatase 1B inhibitors for diabetes, Nature Review Drug Discovery 1, 696-709.
Jones, 1986, Replacing the complementarity-determining regions in a human antibody with those from a mouse, Nature, 321:522-525.
Jones, 1997, Quenched Bodipy dye-labeled casein substrates for the assay of protease activity by direct fluorescence measurement, Anal Biochem, 251:144-152.
Jones, 1999, Glowing jellyfish, luminescence and a molecule called coelenterazine, Trends Biotechnol. 17(12):477-81.
Joo, 1999, Laboratory evolution of peroxide-mediated cytochrome P450 hydroxylaion, Nature 399:670.
Joos, 1997, Covalent attachment of hybridizable oligonucleotides to glass supports, Analytical Biochemistry 247:96-101.
Moudrianakis, 1965, Base sequence determination in nucelic acids with the electron microscope 3. Chemistry and microscopy of guanine-labeled DNA, PNAS 53:564-71.
Mueth, 1996, Origin of stratification in creaming emulsions, Physical Review Letters 77(3):578-581.
Mulbry, 1989, Parathion hydrolase specified by the Flavobacterium opd gene: relationshio between the gene and protein. J Bacteriol, 171: 6740-6746.
Mulder, 1993, Characterization of two human monoclonal antibodies reactive with HLA-B12 and HLA-B60, respectively, raised by in vitro secondary immunization of peripheral blood lymphocytes, Hum. Immunol 36(3):186-192.
Munson, 1980, Ligand: a versatile computerized approach for characterization of ligand-binding systems, Analytical Biochemistry, 107:220-239.
Nakano, 1994, High speed polymerase chain reaction in constant flow, Biosci Biotech and Biochem, 58:349-52.
Nakano, 2003, Single-molecule PCR using water-in-oil emulsion, J Biotech, 102:117-124.
Nakano, 2005, Single-molecule reverse transcription polymerase chain reaction using water-in-oil emulsion, J Biosci Bioeng 99:293-295.
Nametkin, 1992, Cell-free translation in reversed micelles, FEB Letters, 309(3):330-32.
Narang, 1979, Improved phosphotriester method for the synthesis of gene fragments, Methods Enzymol, 68:90-98.
Neiman, 2011, Decoding a substantial set of samples in parallel by massive sequencing, PLoS ONE 6(3):1-7.
Nelson, 1989, Bifunctional oligonucleotide probes synthesized using a novel CPG support are able to detect single base pair mutations, Nucl Acids Res 17(18): 7187-7194.
Nemoto, 1997, In vitro virus: bonding of mRNA bearing puromycin at the 3 terminal end to the C-terminal end of its encoded protein on the ribosome in vitro, Federation of European Biochemical Societies, 414:405-8.
Ness, 2000, Molecular Breeding: the natural approach to protein design. Adv Protein Chem, 55: 261-292.
Ng, 2003, Protein crystallization by capillary counter-diffusion for applied crystallographic structure determination, J. Struct. Biol, 142:218-231.
Ng, 2006, Factors affecting flow karyotype resolution, Cytometry, Part A 69A: 1028-1036.
Nguyen, 2006, Optical detection for droplet size control in microfluidic droplet-based analysis systems, Sensors and Actuators B 117(2):431-436.
Nihant, 1994, Polylactide Microparticles Prepared by Double Emulsion/Evaporation Technique. I. Effect of Primary Emulsion Stability, Pharmaceutical Research, 11(10):1479-1484.
Nisisako, 2002, Droplet formation in a microchannel network, Lab Chip 2:24-26.
Nisisako, 2002, Formation of droplets using branch channels in a microfluidic circuit, Proceedings of the SICE Annual Conference. International Session Papers 1262-1264.
Nisisako, 2005, Controlled formulation of monodisperse double emulsions in a multiple-phase microluidic system, Sot Matter, 1:23-27.
Nisisako, 2008, Microstructured Devices for Preparing Controlled Multiple Emulsions. Chem. Eng. Technol 31(8):1091-1098.
Nof, 2002, Drug-releasing scaffolds fabricated from drug-loaded microspheres, J. Biomed Mater Res 59:349-356.
Norman, 1980, Flow Cytometry, Med. Phys., 7(6):609-615.

(56) References Cited

OTHER PUBLICATIONS

Nygren, 1982, Conjugation of horseradish peroxidase to Fab fragments with different homobifunctional and heterobifunctional cross-linking reagents. A comparative study, J. Histochem. and Cytochem. 30:407-412.
Oberholzer, 1995, Enzymatic RNA replication in self-reproducing vesicles: an approach to a minimal cell, Biochem Biophys Res Commun 207(1):250-7.
Oberholzer, 1995, Polymerase chain reaction in liposomes, Chem. Biol. 2(10):677-82.
Obukowicz, 1988, Secretion and export of IGF-1 in *Escerichia coli* strain JM101, Mol Gen Genet, 215:19-25.
Ogura, 1955, Catalase activity at high concentrations of hydrogen peroxide, Archs Biochem Biophys, 57: 288-300.
Oh, 2002, Distribution of Macropores in Silica Particles Prepared by Using Multiple Emulsions, Journal of Colloid and Interface Science, 254(1): 79-86.
Oh, 2005, Worid-to-chip microfluidic interface with built-in valves for multichamber chip-based PCR assays, Lab Chip, 5, 845-850.
Okuno, 2003, Recent Advances in Optical Switches Using Silica-based PLC Technology, NTT Technical Review 1(7):20-30.
Okushima, 2004, Controlled production of monodisperse double emulsions by two-step droplet breakup in microfluidic devices, Langmuir 20(23): 9905-8.
Olsen, 2000, Function-based isolation of novel enzymes from a large library, Nat Bioteoltnol 13(10):1071-4.
Omburo, 1992, Characterization of the zinc binding site of bacterial phosphotriesterase, J of Biological Chem, 267:13278-83.
Oroskar, 1996, Detection of immobilized amplicons by ELISA-like techniques, Clin. Chem. 42:1547-1555.
Ostermeier, 1999, A combinatorial approach to hybrid enzymes independent of DNA homology, Nat Biotechnol, 17(12):1205-9.
Ott, 1967, Biological and medical research annual report, Los Alamos Scientific Laboratory, 14 pages.
Ouelette, 2003, A new wave of microfluidic devices, Indust Physicist pp. 14-17.
Pabit, 2002, Laminar-Flow Fluid Mixer for Fast Fluorescence Kinetics Studies, Biophys J 83:2872-2878.
Paddison, 2002, Stable suppression of gene expression by RNAi in mammalian cells, PNAS 99(3):1443-1448.
Pain, 1981, Preparation of protein A-peroxidase mono conjugate using a heterobifunctional reagent, and its use in enzyme immunoassays, J Immunol Methods, 40:219-30.
Pannacci, 2008, Equilibrium and Nonequilibrium States in Microluidic Double Emulsions Physical Review Leters, 101(16):164502.
Park, 2001, Model of Formation of Monodispersed Colloids, J. Phys. Chem. B 105:11630-11635.
Park, 2003, Cylindrical compact thermal-cycling device for continuous-flow polymeres chain reaction, Anal Chem, ACS, 75:6029-33.
Parker, 2000, Development of high throughput screening assays using fluorescence polarization: nuclear receptor-ligand-binding and kinase/phosphatase assays, J Biomol Screen, 5(2): 77-88.
Pasternak, 2013, Cell-associated HIV RNA: a dynmic biomarker of viral persistence, Retrovirology 10:41.
Patel, 2003, Formation of Fluorinated Nonionic Surfactant Microemulsions in Hydrfuorocarbon 134a, Journal of Colloid and Interface Science, 258, 345-353.
Pedersen, 1998, A method for directed evolution and functional cloning of enzymes, PNAS 95(18):10523-8.
Pekin, 2011, Quantitative and sensitive detection of rare mutations using droplet-based microfluidics, Lab on a Chip 11(13):2156-2166.
Dormack, 1996, FACS-optimized mutants of the green fluorescent protein (GFP), Gene 173(1):33-38.
Cortesi, 2002, Production of liposheres as carriers for bioactive compounds, Biomateials, 23(11): 2283-2294.
Courrier, 2004, Reverse water-in-fluorocarbon emulsions and microemulsions obtained with a fluorinated surfactant, Colloids and Surfaces A: Physicochem. Eng. Aspects 244:141-148.

Craig, 1995, Fluorescence-based enzymatic assay by capillary electrophoresis laser-induced fluoresence detection for the determinination of a few alpha-galactosidase molecules, Anal. Biochem. 226:147.
Creagh, 1993, Structural and catalytic properties of enzymes in reverse micelles, Enzyme Microb Technol 15(5):383-92.
Crosland-Taylor, 1953, A Device for Counting Small Particles suspended in a Fluid through a Tube, Nature 171:37-38.
Crowley, 1973, Electrical breakdown of bimolecular lipid membranes as an electromechanical instability, Biophys J. 13(7):711-724.
Cull, 1992, Screening for receptor ligands using large libraries of peptides linked to the C terminus of the lac repressor, PNAS 89:1865-9.
Curran, 1998, Strategy-level separations in organic synthesis: from planning to practice. Angew Chem Int Ed, 37:1174-11-96.
Czarnik, 1997, Encoding methods for combinatorial chemistry, CurrOpin Chem Biol 1:60-66.
Dankwardt, 1995, Combinatorial synthesis of small-molecule libraries using 3-amino-5-hydroxybenzoic acid, 1:113-120.
David, 1974, Protein iodination with solid-state lactoperoxidase, Biochemistry 13:1014-1021.
Davis, 1987, Multiple emulsions as targetable delivery systems, Meth Enzymol 149:51-64.
Davis, 2006, Deterministic hydrodynamics: Taking blood apart, PNAS 103:14779-14784.
De Gans, 2004, Inkjet printing of polymers: state of the art and future developments, Advanced materials, 16: 203-213.
De Wildt, 2002, Isolation of receptor-ligand pairs by capture of long-lived multivalent interaction complexes, Proceedings of the National Academy of Sciences of the United States, 99, 8530-8535.
DelRaso, 1993, In vitro methodologies for enhanced toxicity testing, Toxicol. Lett. 68:91-99.
Deng, 2008, Design and analysis of mismatch probes for long oligonucleotide microarrays, BMC Genomics; 9:491, 13 pages.
Dickinson, 1994, Emulsions and droplet size control, Wedlock, D.J., Ed., in Controlled Particle Droplet and Bubble Formulation, ButterWorth-Heine-mann, 191-257.
DiMatteo, 2008, Genetic conversion of an SMN2 gene to SMN1: A novel approach to the treatment of spinal muscular atrophy, Exp Cell Res. 314(4):878-886.
Ding, 2001, Scheduling of microfluidic operations for reconfigurable two-dimensional electrowetting arrays, IEEE Trans CADICS 20(12):1463-1468.
Ding, 2003, Direct molecular haplotyping of long-range genomic DNA with M1-PCR, Proc. Natl. Acad. Sci. USA, 100(33):7449-7453.
Dinsmore, 2002, Colioidosomes: Selectively Permeable Capsules Composed of Colloidal Particles, Science 298(5595):1006-1009.
Dittrich, 2005, A new embedded process for compartmentalized cell-free protein expression and on-line detection in microfluidic devices, Chembiochem 6(5):811-814.
Doi, 1999, STABLE: protein-DNA fusion system for screening of combinatorial protein libraries in vitro, FEBS Lett., 457: 227-230.
Doi, 2004, In vitro selection of restriction endonucleases by in vitro compartmentilization, Nucleic Acids Res, 32(12):e95.
Doman, 2002, Molecular docking and high-throughput screening for novel inhibitors of protein tyrosine phosphatase-1B, J Med Chem, 45: 2213-2221.
Domling, 2000, Multicomponent Reactions with Isocyanides, Angew Chem Int Ed 39(18):3168-3210.
Domling, 2002, Recent advances in isocyanide-based multicomponent chemistry, Curr Opin Chem Biol, 6(3):306-13.
Dorfman, 2005, Contamination-free continuous flow microfluidic polymerase chain reaction for quantitative and clinical applications, Anal Chem 77:3700-3704.
Dove, 2002, Research News Briefs, Nature Biotechnology 20:1213, 1 page.
Dower, 1988, High efficiency transformation of *E. coli* by high voltage electroporation, Nucleic Acids Res 16:6127-6145.
Dressman, 2003, Transforming single DNA molecules into fluorescent magnetic particles for detection and enumeration of genetic variations, PNAS 100:8817-22.

(56) References Cited

OTHER PUBLICATIONS

Dreyfus, 2003, Ordered and disordered patterns in two phase flows in microchannels, Phys Rev Lett 90(14):144505-1-144505-4.
Drmanac, 1992, Sequencing by hybridization: towards an automated sequencing of one million M13 clones arrayed on membranes, Elctrophoresis 13:566-573.
Du, 2009, SlipChip, Lab Chip, 9, 2286-2292.
Dubertret, 2002, In vivo imaging of quantum dots encapsulated in phospholipid micelles, Science, 298: 1759-1762.
Duffy, 1998, Rapid Protyping of Microfluidic Systems and Polydimethylsiloxane, Anal Chem 70:474-480.
Duggleby, 1995, Analysis of Enzyme Progress Curves by Nonlinear Regression, Pt D. Academic Press 249:61-90.
Dumas, 1989, Purification and properties of the phosphotriesterase from Psuedomonas diminuta, J Biol Chem 264:19659-19665.
Eckert, 1991, DNA polymerase fidelity and the polymerase chain reaction, Genome Res 1:17-24.
Ecole Polytech Federate de Lausanne, 2014, Tracing water channels in cell surface receptors, PhysOrg News (2 pages).
Edel, 2002, Microfluidic Routes to the Controlled Production of Nanopaticles, Chemical Communications, 1136-1137.
Edris, 2001, Encapsulation of orange oil in a spray dried double emulsion, Nahrung/Food, 45(2):133-137.
Effenhauser, 1993, Glass chips for high-speed capillary electrophoresis separations with submicrometer plate heights, Anal Chem 65:2637-2642.
Eggers, 1999, Coalescence of Liquid Drops, J Fluid Mech 401:293-310.
Ehrig, 1995, Green-fluorescent protein mutants with altered fluorescence excitation spectra, Febs Lett, 367(2):163-66.
Eigen, 1980, Hypercycles and compartments: compartments assists—but does not replace—hypercyclic organization of early genetic information, J Theor Biol, 85:407-11.
Elghanian, 1997, Selective colorimetric detection of polynucleotides based on the distance-dependent optical properties of gold nanoparticles, Science, 277(5329):1078-1080.
Ellington, 1990, In vitro selection of RNA molecules that bind specific ligands, Nature, 346:818-822.
Branebjerg, 1996, Fast mixing by lamination, MEMS Proc 9th Ann 9:441-446.
Braslavsky, 2003, Sequence information can be obtained from single DNA molecules, PNAS 100(7):13960-3964.
Breslauer, 2006, Microfluidics based systems biology, Mol Bio Syst 2:97-112.
Bringer, 2004, Microfluidic systems for chemical kinetics that rely on chaotic mixing in droplets, Phil Trans A Math Phys Eng Sci 362:1-18.
Brown, 1979, Chemical synthesis and cloning of a tyrosine tRNA gene, Methods Enzymol 68:109-151.
Bru, 1991, Product inhibition of alpha-chymotrypsin in reverse micelles. Eur J Biochem 199(1):95-103.
Bru, 1993, Catalytic activity of elastase in reverse micelles, Biochem Mol Bio Int, 31(4):685-92.
Brummelkamp, 2002, A system for stable expression of short interfering RNAs in mammalian cells, Science 296(5567):550-3.
Buican, 1987, Automated single-cell manipulation and sorting by light trapping, Appl Optics 26(24):5311-5316.
Burbaum, 1998, Miniaturization technologies in HTS, Drug Disc Today 3:313-322.
Burns, 1996, Microfabricated structures for integrated DNA analysis, PNAS 93:5556-5561.
Burns, 1998, An integrated nanoliter DNA analysis device, Science 282:484-487.
Burns, 2002, The intensification of rapid reactions in multiphase systems using slug flow in capillaries, Lab on a Chip 1:10-15.
Byrnes, 1982, Sensitive fluorogenic substrates for the detection of trypsin-like proteases and pancreatic elastase, Anal Biochem 126:447.
Cahill, 1991, Polymerase chain reaction and Q beta replicase amplification, Clin Chem 37(9):1482-5.
Caldwell, 1991, Limits of diffusion in the hydrolysis of substrates by the phosphodiesterase from Pseudomonas diminuta, Biochem 30:7438-7444.
Calvert, 2001, Inkjet printing for materials and devices, Chem Mater 13:3299-3305.
Caruccio, 2009, Nextura technology for NGS DNA library preparation: simulaneous fragmentation and tagging by in vitro transposition, Epibio Newsletter.
Caruthers, 1985, Gene synthesis machines: DNA chemistry and its uses, Science 230:281-285.
Cavalli, 2010, Nanosponge formulations as oxygen delivery systems, Int J Pharmaceutics 402:254-257.
Chakrabarti, 1994, Production of RNA by a polymerase protein encapsulated within phospholipid vesicles, J Mol Evol 39(6):555-9.
Chamberlain, 1973, Characterization of T7-specific ribonucleic acid polymerase. 1. General properties of the enzymatic reaction and the template specificity of the enzyme, J Biol Chem 248:2235-44.
Chan, 2003, Size-Controlled Growth of CdSe Nanocrystals in Microfluidic Reactors, Nano Lett 3(2):199-201.
Chan, 2008, New trends in immunoassays, Adv Biochem Engin/Biotech 109:123-154.
Chang, 1987, Recycling of NAD(P) by multienzyme systems immobilized by microencapsulation in artifical cells, Methods Enzymol, 136(67):67-82.
Chang, 2008, Controlled double emulsification utilizing 3D PDMS microchannels, Journal of Micromechanics and Microengineering 18:1-8.
Chao, 2004, Control of Concentration and Volume Gradients in Microfluidic Droplet Arrays for Protein Crystallization Screening, 26th Annual International Conference of the IEEE Engineering in Medicine and Biology Society, San Francisco, California Sep. 1-5.
Chao, 2004, Droplet Arrays in Microfluidic Channels for Combinatorial Screening Assays, Hilton Head: A Solid State Sensor, Actuator and Microsystems Workshop, Hilton Head Island, South Carolina, Jun. 6-10.
Chapman, 1994, In vitro selection of catalytic RNAs, Curr. op. Struct. Biol., 4:618-22.
Chayen, 1999, Crystallization with oils: a new dimension in macromolecular crystal growth Journal of Crystal Growth, 196:434-441.
Chen, 2001, Capturing a Photoexcited Molecular Structure Through Time-Domain X-ray Absorption Fine Structure, Science 292(5515):262-264.
Chen, 2003, Microfluidic Switch for Embryo and Cell Sorting The 12th International Conference on Solid State Sensors, Actuators, and Microsystems, Boston, MA, Transducers, 1: 659-662.
Chen-Goodspeed, 2001, Enhancement, relaxation, and reversal of the stereoselectivity for phosphotriesterase by rational evolution of active site residues, Biochemistry, 40: 1332-1339.
Chen-Goodspeed, 2001, Structural Determinants of the substrate and stereochemical specificity of phosphotriesterase, Biochemistry, 40(5):1325-31.
Cheng, 2003, Electro flow focusing inmicrofluidic devices, Microfluidics Poster, presented at DBAS, Frontiers in Nanoscience, 1 page.
Cheng, 2006, Nanotechnologies for biomolecular detection and medical diagnostics, Current Opinion in Chemical Biology, 10:11-19.
Chetverin, 1995, Replicable RNA vectors: prospects for cell-free gene amplification, expression, and cloning, Prog Nucleic Acid Res Mol Biol, 51:225-70.
Chiang, 1993, Expression and purification of general transcription factors by FLAG epitope-tagging and peptide elution, Pept Res, 6:62-64.
Chiba, 1997, Controlled protein delivery from biodegradable tyrosino-containing poly(anhydride-co-imide) microspheres, Biomaterials, 18(13):893-901.
Chiou, 2001, A closed-cycle capillary polymerase chain reaction machine, Analytical Chemistry, American Chamical Society, 73:2018-21.
Chiu, 1999, Chemical transformations in individual ultrasmall biomimetic containers, Science, 283:1892-1895.
Chou, 1998, A microfabricated device for sizing and sorting DNA molecules 96:11-13.

(56) References Cited

OTHER PUBLICATIONS

Clackson, 1994, In vitro selection from protein and peptide libraries, Trends Biotechnol, 12:173-84.
Clausell-Tormos, 2008, Droplet-based microfluidic platforms for the encapsulation and screening of Mammalian cells and multicellular organisms, Chem Biol 15(5):427-437.
Cohen, 1991, Controlled delivery systems for proteins based on poly(lactic/glycolic acid) microspheres, Pharm Res, 8(6):713-720.
Collins, 2003, Optimization of Shear Driven Droplet Generation in a Microluidic Device, ASME International Mechanical Engineering Congress and R&D Expo, Washington, 4 pages.
Collins, 2004, Microfluidic flow transducer based on the measurements of elecliical admittance, Lab on a Chip, 4:7-10.
Compton, 1991, Nucleic acid sequence-based amplification, Nature, 350(6313):91-2.
Cook, 2007, Use and misuse of receiver operating characteristic curve in risk prediction, Circulation 115(7):928-35.
Cooper, 2000, The Central Role of Enzymes as Biological Catalysts, The Cell: A Molecular Approach, 2nd Edition, pp. 1-6.
Xu, 2009, Design of 240, 000 orthogonal 25mer DNA barcode probes, PNAS, 106(7) p. 2289-2294.
Yamagishi, 1990, Mutational analysis of structure-activity relationships in human tumor necrosis factor-alpha, Protein Eng, 3:713-9.
Yamaguchi, 2002, Insulin-loaded biodegradable PLGA microcapsules: initial burst release controlled by hydrophilic additives, Journal of Controlled Release, 81(3): 235-249.
Yelamos, 1995, Targeting of non-lg sequences in place of the V segment by somatic hypermutation. Nature 376(6537):225-9.
Yershov, 1996, DNA analysis and diagnostics on oligonucleotide microchips, PNAS 93(10):4913-4918.
Yonezawa, 2003, DNA display for in vitro selection of diverse peptide libraries, Nucleic Acids Research, 31(19): e118, 5 pages.
Yu, 1997, Specific inhibition of PCR by non-extendable oligonucleotides using a 5' to 3' exonuclease-deficient DNA polymerase, Biotechniques 23(4):714-6, 718-20.
Yu, 2001, Responsive biomimetic hydrogel valve for microfluidics. Appl. Phys. Lett 78:2589-2591.
Yu, 2002, Environmental Carcinogenic Polycyclic Aromatic Hydrocarbons: Photochemisrty and Phototoxicity, J Environ Scie Health C Environ Carcinog Exotoxicol Rev, 20(2), 1-43.
Yu, 2007, Quantum dot and silica nanoparticle doped polymer optical fibers, Optics Express 15(16):9989-9994.
Zaccolo, 1996, An approach to random mutagenesis of DNA using mixtures of triphosphate derivatives of nucleoside analogues. J Mol Biol 255(4):589-603.
Zakrzewski, 1980, Preparation of tritiated dihydrofolic acid of high specific activity, Methods Enzymol, 529-533.
Zaug, 1986, The intervening sequence RNA of Tetrahymena is an enzyme, Science 231(4737):470-5.
Zaug, 1986, The Tetrahymena intervening sequence ribonucleic acid enzyme is a phosphotransferase and an acid phosphatase, Biochemistry 25(16):4478-82.
Zaug, 1986, The Tetrahymena ribozyme acts like an RNA restriction endonuclease, Nature 324(6096):429-33.
Zhang, 1993, Substrate specificity of the protein tyrosine phosphatases, PNAS 90: 4446-4450.
Zhang, 1999, A Simple Statistical Parameter for Use in Evaluation and Validation of High Throughput Screening Assays, Journal of Biomolecular Screening, 4(2): 67-73.
Zhao, 1998, Molecular evolution by staggered extension process (StEP) in vitro recombination. Nat Biotechnol 16(3):258-61.
Zhao, 2002, Control and Applications of Immiscible Liquids in Microchannels, J. Am. Chem. Soc, vol. 124:5284-5285.
Zheng, 2003, Screening of Protein Crystallization Conditions on a Microfluidic Chip Using Nanoliter-Size Droplets, J Am Chem Soc 125(37):11170-11171.
Zheng, 2004, A Droplet-Based, Composite PDMS/Glass Capillary Microfluidic System for Evaluating Protein Crystallization Conditions by Microbatch and Vapor-Diffusion Methods with On-Chip X-Ray Diffraction, Angew. Chem., 116:1-4.
Zheng, 2004, Formation of Droplets of Alternating Composition in Microfluidic Channels and Applications to Indexing of Concentrations in Droplet-Based /Assays, Anal. Chem.,76: 4977-4982.
Zheng, 2005, A Microiuidic Approach for Screening Submicroliter Volumes against Multiple Reagents by Using Performed Arrays of Nanoliter Plugs in a Three-Phase Liquid/Liquid/Gas Flow, Angew. Chem. Int. Ed., 44(17):2520-2523.
Zhong, 2011, Multiplex digital PCR: breaking the one target per color barrier of quantitative PCR, Lab on a Chip 11(13):2167-2174.
Zimmermann, 1974, Dielectric Breakdown of Cell Membranes, Biophys J 14(11):881-889.
Zimmermann, 1992, Microscale Production of Hybridomas by Hypo-Osmolar Electrofusion, Hum. Antibod. Hybridomas, 3(1): 14-18.
Zimmermann, 2008, Digital PCR: a powerful new tool for noninvasive prenatal diagnosis?, Prenat Diagn 28, 1087-1093.
Zubay, 1973, In vitro synthesis of protein in microbial systems, Annu Rev Genet, 7: 267-87.
Zubay, 1980, The isolation and properties of CAP, the catabolite gene activator, Methods Enzymol, 65: 856-77.
Zuckermann, 1987, Efficient Methods for Attachment of Thiol-Specific Probes to the 3-end of Synthetic Oligodeoxyribonucleotides, Nucleic Acids Res. 15:5305-5321.
Schatz, 1996, Screening of peptide libraries linked to lac repressor, Meth Enzymol 267:171-91.
Schneegass, 2001, Miniaturized flow-through PCR with different template types in a silicone chip thermocycler, Lab on a Chip 1:42-9.
Schopman, 2012, Selective packaging of cellular miRNAs in HIV-1 particles, Virus Res 169(2):438-47.
Schubert, 2002, Designer Capsules, Nat Med 8:1362.
Schweitzer, 2000, Immunoassays with rolling circle DNA amplification, PNAS 97(18):10113-10119.
Schweitzer, 2001, Combining nucleic acid amplification and detection. Curr Opin Biotechnol 12(1):21-7.
Scott, 1948, The solubility of fluorocarbons, J Am Chem Soc 70:4090-4093.
Sedlak, 2013, Viral diagnostics in the era of digital polymerase chain reaction, Diag Microb Inf Dis 75(1):1-4.
Seethala, 1997, Homogeneous fluorescence polarization assay for Src-Family tyrosine kinases, Anal Biochem 253(2):210-218.
Seiler, 1993, Planar glass chips for capillary electrophoresis: repetitive sample injection, quantitation, and separation efficiency. Anal Chem 65(10):1481-1488.
Selwyn, 1965, A simple test for inactivation of an enzyme during assay, Biochim Biophys Acta 105:193-195.
Seo, 2007, Microfluidic consecutive flow-focusing droplet generators, Soft Matter 3:986-992.
Seong, 2002, Efficient mixing and reactions within microfluidic channels using microbead-supported catalysts, J Am Chem Soc 124(45):13360-1.
Seong, 2002, Fabrication of microchambers defined by photopolymerized hydrogels and weirs within microfluidic systems, Anal Chem 74(14):3372-3377.
Sepp, 2002, Microbead display by in vitro compartmentalisation: selection for binding using flow cytometry, FEBS Letters 532:455-58.
Serpersu, 1985, Reversible and irreversible modification of erythrocyte membrane permeability by electric field, Biochim Biophys Acta 812(3):779-785.
Shapiro, 1983, Multistation multiparameter flow cytometry: a critical review and rationale, Cytometry 3: 227-243.
Shastry, 2006, Directing droplets using microstructured surfaces, Langmuir 22:6161-6167.
Shen, 2006, Eigengene-based linear discriminant model for tumor classification using gene expression microarray data, Bioinformatics 22(21):2635-2642.
Shestopalov, 2004, Multi-step synthesis of nanoparticles performed on millisecond time scale in a microfluidic droplet-based system, Royal Soc Chem 4:316-321.
Shim, 2007, Using microfluidics to decouple nucleation and growth of protein crystals, Cryst Growth Des 7(11):2192-2194.

(56) References Cited

OTHER PUBLICATIONS

Shimizu, 1995, Encapsulation of biologically active proteins in a multiple emulsion, Biosci Biotech Biochem 59(3):492-496.
Shtern, 1996, Hysteresis in swirling jets, J Fluid Mech 309:1-44.
Sia, 2003, Microfluidic devices fabricated in poly(dimethylsiloxane) for biological studies, Electrophoresis 24(21):3563-3576.
Siemering, 1996, Mutations that suppress the thermosensitivity of green fluorescent protein, Curr Biol 6:1653-1663.
Silva-Cunha, 1998, W/O/W multiple emulsions of insulin containing a protease inhibitor and an absorption enhancer: biological activity after oral administration to normal and diabetic rats, Int J Pharm 169:33-44.
Sims, 2000, Immunopolymerase chain reaction using real-time polymerase chain reaction for detection, Anal. Biochem. 281(2):230-2.
Sista, 2007, Development of a Digital Microfluidic Lab-on-a-Chip for Automated Immunoassay with Magnetically Responsive Beads, Doctoral Thesis, Florida State University, 128 pages.
Sista, 2008, Development of a digital microfluidic platform for point care testing, Lab on a Chip 8:2091-2104.
Siwy, 2003, Electro-responsive asymmetric nanopores in polyimide with stable ion-current signal, Appl Phys A: Mat Sci Proc 76:781-785.
Slappendel, 1994, Normal cations and abnormal membrane lipids in the red blood cells of dogs with familial stomatocytosis hypertrophic gastritis, Blood 84:904-909.
Slob, 1997, Structural identifiability of PBPK models: practical consequences for modeling strategies and study designs, Crit Rev Toxicol. 27(3):261-72.
Smith, 1985, The synthesis of oligonucleotides containing an aliphatic amino group at the 5' terminus: synthesis of fluorescent DNA primers for use in DNA sequence analysis, Nucl Acid Res 13:2399-2412.
Smith, 1986, Fluorescence detection in automated DNA sequence analysis, Nature 321:674-679.
Smith, 1989, Absolute displacement measurements using modulation of the spectrum of white light in a Michelson interferometer, Applied Optics, 28(16):3339-3342.
Smith, 1992, Direct mechanical measurements of the elasticity of single DNA molecules by using magnetic beads, Science 258(5085):1122-1126.
Smith, 2010, Highly-multiplexed barcode sequencing: an efficient method for parallel analysis of pooled samples, Nucleic Acids Res 38(13):e142.
Smyth, 2000, Markers of apoptosis: methods for elucidating the mechanism of apoptotic cell death from the nervous system, Biotechniques 32:648-665.
Sohn, 2000, Capacitance cytometry: Measuring biological cells one by one, PNAS 97(20):10687-10690.
Sola, 2014, Fabrication of a microfluidic cell made of thiolene for microarray applications, 18th Int Conf Miniaturized Systems for Chem and Life Sciences, MicroTAS, San Antonio, TX 1719-1721.
Somasundaram, 1999, Gain studies of Rhodamine 6G dye doped polymer laser, J Photochem Photobiol 125(1-3):93-98.
Song, 2002, Experimental test of scaling of mixing by chaotic advection in droplets moving through microfluidic channels, App Phy Lett 83(22):4664-4666.
Song, 2003, A microfluidic system for controlling reaction networks in time, Angew Chem Int Ed 42(7):768-772.
Song, 2003, Millisecond kinetics on a microluidic chip using nanoliters of reagents, J Am Chem Soc 125:14613-14619.
Song, 2006, Reactions in droplets in microfluidic channels, Angew chem Int ed 45(44):7336-7356.
Soni, 2007, Progress toward ultrafast DNA sequencing using solid-state nanopores, Clin Chem 53:1996-2001.
Soumillion, 2001, Novel concepts for the selection of catalytic activity. Curr Op Biotech 12:387-394.
Spiro, 2000, A bead-based method for multiplexed identification and quantitation of DNA sequences using flow cytometry, Appl Env Micro 66:4258-4265.
Sproat, 1987, The synthesis of protected 5'-mercapto-2',5'-dideoxyribonucleoside-3'-0-phosphorainidites, uses of 5'-mercapto-oligodeoxyribonucleotides, Nucleic Acids Res 15:4837-4848.
Squires, 2005, Microfluidics: fluid physics at the nanoliter scale, Rev Mod Phys 77:977-1026.
Giusti, 1993, Synthesis and characterization of 5' fluorescent dye labeled oligonucleotides, Genome Res 2:223-227.
Glass, 1995, Development of primer sets designed for use with the PCR to amlify conserved genes from filamentous ascomycetes. Applied and Environmental Microbiology, vol. 6, pp. 1323-1330.
Gold, 1995, Diversity of Oligonucleotide Functions Annu Rev Biochem, 64: 763-97.
Gong, 2015, Simple method to prepare oligonucleotide conjugated antibodies and its applicaiotn in multiplex protein detection in single cells, Bioconjugate Chm 27(1):271-225.
Goodall, 1998, Operation of Mixed-Culture Immobilized Cell Reactors for the Metabolism of Meta- and Para-Nitrobenzoate by *Comamonas* Sp. JS46 and *Comamonas* Sp. JS47, Biotechnology and Bioengineering, 59 (1): 21-27.
Gordon, 1999, Solid phase synthesis—designer linkers for combinatorial chemistry: a review, J. Chem. Technol. Biotechnol., 74(9):835-851.
Grasland-Mongrain, 2003, Droplet coalescence in microfluidic devices, 30 pages, From internet: http://www.eleves.ens.fr/home/grasland/rapports/stage4.pdf.
Gray, 1987, High speed crhomosome sorting, Science 238(4825):323-329.
Green, 1992, Selection of a Ribozyme That Functions as a Superior Template in a Self Copying Reaction, Science, 258: 1910-5.
Gregoriadis, 1976, Enzyme entrapment in liposomes, Methods Enzymol 44:218-227.
Griffiths, 2000, Man-made enzymes-from design to in vitro compartmentalisation, Curr Opin Biotechnol 11:338-353.
Griffiths, 2003, Directed evolution of an extremely fast phosphotriesterase by in vitro compartmentalization, EMBO J, 22:24-25.
Griffiths, 2006, Miniaturising the laboratory in emulsion droplets, Trend Biotech 24(9):395-402.
Grinwood, 2004, The DNA sequence and biology of human chromosome 19, Nature 428:529-535.
Grothues, 1993, PCR amplification of megabase DNA with tagged random primers (T-PCR), Nucl. Acids Res vol. 21(5):1321-1322.
Grund, 2010, Analysis of biomarker data:logs, odds, ratios and ROC curves, Curr Opin HIV AIDS 5(6):473-479.
Guatelli, 1990, Isothermal, in vitro amplification of nucleic acids by a multienzyme reaction modeled after retroviral replication, PNAS, 87(5):1874-8.
Guixe, 1998, Ligand-Induced Conformational Transitions in *Escherichia coli* Phosphofructokinase 2: Evidence for an Allosteric Site for MgATP2n, Biochem., 37: 13269-12375.
Gupta, 1991, A general method for the synthesis of 3'-sulfhydryl and phosphate group containing oligonucleotides, Nucl Acids Res 19 (11): 3019-3026.
Haber, 1993, Activity and spectroscopic properties of bovine liver catalase in sodium bis(2-ethylhexyl) sulfosuccinate/isooctane reverse micelles, Eur J Biochem 217(2): 567-73.
Habig, 1981, Assays for differentiation of glutathione S-transferases, Methods in Enzymology, 77: 398-405.
Hadd, 1997, Microchip Device for Performing Enzyme Assays, Anal. Chem 69(17): 3407-3412.
Haeberle, 2007, Microfluidic platforms for lab-on-a-chip applications, Lab on a Chip 7:1081-1220.
Hagar, 1992, The effect of endotoxemia on concanavalin A induced alterations in cytoplasmic free calcium in rat spleen cells as deter-mined with Fluo-3, Cell Calcium 13:123-130.
Hai, 2004, Investigation on the release of fluorescent markers from the w/o/w emulsions by fluorescence-activated cell sorter, J Control Release, 96(3): 393-402.
Haies, 1981, Morphometric study of rat lung cells. I. Numerical and dimensional characteristics of parenchymal cell population, Am. Rev. Respir. Dis. 123:533-54.

(56) References Cited

OTHER PUBLICATIONS

Hall, 2003, The EBG system of *E. coli*: origin and evolution of a novel beta-galactosidase for the metabolism of lactose, Genetica 118(2-3):143-56.
Hamady, 2008, Error-correcting barcoded primers for pyrosequencing hundreds of samples in multiplex. Nature Nethods vol. 5, No. 3, p. 235-237.
Han, 2001, Quantum-dot-tagged Microbeads for Multiplexed Optical Coding of Biomolecules, Nat Biotech 19(7):631-635.
Handen, 2002, High-throughput screening—challenges for the future, Drug Discov World, 47-50.
Handique, 2001, On-Chip Thermopneumatic Pressure for Discrete Drop Pumping, Analytical Chemistry, 73:1831-1838.
Hanes, 1997, In vitro selection and evolution of functional proteins by using ribosome display, PNAS 94:4937-42.
Hanes, 1998, Degradation of porous poly(anhydide-co-imide) microspheres and implication for controlled macromolecule delivery, Biomaterials, 19(1-3): 163-172.
Hansen, 2002, A robust and scalable microfluidic metering method that allows protein crystal growth by free interface diffusion, PNAS 99(26):16531-16536.
Harada, 1993, Monoclonal antibody G6K12 specific for membrane-associated differentiation marker of human stratified squamous epithelia and squamous cell carcinoma, J. Oral Pathol. Med 22(4):145-152.
Harder, 1994, Characterization and kinetic analysis of the intracellular domain of human protein tyrosine phosphatase beta (HPTP beta) using synthetic phosphopeptides, Biochem J 298 (Pt 2): 395-401.
Harries, 2006, A Numerical Model for Segmented Flow in a Microreactor, Int J of Heat and Mass Transfer, 46:3313-3322.
Harris, 2008, Single-molecule DNA sequencing of a viral genome, Science 320(5872):106-109.
Harrison, 1993, Micromachining a miniaturized capillary electrophoresis-based chemical analysis system on a chip, Science 261(5123):895-897.
Hasina, 2003, Plasminogen activator inhibitor-2: a molecular biomarker for head and neck cancer progression, Cancer Research 63:555-559.
Haynes, 2012, Digital PCR: A Technology Primer, Principles of Digital PCR and Measurement Issues: The certification of Cytomegalovirus Standard Reference Material (SRM 2366) as a model for future SRMs, National Institute of Standards and Tecnology, San Diego, CA, 4 pages.
Hayward, 2006, Dewetting Instability during the Formation of Polymersomes from BloceCopolymer-Stabilized Double Emulsions, Langmuir, 22(10): 4457-4461.
He, 2005, Selective encapsulation of single cells and subcellular organelles into picoliter- and femtoliter-volume droplets, Anal Chem 77(6):1539-1544.
Head, 2014, Library construction for next generation sequencing, Biotech Rap Disp 56(2):61.
Heim, 1996, Engineering Green Fluorescent Protein for Improved Brightness, Longer Wavelengths and Fluorescence Response Energy Transfer, Carr. Biol, 6(2): 178-182.
Hellman, 2009, Differential tissue-specific protein markers of vaginal carcinoma, Br J Cancer, 100(8): 1303-131.
Henrich, 2012, Low-level detection and quantitation of cellular HIV-1 DNA and 2-ILTR circles using droplet dPCR, J Virol Meth 186(1-2):68-72.
Hergenrother, 2000, Small-Molecule Microarrays: Covalent Attachment and Screening of Alcohol-Containing Small Molecules on Glass Slides, J. Am. Chem. Soc, 122: 7849-7850.
Hermankova, 2003, Analysis of human immunodeficiency virus type 1 gene expression in lately infected reseting CD4 T lymphocytes in vivo, J Virology 77(13):7383-7392.
Herzer, 2001, DNA Purification, in Molecular Biology Problem Solver: A Laboratory Guide, Edited by Alan S. Gerstein, Ch 1.
Laird, 2013, Rapid Quantification of the Latent Reservoir for HIV-1 Using a Viral Outgrowth Assay, PLOS Pathogens 9(5):e1003398.

Lamprecht, 2004, pH-sensitive microsphere delivery increases oral bioavailability of calcitonin, J Control Rel 98(1):1-9.
Lancet, 1993, Probability model for molecular recognition in biological receptor repertoirs, PNAS 90(8):13715-9.
Landergren, 1988, A ligase mediated gene detection technique, Science 241(4869):1077-80.
Lasheras, 1998, Breakup and atomization of a round waterjet by a high speed annular air jet, J Fluid Mech 357:351-379.
Laufer, 1996, Introduction to Optics and Lasers in Engineering, Cambridge University Press, Cambridge UK:156-162.
Leamon, 2003, A massively parallel pictoterplate based platform for discrete picoliter-scale PCR, Electrophoresis 24:3769-3777.
Leary, 2000, Application of advanced cytometric and molecular technologies to minimal residual disease monitoring, Proc SPIE 3913:36-44.
Lee, 2000, Circulating flows inside a drop under time-periodic non-uniform electric fields, Phys Fuilds 12(8):1899-1910.
Lee, 2001, Preparation of silica particles encapsulating retinol using O/W/O multiple emulsions, J Coll Interface Sci 240(1):83-89.
Lee, 2002, Effective formation of silicone-in-fluorocarbon-in-water double emulsions, J Disp Sci Tech 23(4):491-497.
Lee, 2002, Investigating the target recognition of DNA cytosine-5 methyltransferase Hhal by library selection using in vitro compartmentalisation (IVC), Nucleic Acids Res 30:4937-4944.
Lee, 2004, Special issue on biomedical applications for MEMS and microfluidics, Proc IEEE 92(1):3-5.
Lemof, 2003, An AC magnetohydrodynamic microfluidic switch for Micro Total Analysis Systems, Biomed Microdev 5(I):55-60.
Leng 2009, Microfluidic crystalizaiton,Lab Chip 9:24-23.
Leng, 2010, Agarose droplet microfluidics for highly parallel and efficient single molecule emulsion PCR, Lab Chip 10:2841-2843.
Lesley, 1991, Use of in vitro protein synthesis from PCR-generated templates to study interaction of *E coli* transcription factors with core RNA polymerase, J Biol Chem 266(4):2632-8.
Lesley, 1995, Preparation and use of *E. coli* S-30 extracts, Methods Mol Biol 37:265-78.
Leung, 1989, A method for random mutagenesis of a defined DNA segment using a modified polymerase chain reaction, Technique 1:11-15.
Li, 1995, Single-step procedure for labeling DNA strand breaks with fllourescein-or BODIPY-conjugated deoxynucleotides, Cytometry 20:172-180.
Li, 1997, Transport, manipulation, and reaction of biological cells on-chip using electrokinetic effects, Anal Chem 69(8):1564-1568.
Li, 2005, Multiplexed detection of pathogen DNA with DNA-based fluorescence nanobarcodes, Nat Biotech 23(7):885-889.
Li, 2006, Nanoliter microfluidic hybrid method for simultaneous screening and optimization validated with crystallization of membrane proteins, PNAS 103:19243-19248.
Li, 2018, Microfluidic fabrication of microparticles for biomedical applications, Chem Soc Rev 47(15):5646-5683.
Liao, 1986, Isolation of a thermostable enzyme variant by cloning and selection in a thermophile, PNAS 83:576-80.
Lim, 1980, Microencapsulated islets as bioartificial endocrine pancreas, Science 210(4472):908-10.
Lin, 2007, Self-assembled combinatorial encoding nanoarrays for multiplexed biosensing, Nano Lett 7(2):507-512.
Link, 2004, Geometrically mediated breakup of drops in microfluidic devices, Phys Rev Lettv92(5):054503-1-4.
Link, 2006, Electric control droplets in microfluidic devices, Angew Chem Int Ed 45:2556-2560.
Lipinski, 2001, Experimental and computational approaches to estimate solubility and permeability in drug discovery, , Adv Drug Deliv Rev 46:3-26.
Lipkin, 1988, Biomarkers of increased susceptibility to gastreointestinal cancer: new application to studies of cancer prevention in human subjects, Cancer Res 48:235-245.
Liu, 2000, Passive mixing in a three-dimensional serpentine microchannel, J MEMS 9(2):190-197.
Liu, 2002, Fabrication and characterization of hydrogel-based microvalves, Mecoelectromech. Syst.11:45-53.

(56) References Cited

OTHER PUBLICATIONS

Lizardi, 1998, Mutation detection and single-molecule counting using isothermal rolling-circle amplification. Nat Genet 19(3):225-32.

Lo, 2007, Digital PCR for the molecular detection of fetal chromosomal aneuploidy, PNAS 104(32):13116-13121.

Loakes, 1994, 5-Nitroindole as a universal base analogue, Nucleic Acids Res 22:4039-4043.

Loakes, 1997, Stability and structure of DNA oligonucleotides containing non-specific base analogues, J Mol Biol 270:426-435.

Lodish, 2000, Structure of Nucleic Acids, Section 4.1 , Molecular Cell Biology, 4th edition, New York, 1-3.

Loeker, 2003, FTIR analysis of water in supercritical carbon dioxide microemulsions using monofunctional perfluoropolyether surfanctants, Colloids and Surfaces A: Phys Eng Asp 214:143-150.

Loo, 2004, Nanoshell Enabled Photonics-Based Imaging and Therapy of Cancer, Technology in Cancer Research & Treatment 3(1):33-40.

Lopez-Herrera, 1995, The electrospraying of viscous and non-viscous semi-insulating liquids: scaling laws, Bull Am Phys Soc 40 (12):2041.

Lopez-Herrera, 1999, One-dimensional simulation of the breakup of capillary jets of conducting liquids application to EHD spraying, Aerosol Set 30(7):895-912.

Lopez-Herrera, 2003, Coaxial jets generated from electrified Taylor cones, Aerosol Sci 34:535-552.

Lorenceau, 2005, Generation of polymerosomes from double-emulsions, Langmuir 21(20):9183-9186.

Lorenz, 1991, Isolation and expression of a cDNA encoding Renilla reniformis luciferase, PNAS 88(10):4438-42.

Loscertales, 2002, Micro/nano encapsulation via electrified coaxial liquid jets, Science 295(5560):1695-1698.

Lowe, 2002, Perfluorochemical respiratory gas carriers: benefits to cell culture systems, J Fluorine Chem 118:19-26.

Lu, 2007, Robust fluorescein-doped silica nanoparticles via dense-liquid treatment, Colloids and Surfaces A Phys Eng Asp 303(3):207-210.

Luisi, 1987, Activity and conformation of enzymes in reverse micellar solutions, Meth Enzymol 136:188-216.

Lund, 1988, Assesment of methods for covalent binding of nucleic acids to magnetic beads, Dynabeads, and the characteristics of the bound nucleic acids in hybridization reactions, Nucleic Acids Res 16(22):10861-10880.

\* cited by examiner

Single Target

Complex

Complex

Modified Analytes (e.g. Post Translational-PTM)

Protein:Nucleic Acid Complex

RNA Full length

RNA Splice variant

DNA

DNA
Gene fusion

Methyl or 3-OH Methyl DNA

```
                              SEQUENCE LISTING

<160> NUMBER OF SEQ ID NOS: 10

<210> SEQ ID NO 1
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1
tcgttcgagt cataa                                                          15

<210> SEQ ID NO 2
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 2
tcgttcgagt gataa                                                          15

<210> SEQ ID NO 3
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 3
tagttcagtc cgtc                                                           14

<210> SEQ ID NO 4
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 4
tctggatcca cgggacgttg actgcatt                                            28

<210> SEQ ID NO 5
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 5
agacctaggt gccctgcaac tgacgtaa                                            28

<210> SEQ ID NO 6
<211> LENGTH: 22
<212> TYPE: DNA
<213> ORGANISM: Artificial Sequence
<220> FEATURE:
<223> OTHER INFORMATION: Synthetic Sequence
```

```
<400> SEQUENCE: 6
tctggatcca cgggacggcc ac                                              22

<210> SEQ ID NO 7
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 7
tgacgactgc att                                                        13

<210> SEQ ID NO 8
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 8
agacctaggc ggtgactgct g                                               21

<210> SEQ ID NO 9
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 9
tctggatccg ccactgacga ctgcatt                                         27

<210> SEQ ID NO 10
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 10
gatccacggg acgtgacgac tgcatt                                          26
```

SANDWICH ASSAYS IN DROPLETS

FIELD OF THE INVENTION

The invention generally relates to performing sandwich assays, advantageously in droplets.

BACKGROUND

Biomarkers are commonly used to monitor and diagnosis disease. Biomarkers include nucleic acids, proteins, or other biological molecules. Typically, an assay to identify a disease-associated biomarker is conducted in biological media, such as human tissues, cells or fluids, and may be used to identify pathological processes before individuals become symptomatic or to identify individuals who are susceptible to diseases or already show signs and symptoms of a disease.

Standard screening assays have been developed that can detect bacteria or viruses. Similarly, standard screening assays have been developed that can use biomarkers to assess the health status of a patient and to provide insight into the patient's risk of having a particular disease or disorder. An exemplary class of screening assays are sandwich assay. In a sandwich assay, a first binding agent with specificity for a target analyte (e.g., a bacteria, virus, or biomarker) is bound to a solid support. A sample is introduced to the solid support such that target analyte in the sample binds the first binding agent, thus becoming immobilized to the solid support. Then, a second binding agent with specificity for a target analyte is introduced to the and allowed to bind to the immobilized target analyte. The assay is named a sandwich assay because the first and second binding agents now sandwich the target analyte. A wash step is performed to remove unbound components of the sample and any excess binding agents. The second binding agent typically includes a detectable label, and the label on the second binding agent is then detected, thus detecting the target analyte in the sample. Sandwich assays are typically antibody based and a commonly used sandwich assay is an enzyme-linked immunosorbent assay (ELISA).

A problem with sandwich assays, particularly antibody based sandwich assays, is that they are unable to scale to high-level multiplexing. Issues of antibody cross-reactivity and non-specific adsorption occur when assays are multiplexed in the same tube. The ability to multiplex samples, i.e., pool different patient samples, is important for decreasing costs and increasing the through-put of analysis platforms. Additionally, assay development requires significant effort to optimize reagents to retain similar sensitivity as in single-plex assays. Further, such assays are not practical for use with small sample amounts collected at clinics.

SUMMARY

The invention utilizes microfluidics and droplet technology in combination with sandwich assays. Methods of the invention avoid the issues of antibody cross-reactivity and non-specific adsorption that occur when assays are multiplexed in bulk format. The use of droplets allows high levels of multiplexing while retaining the specificity of single-plex assays without the need for large sample volumes.

Methods of the invention involve forming a droplet that includes reagents for a sandwich assay (e.g., a first target binding agent having a differentially detectable identifier and a second target binding agent). Any technique known in the art for forming droplets may be used with methods of the invention. An exemplary method involves flowing a stream of reagent fluid such that it intersects two opposing streams of flowing carrier fluid. The carrier fluid is immiscible with the reagent fluid. Intersection of the reagent fluid with the two opposing streams of flowing carrier fluid results in partitioning of the reagent fluid into individual reagent droplets. The carrier fluid may be any fluid that is immiscible with the reagent fluid. An exemplary carrier fluid is oil. In certain embodiments, the carrier fluid includes a surfactant, such as a fluorosurfactant.

A sample containing target analyte (e.g., bacteria, virus, nucleic acid or protein) is introduced into a reagent droplet. This can occur by forming sample droplets and merging the sample droplets with the reagent droplets to form mixed droplets that include sample and reagents for the sandwich assay. Another technique involves contacting the reagent droplet with a fluid stream including the sample. Contact between the droplet and the fluid stream results in a portion of the fluid stream integrating with the droplet to form the mixed droplet.

Methods of the invention may be conducted in microfluidic channels. As such, in certain embodiments, methods of the invention may further involve flowing the droplet through a first channel and flowing the fluid stream through a second channel. The first and second channels are oriented such that the channels intersect each other. Any angle that results in an intersection of the channels may be used. In a particular embodiment, the first and second channels are oriented perpendicular to each other. Methods of the invention may further involve applying an electric field to the droplet and the fluid stream. The electric field assists in rupturing the interface separating the two sample fluids. In particular embodiments, the electric field is a high-frequency electric field.

After forming the mixed droplet, a sandwich assay is conducted in the droplet such that complexes of target analyte and first and second binding agents are formed. In certain embodiments, the assay is conducted in the presence of a competitive inhibitor. The competitive inhibitor has affinity to analytes in the sample that may compete for binding with the target analyte. The competitive inhibitor binds these competing analytes and ensures that they do not compete with the target analyte for binding to the binding agents.

Generally, the second binding agent is configured such that it can be coupled to a solid support. For example, a terminal portion of the second binding agent may be functionalized with a terminal amine such that it can covalently bind an epoxide coated surface. Alternatively, a terminal end of the second binding agent is functionalized with one member of a binding pair while a surface of the solid support is coated with the other member of the binding pair (e.g., biotin/avidin; biotin/streptavidin/or digoxigenin/anti-digoxigenin). The support may be a bead that is present in the droplet or it may be a substrate outside of the droplet. Generally, the complexes become immobilized on the solid support while uncomplexed sample components remain unbound in the sample.

Bead-bound complexes can be released from the droplets and separated from the unbound sample components. Alternatively, the droplet contents are released and the complexes become immobilized to a solid support. A wash step is performed to remove the unbound sample components, and then the target identifier associated with the first binding agent is detected.

The target identifier may be any type of differentially-detectable identifier, such as an optically detectable label (e.g., fluorescent or chemiluminescent label), radiolabel, electrochemical label, or a barcode label. Detection may be by any methods known in the art and the detection method will depend on the type of identifier used. The identifier may be releasably attached to the first binding agent or may be irreversibly attached to the first binding agent.

In particular embodiments, the identifier is a barcode sequence. The barcode sequences can be released from the first binding agents and then attached to each other to produce a single nucleic acid strand. This strand is then amplified (e.g., rolling circle amplification or PCR) and the amplified products are sequenced.

Sequencing may be by any method known in the art. In certain embodiments, sequencing is sequencing by synthesis. In other embodiments, sequencing is single molecule sequencing by synthesis. In certain embodiments, sequencing involves hybridizing a primer to the template to form a template/primer duplex, contacting the duplex with a polymerase enzyme in the presence of a detectably labeled nucleotides under conditions that permit the polymerase to add nucleotides to the primer in a template-dependent manner, detecting a signal from the incorporated labeled nucleotide, and sequentially repeating the contacting and detecting steps at least once, wherein sequential detection of incorporated labeled nucleotide determines the sequence of the nucleic acid. Exemplary detectable labels include radiolabels, florescent labels, enzymatic labels, etc. In particular embodiments, the detectable label may be an optically detectable label, such as a fluorescent label. Exemplary fluorescent labels include cyanine, rhodamine, fluorescien, coumarin, BODIPY, alexa, or conjugated multi-dyes.

Another aspect of the invention provides reagent droplet libraries. Such libraries include a plurality of droplets containing the elements necessary for a sandwich assay prior to introduction of the target analyte. Preferably, droplets are surrounded by an immiscible carrier fluid, e.g., aqueous droplets surrounded by oil. Each droplet includes a first binding agent having a differentially detectable identifier and a second binding agent. The binding agents are any molecules that can bind a target analyte in a sample. Exemplary binding agents include DNA, RNA, LNA, PNA, proteins, antibodies, or aptamers. Each droplet may further include a sample identifier that can bind to the identifier linked to the first binding agent. In this manner, each droplet includes an identifier for a particular target analyte and an identifier for a specific droplet. Each droplet may further include a competitive inhibitor.

Other aspects and advantages of the invention are apparent upon consideration of the following detailed description thereof.

DETAILED DESCRIPTION

Figure 1:
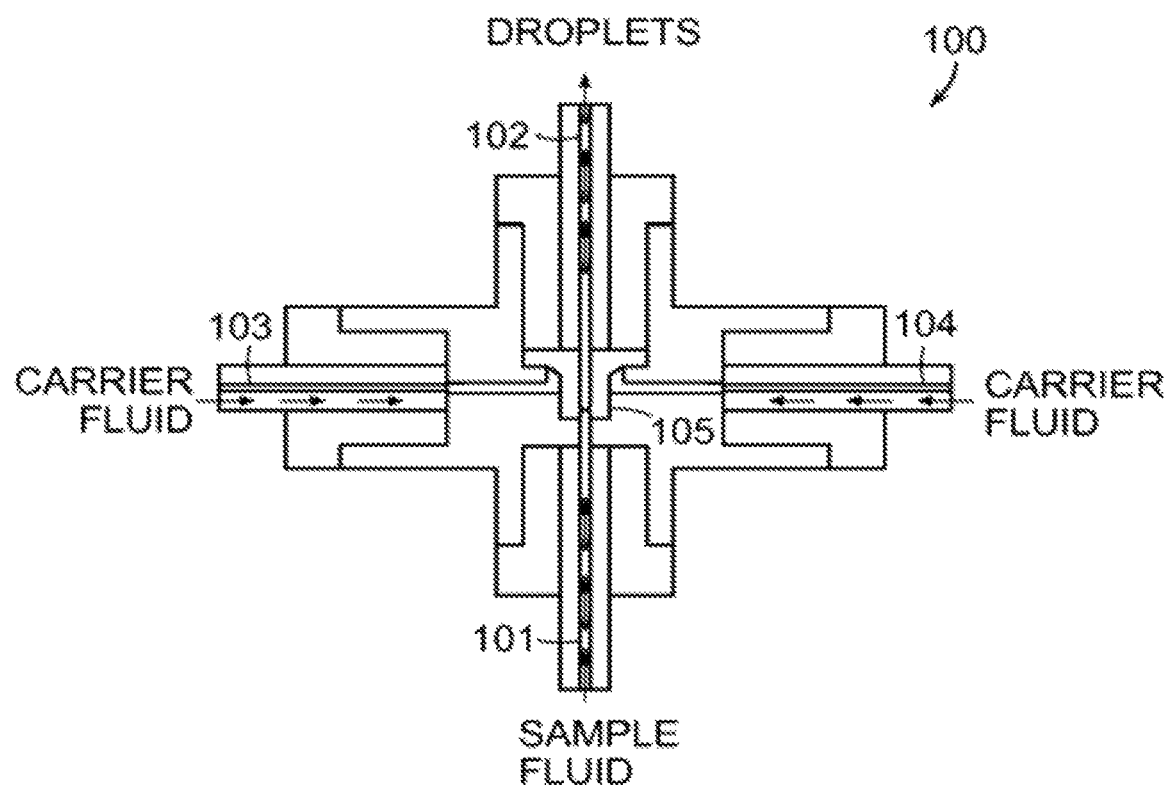
FIG. 1 is a drawing showing a device for droplet formation.

The invention generally relates to sandwich assays in droplets. In certain aspects, the invention provides methods for detecting and optionally quantifying a target analyte by forming a compartmentalized portion of fluid including a portion of a sample suspected of containing a target analyte, a first binding agent specific to the target analyte and having a target identifier, and a second binding agent specific to a different part of the target analyte under conditions that produce a complex of the first and second binding agents with the target analyte, separating the complexes from uncomplexed target identifiers, and detecting the complexes thereby detecting the target analyte. The invention allows for a high degree of multiplexing, thus allowing the use of multiple samples, targets or both. Moreover, the invention is useful to quantify targets as detailed below. There are numerous variations in terms of the manner in which devices and methods of the invention operate. A number of non-limiting examples are provided below. However, it is clear to one of skill in the art that numerous additional advantages and features of the invention are apparent upon consideration of the present specification and the examples that follow.

Samples

One of skill in the art will recognize that methods and systems of the invention are not limited to any particular type of sample, and methods and systems of the invention may be used with any type of organic, inorganic, or biological molecule. In particular embodiments the sample includes nucleic acid target molecules. Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid target molecules can be obtained from any cellular material, obtained from an animal, plant, bacterium, fungus, or any other cellular organism. In certain embodiments, the nucleic acid target molecules are obtained from a single cell. Biological samples for use in the present invention include viral particles or preparations. Nucleic acid target molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid target molecules can also be isolated from cultured cells, such as a primary cell culture or a cell line. The cells or tissues from which target nucleic acids are obtained can be infected with a virus or other intracellular pathogen. A sample can also be total RNA extracted from a biological specimen, a cDNA library, viral, or genomic DNA.

Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Nucleic acid molecules may be single-stranded, double-stranded, or double-stranded with single-stranded regions (for example, stem- and loop-structures).

Nucleic acid obtained from biological samples typically is fragmented to produce suitable fragments for analysis. Target nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid from a biological sample is fragmented by sonication. In another embodiment, nucleic acid is fragmented by a hydroshear instrument. Generally, individual nucleic acid target molecules can be from about 40 bases to about 40 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In one embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-$C_6H_4$-(O$CH_2$—$CH_2$)$_x$OH, x=9-10, Triton® X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), .beta.-mercaptoethanol, DTE, GSH, cysteine, cysteamine, tricarboxyethyl phosphine (TCEP), or salts of sulfurous acid.

Size selection of the nucleic acids may be performed to remove very short fragments or very long fragments. The nucleic acid fragments can be partitioned into fractions comprising a desired number of fragments using any suitable method known in the art. Suitable methods to limit the fragment size in each fragment are known in the art. In various embodiments of the invention, the fragment size is limited to between about 10 and about 100 Kb or longer.

In another embodiment, the sample includes individual target proteins, protein complexes, proteins with translational modifications, and protein/nucleic acid complexes. Protein targets include peptides, and also include enzymes, hormones, structural components such as viral capsid proteins, and antibodies. Protein targets may be synthetic or derived from naturally-occurring sources. In one embodiment of the invention protein targets are isolated from biological samples containing a variety of other components including lipids, non-template nucleic acids, and nucleic acids. In certain embodiments, protein targets may be obtained from an animal, bacterium, fungus, cellular organism, and single cells. Protein targets may be obtained directly from an organism or from a biological sample obtained from the organism, including bodily fluids such as blood, urine, cerebrospinal fluid, seminal fluid, saliva, sputum, stool and tissue. Protein targets may also be obtained from cell and tissue lysates and biochemical fractions. An individual protein is an isolated polypeptide chain. A protein complex includes two or polypeptide chains. Samples may include proteins with post translational modifications including but not limited to phosphorylation, methionine oxidation, deamidation, glycosylation, ubiquitination, carbamylation, s-carboxymethylation, acetylation, and methylation. Protein/nucleic acid complexes include cross-linked or stable protein-nucleic acid complexes.

Extraction or isolation of individual proteins, protein complexes, proteins with translational modifications, and protein/nucleic acid complexes is performed using methods known in the art.

The invention is useful to detect and/or quantify other target molecules, such as any molecule that can be specifically bound in at least two distinct portions of the target or any molecule in complex with at least one other molecule that can be specifically bound by binding agents.

Droplet Formation

Methods of the invention involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41, 780) and European publication number EP2047910 to Raindance Technologies Inc. The content of each of which is incorporated by reference herein in its entirety.

Figure 2:
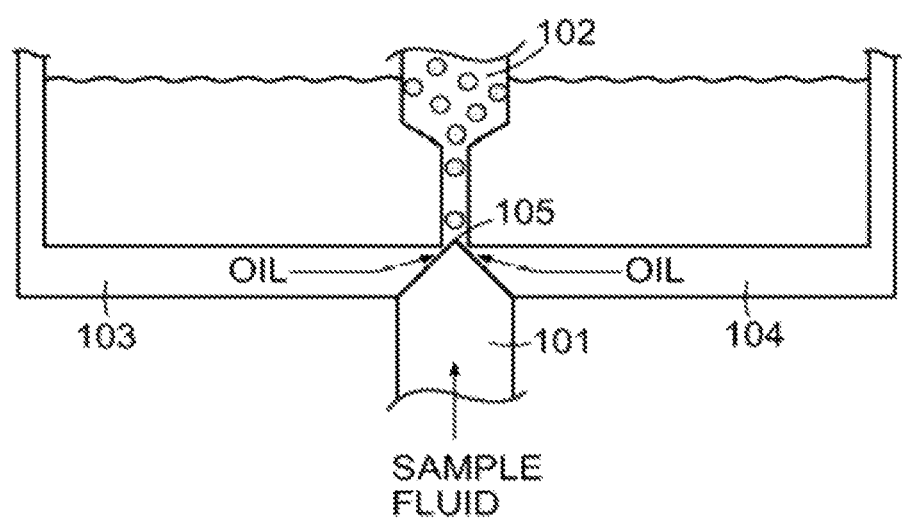
FIG. 2 is a drawing showing a device for droplet formation.
Figure 3B:
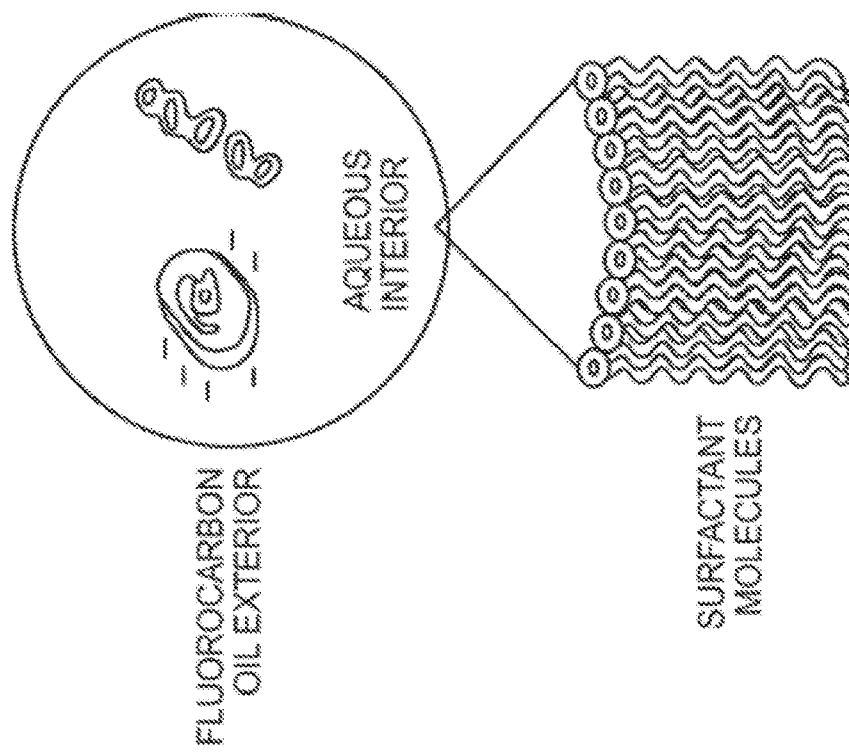
FIGS. 3A-D depict droplet generation, merging, and combining of droplets in an embodiment of the invention.
Figure 3A:
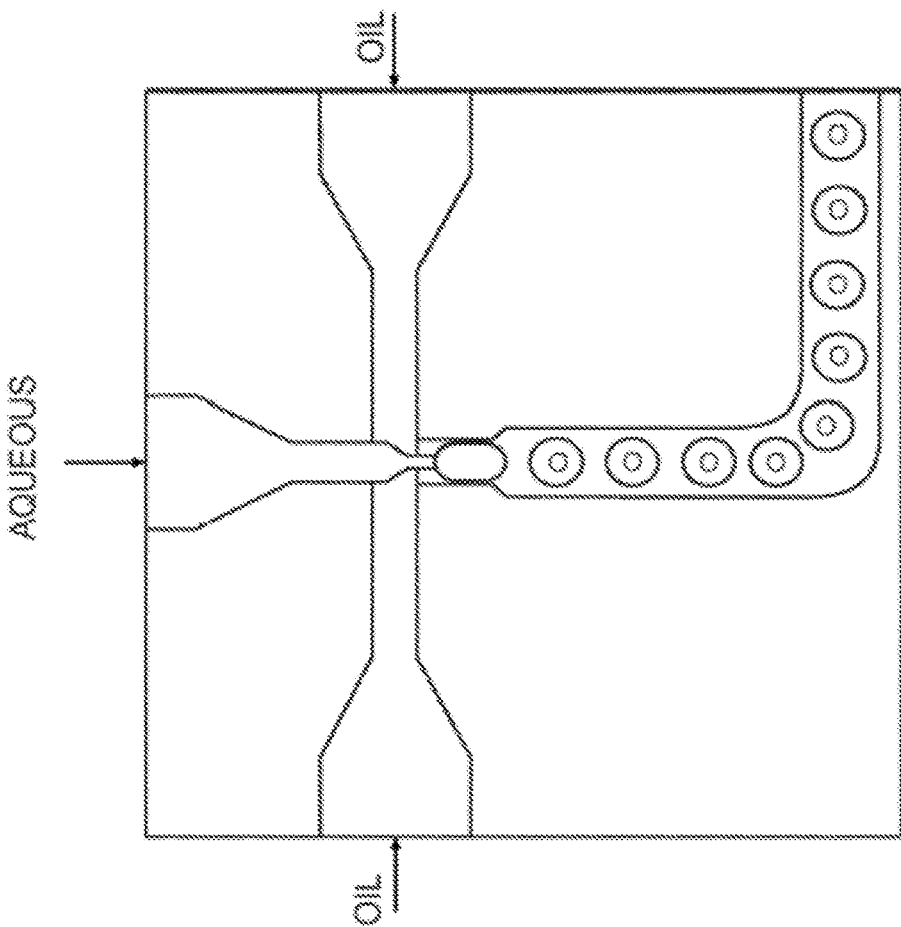
Figure 3C:
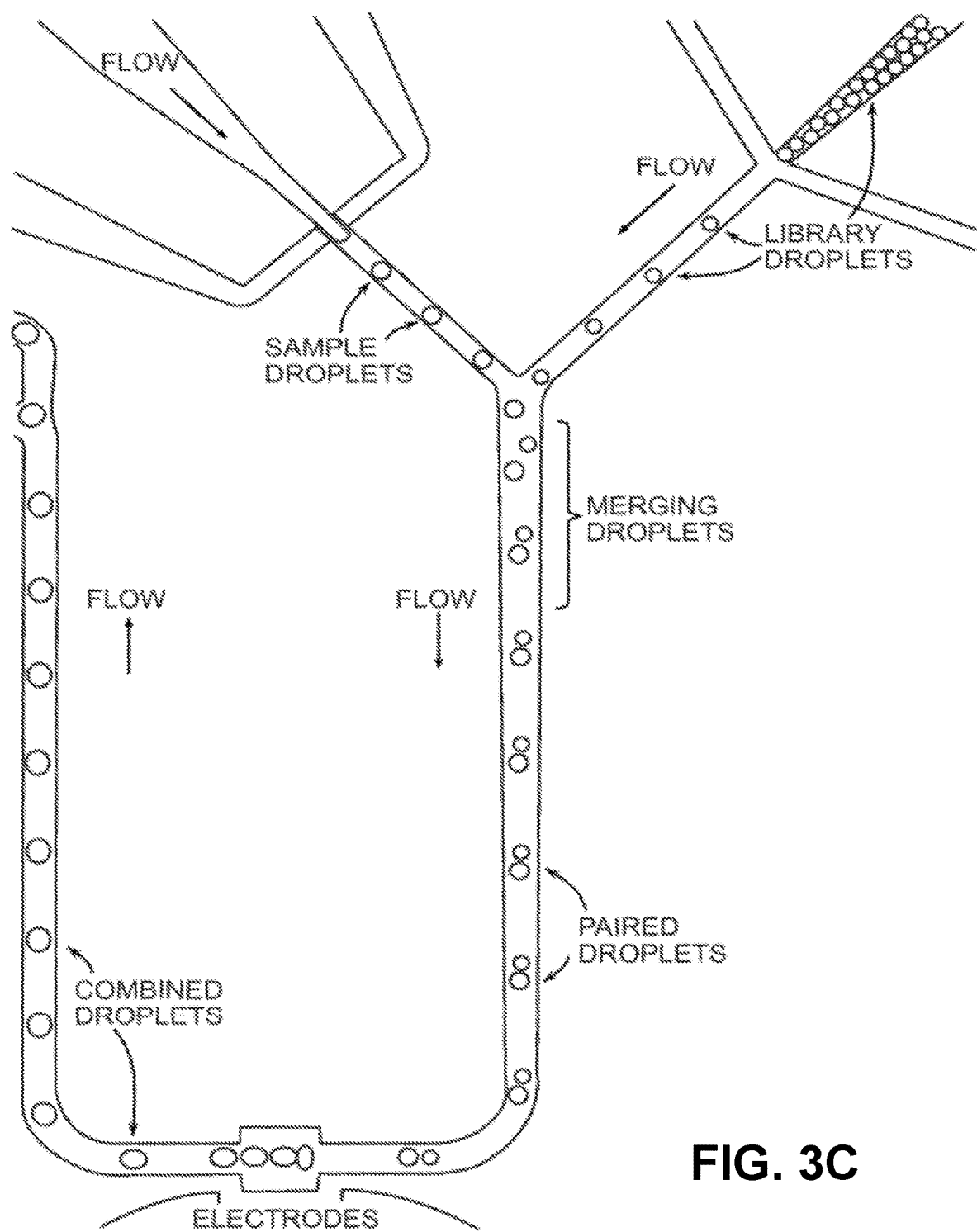
Figure 3D:
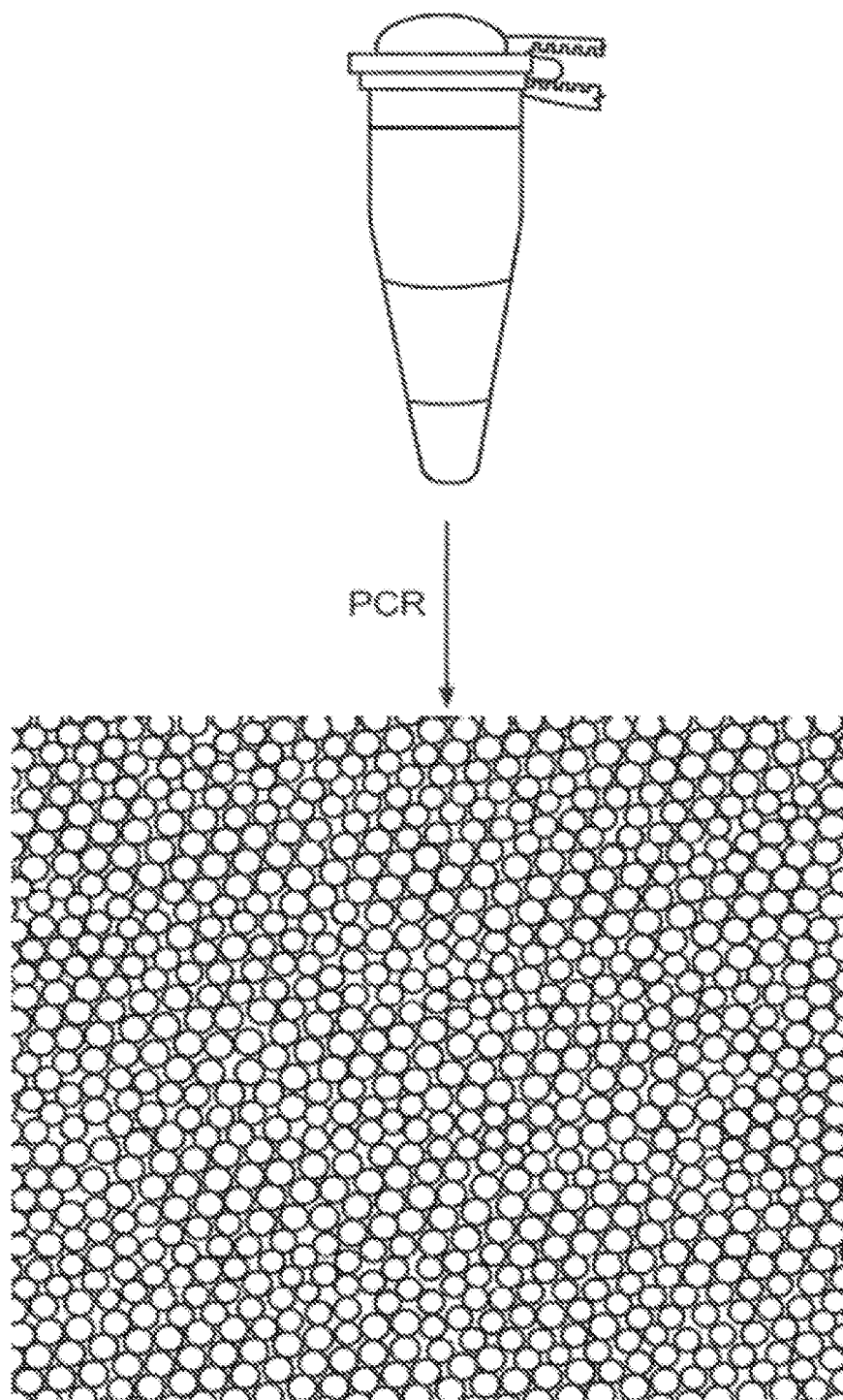
Figure 4A:
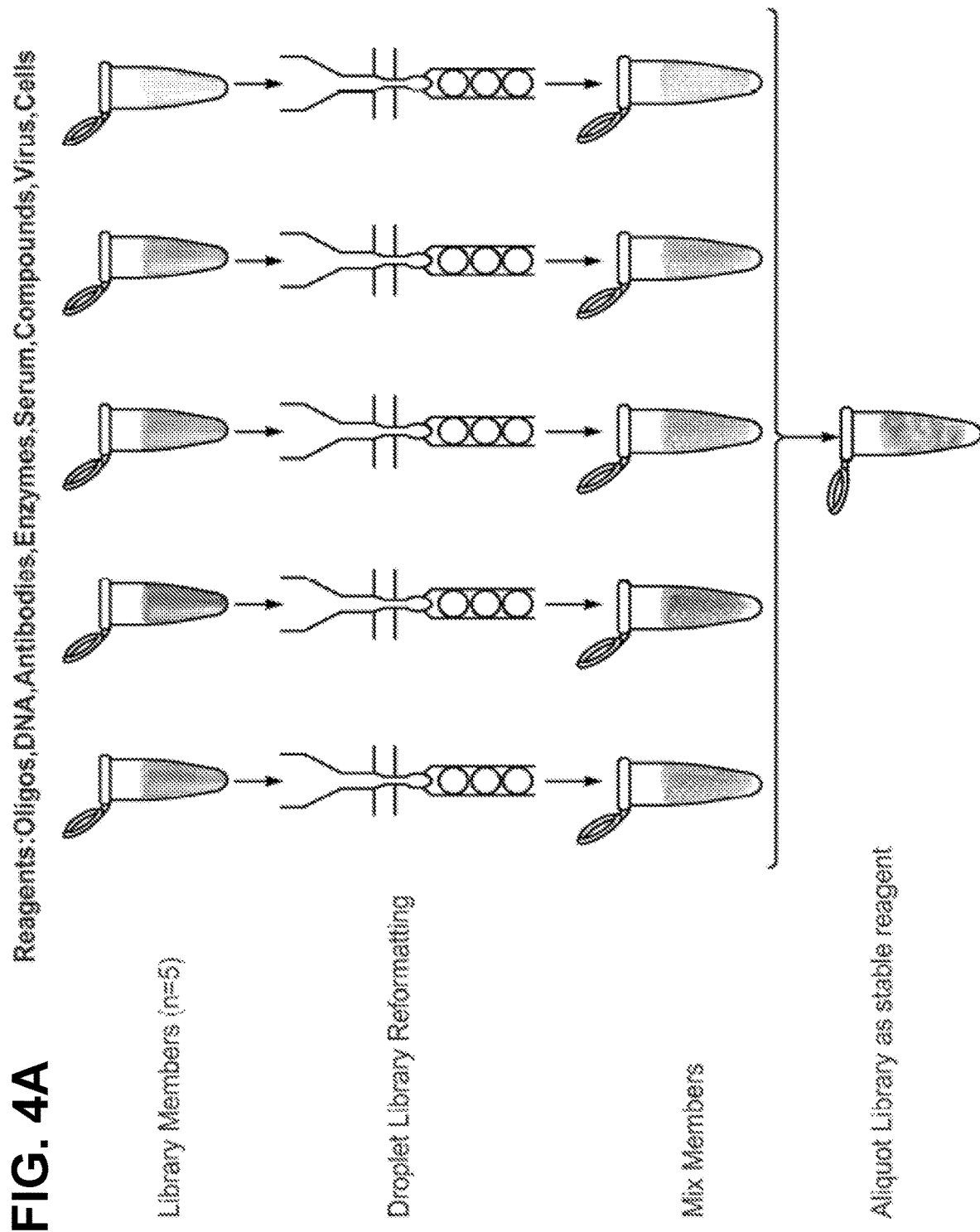
FIGS. 4A-C depict droplet library formation in an embodiment of the invention.
Figure 4B:
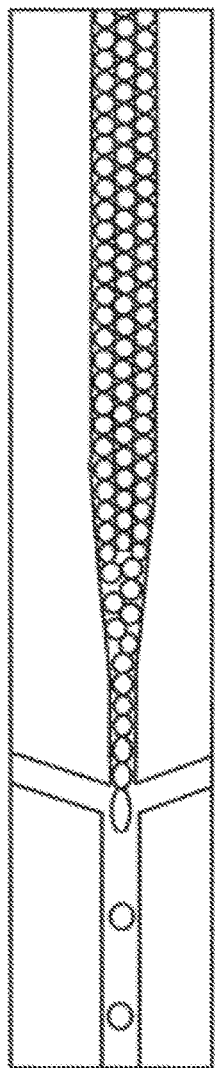
Figure 4C:
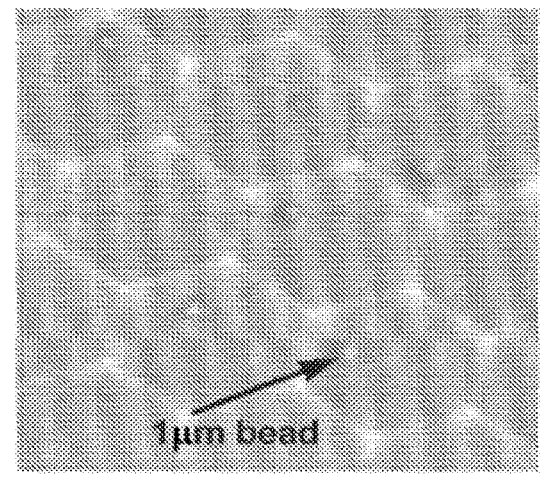

FIG. 1 shows an exemplary embodiment of a device 100 for droplet formation. Device 100 includes an inlet channel 101, and outlet channel 102, and two carrier fluid channels 103 and 104. Channels 101, 102, 103, and 104 meet at a junction 105. Inlet channel 101 flows sample fluid to the junction 105. Carrier fluid channels 103 and 104 flow a carrier fluid that is immiscible with the sample fluid to the junction 105. Inlet channel 101 narrows at its distal portion wherein it connects to junction 105 (See FIG. 2). Inlet channel 101 is oriented to be perpendicular to carrier fluid channels 103 and 104. Droplets are formed as sample fluid flows from inlet channel 101 to junction 105, where the sample fluid interacts with flowing carrier fluid provided to the junction 105 by carrier fluid channels 103 and 104. Outlet channel 102 receives the droplets of sample fluid surrounded by carrier fluid.

Another approach to merging sample fluids involves forming a droplet, and contacting the droplet with a fluid stream, in which a portion of the fluid stream integrates with the droplet to form a mixed droplet. In this approach, only one phase needs to reach a merge area in a form of a droplet.

A reagent droplet, or library of reagent droplets is formed as described above, and can be stored in a collection of other droplets for combining with samples after re-introduction into a microfluidic device. After formation of the reagent droplet, the droplet is contacted with a flow of a sample fluid stream. Contact between the reagent droplet and the fluid stream results in a portion of the sample fluid stream integrating with the reagent droplet to form a mixed droplet.

The monodisperse reagent droplets flow through a first channel separated from each other by immiscible carrier fluid and suspended in the immiscible carrier fluid. The droplets are delivered to the merge area, i.e., junction of the first channel with the second channel, by a pressure-driven flow generated by a positive displacement pump. While droplet arrives at the merge area, a bolus of a sample fluid is protruding from an opening of the second channel into the first channel. Preferably, the channels are oriented perpendicular to each other. However, any angle that results in an intersection of the channels may be used.

The bolus of the sample fluid stream continues to increase in size due to pumping action of a positive displacement pump connected to channel, which outputs a steady stream of the second sample fluid into the merge area. The flowing reagent droplet eventually contacts the bolus of the sample fluid that is protruding into the first channel. Contact between the two fluids results in a portion of the sample fluid being segmented from the sample fluid stream and joining with the reagent fluid droplet to form a mixed droplet. In certain embodiments, each incoming droplet of reagent fluid is merged with the same amount of sample fluid.

In certain embodiments, an electric charge is applied to the first and second sample fluids. Description of applying electric charge to sample fluids is provided in Link et al. (U.S. patent application number 2007/0003442) and European Patent Number EP2004316 to Raindance Technologies Inc, the content of each of which is incorporated by reference herein in its entirety. Electric charge may be created using any suitable technique, for example, by placing the reagent droplet and the sample fluid within an electric field (which may be AC, DC, etc.), and/or causing a reaction to occur that causes the reagent droplet and the sample fluid to have an electric charge, for example, a chemical reaction, an ionic reaction, a photocatalyzed reaction, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used.

The electric field facilitates rupture of the interface separating the sample fluid and the droplet. Rupturing the interface facilitates merging of bolus of the s sample fluid and the reagent droplet. The forming mixed droplet continues to increase in size until it a portion of the sample fluid breaks free or segments from the sample fluid stream prior to arrival and merging of the next reagent droplet. The segmenting of the portion of the sample fluid from the sample fluid stream occurs as soon as the shear force exerted on the forming mixed droplet by the immiscible carrier fluid overcomes the surface tension whose action is to keep the segmenting portion of the sample fluid connected with the second sample fluid stream. The now fully formed mixed droplet continues to flow through the first channel.

The sample fluid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with enzymes can be used. The carrier fluid is one that is immiscible with the sample fluid. The carrier fluid can be a non-polar solvent, decane (e g., tetradecane or hexadecane), fluorocarbon oil, silicone oil or another oil (for example, mineral oil).

In certain embodiments, the carrier fluid contains one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be coated with a surfactant. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the carrier fluid.

The oil can comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) may be important to maintain the stability and integrity of the droplets and may also be beneficial for the subsequent use of the droplets within the library for the various biological and chemical assays described herein. Fluids (e.g., aqueous fluids, immiscible oils, etc.) and other surfactants that can be utilized in the droplet libraries of the present invention are described in greater detail herein.

Microfluidic Systems

Reagents can be reformatted as droplet libraries utilizing automated devices. Specifically, the library element components can be placed onto plates containing any number of wells, i.e. 96, 384, etc. The plates can then be placed in any one of a number of devices known in the art for forming the droplets. The droplets can be placed into a vial or other such container, containing the stable droplet library for later use. In general, the process aspirates the components from each well of a well plate and infuses them through tubing connected to a microfluidic device (described in greater detail herein) which can be used to form the droplets that constitute a single library member or 'element'. The tubing is rinsed at a wash station and then the process can be repeated to generate droplets for the next library element.

A collection vial can be used to contain the droplets made using the Automated Droplet Library Production. In one example, the collection vial has two holes, a first hole in the center of the vial cap and a second hole part way to the edge of the vial cap. The vial is first filled with oil through the second hole to purge air out first hole, the emulsion is then introduced to the vial through the first hole, typically this is done sequentially one library element at a time at low volume fraction, and oil is displaced and goes out through the second hole. The collected droplets can be stored in the vial for periods of time in excess of 3 months. To remove the emulsion for use or to make smaller aliquots, oil is introduced through the second opening to displace the emulsion and drive out the first opening.

The droplet libraries of the present invention are preferably formed by utilizing microfluidic devices and are preferably utilized to perform various biological and chemical assays on microfluidic devices, as described in detail herein. The present invention also provides embedded microfluidic nozzles. In order to create a monodisperse (<1.5% polydispersity) emulsion directly from a library well, a nozzle can be formed directly into the fitting used to connect the storage well/reservoir (e.g. syringe) to a syringe tip (e.g. capillary tubing). Examples of suitable nozzles to create the droplet libraries of the instant invention are described in WO 2007/081385 and WO 2008/063227.

Since the flow is three dimensional, under this design surface wetting effects are minimized. The nozzle can be made from one or two oil lines providing constant flow of oil into the nozzle, a connection to the capillary tubing, and a connection to the storage well/reservoir (e.g. syringe). The high resolution part of the nozzle can be made out of a small bore tubing or a small, simple part molded or stamped from an appropriate material (Teflon®, plastic, metal, etc). If necessary, the nozzle itself could be formed into the tip of the ferrule using post mold processing such as laser ablation or drilling.

This nozzle design eliminates the surface wetting issues surrounding the quasi-2D flow associated with typical microfluidic nozzles made using soft lithography or other standard microfluidic chip manufacturing techniques. This is because the nozzle design is fully 3-dimensional, resulting is a complete isolation of the nozzle section from the continuous aqueous phase. This same design can also be used for generation of emulsions required for immediate use, where the aqueous line would be attached directly to a syringe and the outlet of the nozzle would be used to transport the emulsion to the point of use (e.g. into a microfluidic PCR chip, delay line, etc).

In another embodiment, the present invention provides compositions and methods to directly emulsify library elements from standard library storage geometries (e.g. 96 well plates, etc). In order to create a monodisperse emulsion from fluids contained in a library well plate, this invention would include microfluidic based nozzles manufactured simultaneously with an appropriately designed fluidic interconnect or well.

Specifically, the microfluidic devices and methods described herein are based on the creation and electrical manipulation of aqueous phase droplets (e.g., droplet libraries) completely encapsulated by an inert immiscible oil stream. This combination enables precise droplet generation, highly efficient, electrically addressable, droplet coalescence, and controllable, electrically addressable single droplet sorting. The microfluidic devices include one or more channels and modules. The integration of these modules is an essential enabling technology for a droplet based, high-throughput microfluidic reactor system and provides an ideal system for utilizing the droplet libraries provided herein for numerous biological, chemical, or diagnostic applications.

Substrates

The microfluidic device of the present invention includes one or more analysis units. An "analysis unit" is a microsubstrate, e.g., a microchip. The terms microsubstrate, substrate, microchip, and chip are used interchangeably he, ein. The analysis unit includes at least one inlet channel, at least one main channel and at least one inlet module. The analysis unit can further include at least one coalescence module. at least one detection module and one or more sorting modules. The sorting module can be in fluid communication with branch channels which are in fluid communication with one or more outlet modules (collection module or waste module). For sorting applications, at least one detection module cooperates with at least one sorting module to divert flow via a detector-originated signal. It shall be appreciated that the "modules" and "channels" are in fluid communication with each other and therefore may overlap; i.e., there may be no clear boundary where a module or channel begins or ends. A plurality of analysis units of the invention may be combined in one device. The dimensions of the substrate are those of typical microchips, ranging between about 0.5 cm to about 15 cm per side and about 1 micron to about 1 cm in thickness. The analysis unit and specific modules are described in further detail in WO 2006/040551; WO 2006/040554; WO 2004/002627; WO 2004/091763; WO 2005/021151; WO 2006/096571; WO 2007/089541; WO 2007/081385 and WO 2008/063227.

A variety of materials and methods can be used to form any of the described components of the systems and devices of the invention. For example, various components of the invention can be formed from solid materials, in which the channels can be formed via molding, micromachining, film deposition processes such as spin coating and chemical vapor deposition, laser fabrication, photolithographic techniques, etching methods including wet chemical or plasma processes, and the like. See, for example, Angell, et al., Scientific American, 248:44-55, 1983. At least a portion of the fluidic system can be formed of silicone by molding a silicone chip. Technologies for precise and efficient formation of various fluidic systems and devices of the invention from silicone are known. Various components of the systems and devices of the invention can also be formed of a polymer, for example, an elastomeric polymer such as polydimethylsiloxane ("PDMS"), polytetrafluoroethylene ("PTFE") or Teflon®, or the like, or thermoplastic polymers.

Silicone polymers are preferred, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying formation of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be formed and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in Duffy et al., "Rapid Prototyping of Microfluidic Systems and Polydimethylsiloxane," Anal. Chem., 70:474-480, 1998.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

Channels

The microfluidic substrates of the present invention include channels that form the boundary for a fluid. A "channel," as used herein, means a feature on or in a substrate that at least partially directs the flow of a fluid. In some cases, the channel may be formed, at least in part, by a single component, e.g., an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel).

In embodiments where the channel is completely covered, at least one portion of the channel can have a cross-section that is completely enclosed, and/or the entire channel may be completely enclosed along its entire length with the exception of its inlet and outlet. The channels of the invention can be formed, for example by etching a silicon chip using conventional photolithography techniques, or using a micromachining technology called "soft lithography" as described by Whitesides and Xia, Angewandte Chemie International Edition 37, 550 (1998).

An open channel generally will include characteristics that facilitate control over fluid transport, e.g., structural characteristics (an elongated indentation) and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases.

A "main channel" is a channel of the device of the invention that permits the flow of molecules, cells, small molecules or particles past a coalescence module for coalescing one or more droplets, and, if present, a detection module for detection (identification) or measurement of a droplet and a sorting module for sorting a droplet based on the detection in the detection module. The main channel is typically in fluid communication with the coalescence, detection and/or sorting modules, as well as, an inlet channel of the inlet module. The main channel is also typically in fluid communication with an outlet module and optionally with branch channels, each of which may have a collection module or waste module. These channels permit the flow of molecules, cells, small molecules or particles out of the main channel. An "inlet channel" permits the flow of molecules, cells, small molecules or particles into the main channel.

One or more inlet channels communicate with one or more means for introducing a sample into the device of the present invention. The inlet channel communicates with the main channel at an inlet module.

The microfluidic substrate can also comprise one or more fluid channels to inject or remove fluid in between droplets in a droplet stream for the purpose of changing the spacing between droplets. The channels of the device of the present invention can be of any geometry as described. However, the channels of the device can comprise a specific geometry such that the contents of the channel are manipulated, e.g., sorted, mixed, prevent clogging, etc.

A microfluidic substrate can also include a specific geometry designed in such a manner as to prevent the aggregation of biological/chemical material and keep the biological/chemical material separated from each other prior to encapsulation in droplets. The geometry of channel dimension can be changed to disturb the aggregates and break them apart by various methods, that can include, but is not limited to, geometric pinching (to force cells through a (or a series of) narrow region(s), whose dimension is smaller or comparable to the dimension of a single cell) or a barricade (place a series of barricades on the way of the moving cells to disturb the movement and break up the aggregates of cells). To prevent material (e.g., cells and other particles or molecules) from adhering to the sides of the channels, the channels (and coverslip, if used) may have a coating which minimizes adhesion. The surface of the channels of the microfluidic device can be coated with any anti-wetting or blocking agent for the dispersed phase. The channel can be coated with any protein to prevent adhesion of the biological/chemical sample. Channels can be coated by any means known in the art. For example, the channels are coated with Teflon®, BSA, PEG-silane and/or fluorosilane in an amount sufficient to prevent attachment and prevent clogging. In another example, the channels can be coated with a cyclized transparent optical polymer obtained by copolymerization of perfluoro (alkenyl vinyl ethers), such as the type sold by Asahi Glass Co. under the trademark Cytop. In such an example, the coating is applied from a 0.1-0.5 wt % solution of Cytop CTL-809M in CT-Solv 180. This solution can be injected into the channels of a microfluidic device via a plastic syringe. The device can then be heated to about 90° C. for 2 hours, followed by heating at 200° C. for an additional 2 hours. In another embodiment, the channels can be coated with a hydrophobic coating of the type sold by PPG Industries, Inc. under the trademark Aquapel (e.g., perfluoroalkylalkylsilane surface treatment of plastic and coated plastic substrate surfaces in conjunction with the use of a silica primer layer) and disclosed in U.S. Pat. No. 5,523,162. By fluorinating the surfaces of the channels, the continuous phase preferentially wets the channels and allows for the stable generation and movement of droplets through the device. The low surface tension of the channel walls thereby minimizes the accumulation of channel clogging particulates.

The surface of the channels in the microfluidic device can be also fluorinated by any means known in the art to prevent undesired wetting behaviors. For example, a microfluidic device can be placed in a polycarbonate dessicator with an open bottle of (tridecafluoro-1,1,2,2-tetrahydrooctyl)trichlorosilane. The dessicator is evacuated for 5 minutes, and then sealed for 20-40 minutes. The dessicator is then backfilled with air and removed. This approach uses a simple diffusion mechanism to enable facile infiltration of channels of the microfluidic device with the fluorosilane and can be readily scaled up for simultaneous device fluorination.

Fluids

The fluids described herein are related to the fluids within the droplet libraries and to the fluids within a microfluidic device. The microfluidic device of the present invention is capable of controlling the direction and flow of fluids and entities within the device. The term "flow" means any movement of liquid or solid through a device or in a method of the invention, and encompasses without limitation any fluid stream, and any material moving with, within or against the stream, whether or not the material is carried by the stream. For example, the movement of molecules, beads, cells or virions through a device or in a method of the invention, e.g. through channels of a microfluidic chip of the invention, comprises a flow. This is so, according to the invention, whether or not the molecules, beads, cells or virions are carried by a stream of fluid also comprising a flow, or whether the molecules, cells or virions are caused to move by some other direct or indirect force or motivation, and whether or not the nature of any motivating force is known or understood. The application of any force may be used to provide a flow, including without limitation, pressure, capillary action, electro-osmosis, electrophoresis, dielectrophoresis, optical tweezers, and combinations thereof, without regard for any particular theory or mechanism of action, so long as molecules, cells or virions are directed for detection, measurement or sorting according to the invention. Specific flow forces are described in further detail herein.

The flow stream in the main channel is typically, but not necessarily, continuous and may be stopped and started, reversed or changed in speed. A liquid that does not contain sample molecules, cells or particles can be introduced into a sample inlet well or channel and directed through the inlet module, e.g., by capillary action, to hydrate and prepare the device for use. Likewise, buffer or oil can also be introduced into a main inlet region that communicates directly with the main channel to purge the device (e.g., or "dead" air) and prepare it for use. If desired, the pressure can be adjusted or equalized, for example, by adding buffer or oil to an outlet module.

According to the invention, a fluidic stream may be continuous and/or discontinuous. A "continuous" fluidic stream is a fluidic stream that is produced as a single entity, e.g., if a continuous fluidic stream is produced from a channel, the fluidic stream, after production, appears to be contiguous with the channel outlet. The continuous fluidic stream is also referred to as a continuous phase fluid or carrier fluid. The continuous fluidic stream may be laminar (potentially including streams of two or more fluids), or turbulent in some cases.

Similarly, a "discontinuous" fluidic stream is a fluidic stream that is not produced as a single entity. The discontinuous fluidic stream is also referred to as the dispersed phase fluid or sample fluid. A discontinuous fluidic stream may have the appearance of individual droplets, optionally surrounded by a second fluid. The dispersed phase fluid can include a biological/chemical material. The biological/chemical material can be tissues, cells, particles, proteins, antibodies, amino acids, nucleotides, small molecules, and pharmaceuticals. The biological/chemical material can include one or more labels known in the art. The label can be an optical label, an enzymatic label or a radioactive label. The label can be any detectable label, e.g., a protein, a DNA tag, a dye, a quantum dot or a radio frequency identification tag, or combinations thereof. In some embodiments, the label is an optical label. The label can be detected by any means known in the art. Preferably, the label is detected by fluorescence polarization, fluorescence intensity, fluorescence lifetime, fluorescence energy transfer, pH, ionic content, temperature or combinations thereof Various labels and means for detection are described in greater detail herein.

The term "emulsion" refers to a preparation of one liquid distributed in small globules (also referred to herein as drops, droplets or NanoReactors) in the body of a second liquid. The first and second fluids are immiscible with each other. For example, the discontinuous phase can be an aqueous solution and the continuous phase can a hydrophobic fluid such as an oil. This is termed a water in oil emulsion. Alternatively, the emulsion may be a oil in water emulsion. In that example, the first liquid, which is dispersed in globules, is referred to as the discontinuous phase, whereas the second liquid is referred to as the continuous phase or the dispersion medium. The continuous phase can be an aqueous solution and the discontinuous phase is a hydrophobic fluid, such as an oil (e.g., decane, tetradecane, or hexadecane). The droplets or globules of oil in an oil in water emulsion are also referred to herein as "micelles", whereas globules of water in a water in oil emulsion may be referred to as "reverse micelles".

The fluidic droplets may each be substantially the same shape and/or size. The droplets may be uniform in size. The shape and/or size can be determined, for example, by measuring the average diameter or other characteristic dimension of the droplets. The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, is the mathematically-defined average diameter of the droplet, integrated across the entire surface. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The 15 average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

As used herein, the term "NanoReactor" and its plural encompass the terms "droplet", "nanodrop", "nanodroplet", "microdrop" or "microdroplet" as defined herein, as well as an integrated system for the manipulation and probing of droplets, as described in detail herein. Nanoreactors as described herein can be 0.1-1000 μm (e.g., 0.1, 0.2 . . . 5, 10, 15, 20, 25, 30, 35, 40, 45, 50 . . . 1000), or any size within this range. Droplets at these dimensions tend to conform to the size and shape of the channels, while maintaining their respective volumes. Thus, as droplets move from a wider channel to a narrower channel they become longer and thinner, and vice versa.

The microfluidic substrate of this invention most preferably generate round, highly uniform, monodisperse droplets (<1.5% polydispersity). Droplets and methods of forming monodisperse droplets in microfluidic channels is described in WO 2006/040551; WO 2006/040554; WO 2004/002627; WO 2004/091763; WO 2005/021151; WO 2006/096571; WO 2007/089541; WO 2007/081385 and WO 2008/063227.

The droplet forming liquid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with the population of molecules, cells or particles to be analyzed and/or sorted can be used. The fluid passing through the main channel and in which the droplets are formed is one that is immiscible with the droplet forming fluid. The fluid passing through the main channel can be a non-polar solvent, decane (e.g., tetradecane or hexadecane), fluorocarbon oil, silicone oil or another oil (for example, mineral oil).

The droplet may also contain biological/chemical material (e.g., molecules, cells, or other particles) for combination, analysis and/or sorting in the device. The droplets of the dispersed phase fluid can contain more than one particle or can contain no more than one particle. Droplets of a sample fluid can be formed within the inlet module on the microfluidic device or droplets (or droplet libraries) can be formed before the sample fluid is introduced to the microfluidic device (stable droplet libraries can be stored after manufacturing, for introduction onto the microfluidic device and combination with sample droplets or other droplet libraries). To permit effective interdigitation, coalescence and detection, the droplets comprising each sample to be analyzed must be monodisperse. As described in more detail herein, in many applications, different samples to be analyzed are contained within droplets of different sizes. Droplet size must be highly controlled to ensure that droplets containing the correct contents for analysis and coalesced properly. As such, the present invention provides devices and methods for forming droplets and droplet libraries.

Surfactants

The fluids used in the invention may contain one or more additives, such as agents which reduce surface tensions (surfactants). Surfactants can include Tween, Span, fluorosurfactants, and other agents that are soluble in oil relative to water. In some applications, performance is improved by adding a second surfactant to the aqueous phase. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing. The present invention provides compositions and methods to stabilize aqueous droplets in a fluorinated oil and minimize the transport of positively charged reagents (particularly, fluorescent dyes) from the aqueous phase to the oil phase. The droplets may be coated with a surfactant. Preferred surfactants that may be added to the continuous phase fluid include, but ate not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In addition, ionic surfactants such as sodium dodecyl sulfate (SDS) may also be used. However, such surfactants are generally less preferably for many embodiments of the invention. For instance, in those embodiments where aqueous droplets are used as nanoreactors for chemical reactions (including biochemical reactions) or are used to analyze and/or sort biomaterials, a water soluble surfactant such as SDS may denature or inactivate the contents of the droplet.

The carrier fluid can be an oil (e.g., decane, tetradecane or hexadecane) or fluorocarbon oil that contains a surfactant (e.g., a non-ionic surfactant such as a Span surfactant) as an additive (preferably between about 0.2 and 5% by volume, more preferably about 2%). A user can preferably cause the carrier fluid to flow through channels of the microfluidic device so that the surfactant in the carrier fluid coats the channel walls.

Fluorocarbon oil continuous phases are well-suited as the continuous phase for aqueous droplet libraries for a number of reasons. Fluorous oils are both hydrophobic and lipophobic. Therefore, they have low solubility for components of the aqueous phase and they limit molecular diffusion between droplets. Also, fluorous oils present an inert interface for chemistry and biology within droplets. In contrast to hydrocarbon or silicone oils, fluorous oils do not swell PDMS materials, which is a convenient material for constructing microfluidic channels. Finally, fluorocarbon oils have good solubility for gases, which is necessary for the viability of encapsulated cells.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the fluorous oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A very large body of fundamental research and commercial application development exists for non-fluorous surfactants and emulsions ranging from sub-micron droplets to very large, macroscopic emulsions. In contrast, fundamental knowledge and commercial practice with fluorinated oils and surfactants is much less common. More specifically, testing and development of fluorosurfactants and fluorous oil formulations for the application of creating large libraries of micron-scale droplets with unique composition is limited to only a few groups throughout the world. Only a few commercially-available fluorosurfactants that stabilize water-in-fluorocarbon oil emulsions exist. For instance, surfactants with short fluorotelomer-tails (typically perfluorinated C6 tO C10) are available, but they do not provide sufficient long-term emulsion stability. Fluorosurfactants with longer fluorocarbon tails, such as perfluoropolyether (PFPE), are limited to molecules with ionic headgroups.

Classes of oils are available from wide variety of fluorinated oils and are available from commercial sources. The requirements for the oil are (1) immiscibility with the aqueous phase, (2) solubility of emulsion stabilizing surfactants in the oil, and (3) compatibility and/or insolubility of reagents from the droplet phase. Oils include hydrofluoroethers, which are fluorinated alkyl chains coupled with hydrocarbon chemistry through and ether bond. One supplier of this type of oil is 3M.

The products are marketed as Novec Engineered Fluids or HFE-series oils. This oils include but are not limited to, HFE-7500, which is a preferred embodiment as it provides superior droplet stability seems to be higher. Other oils include FIFE-7100, -7200, -7600, which are examples of other HFEs available from 3M. These can be used as stand-alone oils or components of oil mixtures to optimize emulsion properties and performance. Other hydrofluoroethers are also available from other producers, distributors, or resellers may offer hydrofluoroethers. Another class of oil is perfluoroalkylamines, which are perfluorinated oils based on perfluoroalkyl amine structures. 3M produces these oils as Fluorinert Electronic Liquids (FC-oils). Fluorinert products differ by variations in alkyl chain length, branch structure, and combinations of different structures or pure oils. Many of them offer the potential for stand-alone oils or components of oil mixtures to optimize emulsion properties and performance. Specific examples are Fluorinert FC3283, Fluorinert FC-40, which are a preferred embodiments. Higher viscosity and boiling point useful for applications requiring elevated temperature (e.g., thermocyling for PCR). Other Fluorinert series can be used for stand-alone oils or components of oil mixtures to optimize emulsion properties and performance. Again, other perfluoroalkylamines are available from other producers, distributors, or resellers may offer perfluoroalkylamines.

Fluorinated organics/solvents offer a number of perfluorinated or partially fluorinated solvents are available from a variety of producers, distributors, and/or resellers. Many of them offer the potential for stand-alone oils or components of oil mixtures to optimize emulsion properties and performance. Examples of fluorinated organic reagents utilized, included (but not limited to) trifluoroacetic acid and hexafluoroisopropanol, to improve droplet stability in other fluorinated oil systems. Additionally, fluoropolymers may also be used within a microfluidic system. Examples of fluoropolymers include, Krytox GPL oils, Solvay Galden oils, and other liquid fluoropolymers. Other fluorinated materials find widespread use in a variety of industries, but they are generally not wellknown in the disciplines of interfacial, colloidal, physical, or synthetic organic chemistry. Therefore, a number of other candidates for oils exist in specialty and niche market applications. As such, new oils have been targeted partially that are perfluorinated materials, which are not widely recognized.

The properties of oils selected are based upon their chemical properties, such as, among others molecular structure, fluorine content and solvating strength. Physical properties of oils examined include viscosity, boiling point, thermal expansion coefficient, oil-in-water solubility, water-in-oil solubility, dielectric constant, polarity, and oil-in-water surface tension.

Classes of surfactants include fluorosurfactants that can be categorized by the type of fluorophilic portion of the molecule, the type of hydrophilic, or polar, portion, and the chemistry used to link the different parts of the molecule. Materials developed are capable of stabilizing an emulsion or droplet library. The preferred embodiment is the EA surfactant. Specifically, the EA surfactant is a Krytox-PEG-Krytox. The EA surfactant is a nonionic tri-block copolymer surfactant was developed to avoid issues that the ionic surfactants (e.g., RR, see below) which result from the use of some other ionic surfactant. Specifically, ionic surfactants interact with charged species in the droplets and can sequester ions (e.g., magnesium required for the PCR reaction) or other reagents to the oil phase. The structure of the EA surfactant comprises a PEG—approximately 600 Da with amine end functionality, PFPE—Mn is—5000-8000 from a Krytox FSH starting material and the linker is an amide coupling. Another surfactant includes the RR surfactant, which is a Krytox ammonium carboxylate. Alternative materials are alternative fluorophilic portion, i.e., PFPE (Solvay or Demnum), Poly(fluoroalkylacrylate) and other non-polymeric and partially fluorinated materials. Alternative headgroup chemistry for the hydrophilic portion includes, nonionic head groups like PEG (Mw, Mw/Mn (PDI)) and functionality (i.e., diblock, triblock and dendritic). Others include morpholino. Ionic head groups for the hydrophilic portion include anionic, such as elemental and amine salts and further cationic head portions. Other head group chemistries include zwitterionic, hybrid (e.g., PEG-ionic and zonyl FSO/FSN), lipophilic (e.g, lipophilic to promote bilayer and lipophilic spacer to hydrophile). Another alternative is alternative coupling chemistry such as, phosphoryl/Friedel-Crafts, spacer to organic handle and others.

Characteristics of surfactants are their molecular structure, determined by NMR, chromatography (e.g., HPLC, GPC/SEC), FTIR, mass spectrometry, and titrations. Purity of surfactants is another characteristic examined in addition to the fluorophile-hydrophile balance. A preferred embodiment includes oil-surfactant formulation for the application of library emulsions is R-oil (HFE-7500) mixed with 2 wt % EA surfactant ("REAM"). Concentrations of EA or RR surfactant at 0.1 wt % or lower to 5% or greater. Other formulations of oils and surfactants and other components added to the aqueous phase are used to improved and optimized the performance of the droplets performance. Those properties of the oil-surfactant mixture include simple mixtures (i.e., one oil and one surfactant, with varied surface concentration), co-surfactants, oil mixtures and additives, such as zonyl and TFA. Oil and surfactant mixture properties include surfactant solubility, critical micelle concentration (CMC), surfactant diffusivity, and interfacial tension, i.e., dynamic and equilibrium. Emulsion properties are also accounted for, those properties include size (absolute and size distribution), stability, transport, and biocompatibility. Stability relates directly to the coalesced droplets and their deformability/breaking and shredding ability. More particularly, the stability of the droplets in their generation, storage and shipping.

In general, production of surfactant and oils begins with the synthesis of surfactants and starting materials, such as PEG-diamine, EA and RR and also accounts for the purification processes, characterization, quality control, mixing and packaging. In one embodiment, the fluorosurfactant can be prepared by reacting the perfluorinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the continuous phase of the emulsion.

In another embodiment, a quaternary ammonium salt at the terminus of a hydrophilic oligomer is linked to a perfluoropolyether tail as shown in the following formula: PFPE-C(0)NH—$CH_2CH_2CH_2$—$(OCH_2CH_2)_3$0-$CH_2CH_2CH_2$—$N(CH_3)_3$+I—. Some specific molecular features of the present invention include, but are not limited to, PFPE is from Krytox 157 FSH (Mn—6500), amide bond linking PFPE to hydrophile, propyl group immediately adjacent to the amide, propyl group immediately adjacent to the trimethylamino terminus. Specific structural formations can alter performance relationships, for example, PFPE chain is sufficiently long for molecule to be soluble in perfluorinated oils, amide linker provides hydrolytic stability and hydrogen bonding site, and a combination of PEG and quaternary ammonium cation provide high anchoring strength to the aqueous phase as well as electrostatic repulsion and steric hindrance to minimize reagent transport.

Variables in the molecular structure include, but are not limited to, PFPE molecular weight and polydispersity, PFPE structure, alternative perfluorinated tail chemistries, PEG molecular weight and polydispersity, shorter hydrocarbon linkers (ethyl or methyl versus propyl), longer hydrocarbon spacers (C4 or higher), alternative counterions, such as monovalent anions, monovalent, polyatomic anions and di- or tri-valent counterions (to produce two or more tail fluorosurfactants). Further variables in the molecule structure include alternative linker chemistries (e.g., ether, ester, etc), alternative hydrophilic oligomers (e.g., polyalcohol, polyacrylamide, etc.), alternative quaternary ammonium cations, and alternative ionic groups (e.g., anionic terminus—carboxylate etc.; alternative cations).

The present invention is also directed to the coupling of PEG-diamines with carboxylic acid terminated perflouropolyether (Krytox 157) to form surfactants. Specifically, the present invention is directed to a fluorosurfactant molecule made by the ionic coupling of amine-terminated polyethyleneglycol (PEG-amine) with the carboxylic acid of DuPont Krytox perfluoropolyether (PFPE). The resulting structure conveys good performance in the stabilization of aqueous droplets in fluorinated oil in a microfluidic system. Preferred surfactants are described in WO 2008/021123. The present invention provides droplets with a fluorosurfactant interface separating the aqueous droplet and its contents from the surrounding immiscible fluorocarbon oil. In one example, DNA amplification reactions occurring inside these droplets generate material that does not interact with the channel walls, and collection of the DNA-containing droplets for subsequent manipulation and sequencing is straightforward. This technology provides a solution for amplification of DNA from single cells, allowing for both genotyping and whole genome amplification. In addition, use within a microfluidic device or platform as described herein achieves very high throughput, with droplets processed at rates in excess of 5000 droplets per second, enabling greater than $1 \times 10^6$ single-cell droplets to be formed and manipulated per hour.

Other examples of materials related to this invention include the formation of salts made by combination of various primary, secondary, or tertiary amines with PFPE carboxylic acid. The resulting amphiphilic structure could be useful as a stand-alone surfactant or a co-surfactant. Similarly, fluorinated materials with carboxylic acids other than Krytox PFPE could be used to form ionic fluorosurfactants with various amine containing compounds. Alternative amine-containing compounds for use with the present invention include, but are not limited to, PEG-monoamine (molecular weights range from 200 to 1,000,000 or more), PEG-diamine (molecular weights range from 200 to 1,000,000 or more), Multifunctional PEG amines (e.g., branched or dendritic structures), other hydrophilic polymers terminated with amines. Sugars include, but are not limited to, Sugars, Peptides, Biomolecules, Ethanolamine or Alkyl amines—primary, secondary, or tertiary (e.g., triethylamine, trimethylamine, methylamine, ethylamine, butylamine).

Alternative fluorinated groups for use with the present invention include, but are not limited to, Krytox FSL and FSM (alternative molecular weights), Demnum PFPE materials, Fluolink PFPE materials or Fluorinated small molecules with carboxylic acids.

The data described herein show that the fluorosurfactants comprised of PEG amine salts provide better performance (compared to other fluorosurfactants) for stabilization of aqueous droplets in fluorinated oils in droplet-based microfluidics applications. These novel surfactants are useful either in combination with other surfactants or as a stand-alone surfactant system.

Driving Forces

The invention can use pressure drive flow control, e.g., utilizing valves and pumps, to manipulate the flow of cells, particles, molecules, enzymes or reagents in one or more directions and/or into one or more channels of a microfluidic device. However, other methods may also be used, alone or in combination with pumps and valves, such as electro-osmotic flow control, electrophoresis and dielectrophoresis as described in Fulwyer, Science 156, 910 (1974); Li and Harrison, Analytical Chemistry 69, 1564 (1997); Fiedler, et al. Analytical Chemistry 70, 1909-1915 (1998) and U.S. Pat. No. 5,656,155. Application of these techniques according to the invention provides more rapid and accurate devices and methods for analysis or sorting, for example, because the sorting occurs at or in a sorting module that can be placed at or immediately after a detection module. This provides a shorter distance for molecules or cells to travel, they can move more rapidly and with less turbulence, and can more readily be moved, examined, and sorted in single file, i.e., one at a time.

Positive displacement pressure or other positive pressure driven flow is a preferred way of controlling fluid flow and dielectrophoresis is a preferred way of manipulating droplets within that flow. The pressure at the inlet module can also be regulated by adjusting the pressure on the main and sample inlet channels, for example, with pressurized syringes feeding into those inlet channels. By controlling the pressure difference between the oil and water sources at the inlet module, the size and periodicity of the droplets generated may be regulated. Alternatively, a valve may be placed at or coincident to either the inlet module or the sample inlet channel connected thereto to control the flow of solution into the inlet module, thereby controlling the size and periodicity of the droplets. Periodicity and droplet volume may also depend on channel diameter, the viscosity of the fluids, and shear pressure. Examples of driving pressures and methods of modulating flow are as described in WO 2006/040551; WO 2006/040554; WO 2004/002627; WO 2004/091763; WO 2005/021151; WO 2006/096571; WO 2007/089541; WO 2007/081385 and WO 2008/063227; U.S. Pat. No. 6,540,895 and U.S. Patent Application Publication Nos. 20010029983 and 20050226742.

Droplet Inlet

The microfluidic device of the present invention includes one or more inlet modules. An "inlet module" is an area of a microfluidic substrate device that receives molecules, cells, small molecules or particles for additional coalescence, detection and/or sorting. The inlet module can contain one or more inlet channels, wells or reservoirs, openings, and other features which facilitate the entry of molecules, cells, small molecules or particles into the substrate. A substrate may contain more than one inlet module if desired. Different sample inlet channels can communicate with the main channel at different inlet modules. Alternately, different sample inlet channels can communication with the main channel at the same inlet module. The inlet module is in fluid communication with the main channel. The inlet module generally comprises a junction between the sample inlet channel and the main channel such that a solution of a sample (i.e., a fluid containing a sample such as molecules, cells, small molecules (organic or inorganic) or particles) is introduced to the main channel and forms a plurality of droplets. The sample solution can be pressurized. The sample inlet channel can intersect the main channel such that the sample solution is introduced into the main channel at an angle perpendicular to a stream of fluid passing through the main channel. For example, the sample inlet channel and main channel intercept at a T-shaped junction; i.e., such that the sample inlet channel is perpendicular (90 degrees) to the main channel. However, the sample inlet channel can intercept the main channel at any angle, and need not introduce the sample fluid to the main channel at an angle that is perpendicular to that flow. The angle between intersecting channels is in the range of from about 60 to about 120 degrees. Particular exemplary angles are 45, 60, 90, and 120 degrees.

Embodiments of the invention are also provided in which there are two or more inlet modules introducing droplets of samples into the main channel. For example, a first inlet module may introduce droplets of a first sample into a flow of fluid in the main channel and a second inlet module may introduce droplets of a second sample into the flow of fluid in main channel, and so forth. The second inlet module is preferably downstream from the first inlet module (e.g., about 30 Inn). The fluids introduced into the two or more different inlet modules can comprise the same fluid or the same type of fluid (e.g., different aqueous solutions). For example, droplets of an aqueous solution containing an enzyme are introduced into the main channel at the first inlet module and droplets of aqueous solution containing a substrate for the enzyme are introduced into the main channel at the second inlet module. Alternatively, the droplets introduced at the different inlet modules may be droplets of different fluids which may be compatible or incompatible. For example, the different droplets may be different aqueous solutions, or droplets introduced at a first inlet module may be droplets of one fluid (e.g., an aqueous solution) whereas droplets introduced at a second inlet module may be another fluid (e.g., alcohol or oil).

Droplet Interdigitation

Particular design embodiments of the microfluidic device described herein allow for a more reproducible and controllable interdigitation of droplets of specific liquids followed by pair-wise coalescence of these droplets, described in further detail herein. The droplet pairs can contain liquids of different compositions and/or volumes, which would then combine to allow for a specific reaction to be investigated. The pair of droplets can come from any of the following: (i) two continuous aqueous streams and an oil stream; (ii) a continuous aqueous stream, an emulsion stream, and an oil stream, or (iii) two emulsion streams and an oil stream. The term "interdigitation" as used herein means pairing of droplets from separate aqueous streams, or from two separate inlet nozzles, for eventual coalescence.

Various nozzle designs enhance the interdigitation of droplets and further improves coalescence of droplets due to the better control of the interdigitation and smaller distance between pairs of droplets. The greater control over interdigitation allows for a perfect control over the frequency of either of the droplets. To obtain the optimum operation, the spacing between droplets and coupling of the droplets can be adjusted by adjusting flow of any of the streams, viscosity of the streams, nozzle design (including orifice diameter, the channel angle, and post-orifice neck of the nozzle). Examples of preferred nozzle designs are as described in WO 2007/081385 and WO 2008/063227.

Droplet Coalescence or Combination

The microfluidic device of the present invention also includes one or more coalescence modules. A "coalescence module" is within or coincident with at least a portion of the main channel at or downstream of the inlet module where molecules, cells, small molecules or particles comprised within droplets are brought within proximity of other droplets comprising molecules, cells, small molecules or particles and where the droplets in proximity fuse, coalesce or combine their contents. The coalescence module can also include an apparatus, for generating an electric force.

The electric force exerted on the fluidic droplet may be large enough to cause the droplet to move within the liquid. In some cases, the electric force exerted on the fluidic droplet may be used to direct a desired motion of the droplet within the liquid, for example, to or within a channel or a microfluidic channel (e.g., as further described herein), etc.

The electric field can be generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments. As used herein, "integral" means that portions of the components integral to each other are joined in such a way that the components cannot be in manually separated from each other without cutting or breaking at least one of the components.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof.

Preferred electrodes and patterned electrically conductive layers are described in WO 2007/081385 and WO 2008/063227 and can be associated with any module of the device (inlet module, coalescence module, mixing module, delay module, detection module and sorting module) to generate dielectric or electric forces to manipulate and control the droplets and their contents.

Effective control of uncharged droplets within microfluidic devices can require the generation of extremely strong dielectric field gradients. The fringe fields from the edges of a parallel plate capacitor can provide an excellent topology to form these gradients. The microfluidic device according to the present invention can include placing a fluidic channel between two parallel electrodes, which can result in a steep electric field gradient at the entrance to the electrodes due to edge effects at the ends of the electrode pair. Placing these pairs of electrodes at a symmetric channel split can allow precise bi-directional control of droplet within a device. Using the same principle, only with asymmetric splits, can allow single ended control of the droplet direction in the same manner. Alternatively, a variation on this geometry will allow precise control of the droplet phase by shifting.

Dielectrophoresis is believed to produce movement of dielectric objects, which have no net charge, but have regions that are positively or negatively charged in relation to each other. Alternating, non-homogeneous electric fields in the presence of droplets and/or particles, such as cells or molecules, cause the droplets and/or particles to become electrically polarized and thus to experience dielectrophoretic forces. Depending on the dielectric polarizability of the particles and the suspending medium, dielectric particles will move either toward the regions of high field strength or low field strength. For example, the polarizability of living cells depends on their composition, morphology, and phenotype and is highly dependent on the frequency of the applied electrical field. Thus, cells of different types and in different physiological states generally possess distinctly different dielectric properties, which may provide a basis for cell separation, e.g., by differential dielectrophoretic forces.

Likewise, the polarizability of droplets also depends upon their size, shape and composition. For example, droplets that contain salts can be polarized. According to formulas provided in Fiedler, et al. Analytical Chemistry 70, 1909-1915 (1998), individual manipulation of single droplets requires field differences (inhomogeneities) with dimensions close to the droplets.

The term "dielectrophoretic force gradient" means a dielectrophoretic force is exerted on an object in an electric field provided that the object has a different dielectric constant than the surrounding media. This force can either pull the object into the region of larger field or push it out of the region of larger field. The force is attractive or repulsive depending respectively on whether the object or the surrounding media has the larger dielectric constant.

Manipulation is also dependent on permittivity (a dielectric property) of the droplets and/or particles with the suspending medium. Thus, polymer particles, living cells show negative dielectrophoresis at high-field frequencies in water. For example, dielectrophoretic forces experienced by a latex sphere in a 0.5 MV/m field (10 V for a 20 micron electrode gap) in water are predicted to be about 0.2 piconewtons (pN) for a 3.4 micron latex sphere to 15 pN for a 15 micron latex sphere (Fiedler, et al. Analytical Chemistry, 70, 1909-1915 (1998)). These values are mostly greater than the hydrodynamic forces experienced by the sphere in a stream (about 0.3 pN for a 3.4 micron sphere and 1.5 pN for a 15 micron sphere). Therefore, manipulation of individual cells or particles can be accomplished in a streaming fluid, such as in a cell sorter device, using dielectrophoresis. Using conventional semiconductor technologies, electrodes can be microfabricated onto a substrate to control the force fields in a microfabricated sorting device of the invention. Dielectrophoresis is particularly suitable for moving objects that are electrical conductors. The use of AC current is preferred, to prevent permanent alignment of ions. Megahertz frequencies are suitable to provide a net alignment, attractive force, and motion over relatively long distances. See U.S. Pat. No. 5,454,472.

The electric field generator can be constructed and arranged (e.g., positioned) to create an electric field applicable to the fluid of at least about 0.01 V/micrometer, and, in some cases, at least about 0.03 V/micrometer, at least about 0.05 V/micrometer, at least about 0.08 V/micrometer, at least about 0.1 V/micrometer, at least about 0.3 V/micrometer, at least about 0.5 V/micrometer, at least about 0.7 V/micrometer, at least about 1 V/micrometer, at least about 1.2 V/micrometer, at least about 1.4 V/micrometer, at least about 1.6 V/micrometer, or at least about 2 V/micrometer. In some embodiments, even higher electric field intensities may be used, for example, at least about 2 V/micrometer, at least about 3 V/micrometer, at least about 5 V/micrometer, at least about 7 V/micrometer, or at least about 10 V/micrometer or more. As described, an electric field may be applied to fluidic droplets to cause the droplets to experience an electric force. The electric force exerted on the fluidic droplets may be, in some cases, at least about $10^{-16}$ N/micrometer$^3$. In certain cases, the electric force exerted on the fluidic droplets may be greater, e.g., at least about $10^{-15}$ N/micrometer$^3$, at least about $10^{-14}$ N/micrometer$^3$, at least about $10^{-13}$ N/micrometer$^3$, at least about $10^{-12}$ N/micrometer$^3$, at least about $10^{-11}$ N/micrometer$^3$, at least about $10^{-10}$ N/micrometer$^3$, at least about $10^{-9}$ N/micrometer$^3$, at least about $10^4$ N/micrometer$^3$, or at least about $10^{-7}$ N/micrometer$^3$ or more. The electric force exerted on the fluidic droplets, relative to the surface area of the fluid, may be at least about $10^{-15}$ N/micrometer$^2$, and in some cases, at least about $10^{-14}$ N/micrometer$^2$, at least about $10^{-13}$ N/micrometer$^2$, at least about $10^{-12}$ N/micrometer$^2$, at least about $10^{-11}$ N/micrometer$^2$, at least about $10^m$ N/micrometer$^2$, at least about $10^{-9}$ N/micrometer$^2$, at least about $10^{-8}$ N/micrometer$^2$, at least about 1e N/micrometer$^2$, or at least about $10^{-6}$ N/micrometer$^2$ or more. In yet other embodiments, the electric force exerted on the fluidic droplets may be at least about $10^{-9}$ N, at least about $10^4$ N, at least about $10^{-7}$ N, at least about $10^{-6}$ N, at least about $10^{-5}$ N, or at least about $10^{-4}$ N or more in some cases.

Binding Agents, Solid Supports, and Washing

Methods of the invention involve use of first and second binding agents (also called 'binders') that can bind to the target analyte to form a sandwich complex. The first and second binding agents have specificity for different binding sites on the same target analyte, i.e., the first and second binding agents bind different parts of the target analyte, where the analyte can be a single molecule or a stable complex of molecules. The binding agents may be any molecules that specifically bind to a target analyte in the sample. Exemplary binding agents include an antibody, an oligonucleotide, any protein based or nucleic acid based binding agent, or any agent capable of attaching to target analytes. Further binding agents embodied in methods of the invention include DNA, RNA, LNA (locked nucleic acids), PNA (peptide nucleic acid), a ligand, an irreversible inhibiting small molecule, a metabolite, a lipid, a sugar, a synthetic polymer, or other non-peptide or nucleic acid-based binding agent, or combinations of the above.

In certain embodiments, the binding agent is an antibody. General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen effective to produce an immune response. An exemplary protocol is as follows. The animal is injected with 100 milligrams of antigen resuspended in adjuvant, for example Freund's complete adjuvant, dependent on the size of the animal, followed three weeks later with a subcutaneous injection of 100 micrograms to 100 milligrams of immunogen with adjuvant dependent on the size of the animal, for example Freund's incomplete adjuvant. Additional subcutaneous or intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing protein G resin or target-specific affinity resin.

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4):145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

In certain embodiments, the binding agent is an aptamer. As used herein, "aptamer" and "nucleic acid ligand" are used interchangeably to refer to a nucleic acid that has a specific binding affinity for a target molecule, such as a protein. Like all nucleic acids, a particular nucleic acid ligand may be described by a linear sequence of nucleotides (A, U, T, C and G), typically 15-40 nucleotides long. Nucleic acid ligands can be engineered to encode for the complementary sequence of a target protein known to associate with the presence or absence of a specific disease.

In solution, the chain of nucleotides form intramolecular interactions that fold the molecule into a complex three-dimensional shape. The shape of the nucleic acid ligand allows it to bind tightly against the surface of its target molecule. In addition to exhibiting remarkable specificity, nucleic acid ligands generally bind their targets with very high affinity, e.g., the majority of anti-protein nucleic acid ligands have equilibrium dissociation constants in the picomolar to low nanomolar range.

Aptamers used in the compositions of the invention depend upon the target tissue. Nucleic acid ligands may be discovered by any method known in the art. In one embodiment, nucleic acid ligands are discovered using an in vitro selection process referred to as SELEX (Systematic Evolution of Ligands by Exponential enrichment). See for example Gold et al. (U.S. Pat. Nos. 5,270,163 and 5,475,096), the contents of each of which are herein incorporated by reference in their entirety. SELEX is an iterative process used to identify a nucleic acid ligand to a chosen molecular target from a large pool of nucleic acids. The process relies on standard molecular biological techniques, using multiple rounds of selection, partitioning, and amplification of nucleic acid ligands to resolve the nucleic acid ligands with the highest affinity for a target molecule. The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. There have been numerous improvements to the basic SELEX method, any of which may be used to discover nucleic acid ligands for use in methods of the invention.

In certain embodiments, the binding agent is an oligonucleotide. Methods of synthesizing oligonucleotides are known in the art. See, e.g., Sambrook et al. (DNA microarray: A Molecular Cloning Manual, Cold Spring Harbor, N.Y., 2003) or Maniatis, et al. (Molecular Cloning: A Laboratory Manual, Cold Spring Harbor, N.Y., 1982), the contents of each of which are incorporated by reference herein in their entirety. Suitable methods for synthesizing oligonucleotide probes are also described in Caruthers (Science 230:281-285, 1985), the contents of which are incorporated by reference. Oligonucleotides can also be obtained from commercial sources such as Operon Technologies, Amersham Pharmacia Biotech, Sigma, and Life Technologies. The oligonucleotides can have an identical melting temperature. The lengths of the probes can be extended or shortened at the 5' end or the 3' end to produce oligonucleotides with desired melting temperatures. Also, the annealing position of each oligonucleotide can be designed such that the sequence and length of the probe yield the desired melting temperature. The simplest equation for determining the melting temperature of probes smaller than 25 base pairs is the Wallace Rule ($Td=2(A+T)+4(G+C)$). Computer programs can also be used to design oligonucleotides, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting temperature) of each probe is calculated using software programs such as Oligo Design, available from Invitrogen Corp.

In certain embodiments, the oligonucleotides can include two portions, a portion that includes a nucleotide sequence with substantial complementarity to a target analyte, so that the oligonucleotide hybridizes with the target analyte. The oligonucleotides can also include a universal region, i.e., a synthetic sequence that is not found in the genome of the organism of interest and that is identical in all of the oligonucleotides. The universal sequence may be a homopolymer, e.g., poly(A) or may be a sequence composed of many different bases. The universal region of the oligonucleotides is useful as a primer site for conducting secondary enzymatic reactions to link any number of sequence based or chemical moieties that are relevant to downstream processing and analysis.

Oligonucleotides suitable for use in the present invention include those formed from nucleic acids, such as RNA and/or DNA, nucleic acid analogs, locked nucleic acids, modified nucleic acids, and chimeric probes of a mixed class including a nucleic acid with another organic component such as peptide nucleic acids. Exemplary nucleotide analogs include phosphate esters of deoxyadenosine, deoxycytidine, deoxyguanosine, deoxythymidine, adenosine, cytidine, guanosine, and uridine. Other examples of non-natural nucleotides include a xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, and any other structural moiety that can act substantially like a nucleotide or base, for example, by exhibiting base-complementarity with one or more bases that occur in DNA or RNA. Also included are nucleotides modified for use in photo-activated ligation or cleavage, e.g. 4-thiothymidine, 1-[2-Nitro-5-(6-trifluoroacetylcaproamidomethyl)phenyl]-ethyl-[2-cyano-ethyl-(N,N-diisopropyl)]-phosphoramidite, 5-carboxyvinyl-2'-deoxyuridine.

The length of the nucleic acid binding agents are not critical, as long as they are capable of specific binding to the target regions. In fact, oligonucleotides may be of any length. For example, oligonucleotides may be as few as 5 nucleotides, or as much as 5000 nucleotides. Exemplary oligonucleotides are 5-mers, 10-mers, 15-mers, 20-mers, 25-mers, 50-mers, 100-mers, 200-mers, 500-mers, 1000-mers, 3000-mers, or 5000-mers. Methods for determining an optimal oligonucleotides length are known in the art. See, e.g., Shuber (U.S. Pat. No. 5,888,778). The first and second binding agents do not have to be of the same length. In certain embodiments, the first and second binding agents are the same length, while in other embodiments, the first and second binding agents are of different lengths.

Figure 7:
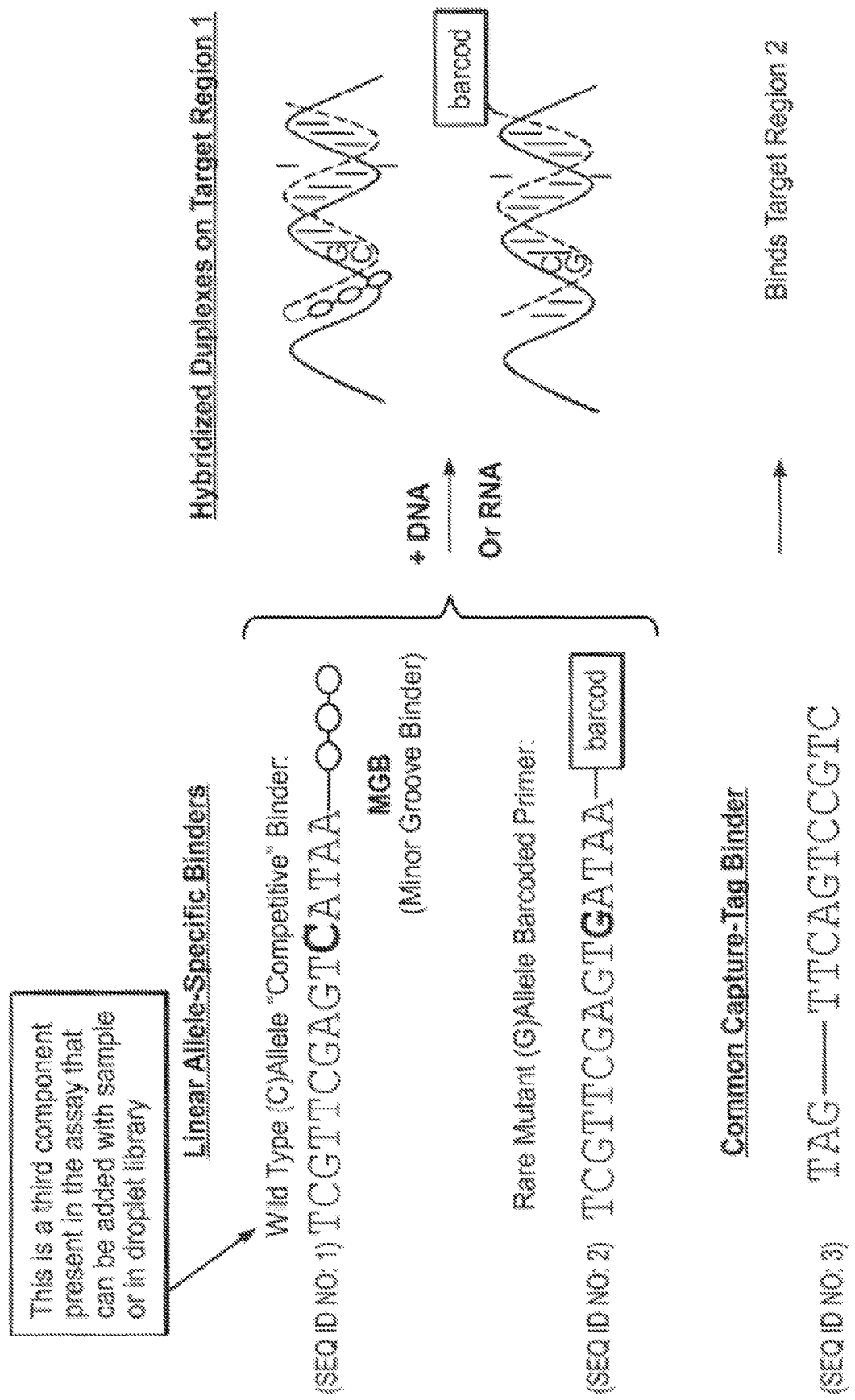
FIG. 7 depicts a competitive inhibitor from one embodiment of the invention.

In certain embodiments, a competitive inhibitor is introduced to the droplet library or the sample in order to enhance the specificity of the isolated sandwich formation. In some embodiments, the sample contains target analytes and unspecific analytes similar to the target analytes which may result in a false positive connection between the binding agent specific to the target analyte and the unspecific analyte. If a false positive connection is made, the representative value of the identifiers to the target analyte reduces in specificity. In one embodiment unspecific nuclei acid analytes may contain a sequence with a single base difference in a sequence. Unspecific analytes include any difference from a target protein or nucleic acid or other target analyte that would result in an affinity of the target analyte identifier to the unspecific analyte. FIG. 7 depicts a non-limiting embodiment of the use of a competitive inhibitor to prevent a binding agent with an identifier and, or a capture molecule from binding to a competitive unspecific analyte, wild type (C) allele, within the sample, when the target analyte is a rare mutant (G) allele. In the FIG. 7 embodiment, the competitive inhibitor includes a minor groove binder motif that increases the affinity to the wild type unspecific analyte, and binds to the unspecific analyte prior to the target analyte specific binding agent, or competes the target analyte specific binding agent off. Methods of the invention provide for the competitive inhibitor to be DNA, RNA, PNA, and LNA, and any other nucleic acid, or protein, or other binding agents capable of preventing false positive attachment to a unspecific analyte. The competitive molecules can be included in the sample, the droplet library, or both.

Generally, the second binding agent (also called the 'capture-tagged binder') is configured such that it can be coupled to a solid support in either a reversible or irreversible manner. For example, a terminal portion of the second binding agent may be functionalized with a terminal amine such that it can covalently bind an epoxide coated surface. The terminal amine that can form a covalent bond with an epoxide coated bead. In this embodiment, the epoxide coated bead is introduced to the binding agent now bearing an amine group. The highly-reactive epoxide ring opens, and a reactive carbon binds to the amine group on the copy. Further description of amine attachment is shown for example in Harris et al. (U.S. Pat. No. 7,635,562; Joos et al., Analytical Biochemistry 247:96-101, 1997; Oroskar et al., Clin. Chem. 42:1547-1555, 1996; and Khandjian, Mol. Bio. Rep. 11:107-115, 1986, the content of each of which is incorporated by reference herein in its entirety.

Alternatively, a part of the second binding agent is functionalized with one member of a binding pair while a surface of the solid support is functionalized with the other member of the binding pair (e.g., biotin/avidin; biotin/streptavidin/or digoxigenin/anti-digoxigenin). The second binding agent, now functionalized with a member of the binding pair (i.e., member of a capture tag pair) is brought into proximity of the solid support coated with the other member of the binding pairs. The two members of the binding pair interact to immobilize the complexes onto the solid support. See Harris et al. U.S. Pat. No. 7,635,562; Taylor et al., J. Phys. D. Appl. Phys. 24:1443, 1991); and Smith et al., Science 253:1122, 1992, the content of each of which is incorporated by reference herein in its entirety. Additional stringency can be provided through using tandem binding motif pairs.

Exemplary couplings include but are not limited to 1) a biotin capture tag for use with a streptavidin, avidin, or alternative modified derivatives of streptavidin or avidin solid supports; 2) a desthiobiotin capture tag for use with a streptavidin, avidin, or alternative modified derivatives of streptavidin or avidin solid support; 3) a antigen capture tag including FLAG, hemagglutinin, calmodulin-binding domain, histidine multimers, or other common epitope tags for use with their cognate binding partners including anti-FLAG, anti-hemagglutinin, anti-calmodulin as the solid support. Further couplings embodied in the invention include metal-binding domains for binding histidine-tags, or binders targeting other binders e.g. antibodies bound to other antibodies or antibody-binders like Protein A/G.

In certain non-limiting embodiments, various formats are used to attach the capture tags to a bead, or other solid support. Several embodiments for coupling include, but are not limited to 1) the capture tag attaches to beads present in the droplet library; 2) the capture tag attaches to beads present in sample droplets; 3) the capture tag attaches to beads after release of the combined droplet contents; and 4) the capture tag attaches on a well plate after release of the combined droplet contents.

In some embodiments of the invention, the target analyte sandwich is isolated from the unbound sample components without the use of capture tags or immobilization to a stable support. Such embodiments include but are not limited to using magnetic energy, chemical reactions, pressurized separation with shear stress, or any other system capable of isolating target analyte sandwiches with specificity to allow for analyzing only the target analyte. The preferred embodiment of the invention utilizes capture molecules having capture tags for binding to a stable support.

The support may be a bead that is present in the droplet or it may be a support outside of the droplet. Supports for use in the invention can be two- or three-dimensional and can comprise a planar surface (e.g., a glass slide) or can be shaped. A support substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, composites, or other materials.

Suitable three-dimensional supports include, for example, spheres, microparticles, beads, membranes, slides, plates, micromachined chips, tubes (e.g., capillary tubes), microwells, microfluidic devices, channels, filters, or any other structure suitable for anchoring the capture-tagged binder. Supports can include planar arrays or matrices capable of having regions that include populations of nucleic acids, peptides, sugars, or other molecules. Examples include nucleoside-derivatized CPG and polystyrene slides; derivatized magnetic slides; polystyrene grafted with polyethylene glycol, and the like.

Once the immobilization step occurs such that the sandwich is bound to the solid support, a wash step is performed to isolate sandwich complexes bound to the solid support from remaining components in the sample. In one embodiment, a wash buffer may have sufficient stringency to remove the unincorporated binders and unincorporated non-specific analytes without disrupting the sandwich. In certain embodiments, the wash may just impose a shear stress to remove unwanted and unattached sample and binding elements, however a wash containing binding elements specific to the unwanted sample may increase specificity in the target analyte analysis.

Target Identifier and Sample Identifier Molecules

Generally, the first binding agent, also called the 'barcoded binder', includes an identifier molecule, i.e., a target identifier. The target identifier molecule may be any molecule that is differentially detectable by any detection techniques known in the art. Exemplary detection methods include radioactive detection, optical absorbance detection, e.g., UV-visible absorbance detection, optical emission detection, e.g., fluorescence; phosphorescence or chemiluminescence; Raman scattering, magnetic detection, or mass spectral detection. In certain embodiments, the identifier is an optically detectable label, such as a fluorescent label. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Atto dyes, Cy3; Cy5; Cy5.5; Cy7; IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels.

Fluorescently labeled nucleotides may be produced by various techniques, such as those described in Kambara et al. (Bio/Technol., 6:816-21, 1988); Smith et al. (Nucl. Acid Res., 13:2399-2412, 1985); and Smith et al. (Nature, 321: 674-679, 1986). The fluorescent dye may be linked to the deoxyribose by a linker arm that is easily cleaved by chemical or enzymatic means. There are numerous linkers and methods for attaching labels to nucleotides, as shown in Oligonucleotides and Analogues: A Practical Approach (IRL Press, Oxford, 1991); Zuckerman et al. (Polynucleotides Res., 15: 5305-5321, 1987); Sharma et al. (Polynucleotides Res., 19:3019, 1991); Giusti et al. (PCR Methods and Applications, 2:223-227, 1993); Fung et al. (U.S. Pat. No. 4,757,141); Stabinsky (U.S. Pat. No. 4,739,044); Agrawal et al. (Tetrahedron Letters, 31:1543-1546, 1990); Sproat et al. (Polynucleotides Res., 15:4837, 1987); and Nelson et al. (Polynucleotides Res., 17:7187-7194, 1989). Extensive guidance exists in the literature for derivatizing fluorophore and quencher molecules for covalent attachment via common reactive groups that may be added to a nucleotide. Many linking moieties and methods for attaching fluorophore moieties to nucleotides also exist, as described in Oligonucleotides and Analogues, supra; Guisti et al., supra; Agrawal et al, supra; and Sproat et al., supra.

In other embodiments, the target identifier is a sequence of oligonucleotides that constitutes a unique identifier, or barcode. Attaching barcode sequences to other molecules, such as nucleic acids, is shown for example in Kahvejian et al. (U.S. patent application number 2008/0081330), and Steinman et al. (International patent application number PCT/US09/64001), the content of each of which is incorporated by reference herein in its entirety. Methods for designing sets of barcode sequences and other methods for attaching barcode sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6172,218; and 5,863,722, the content of each of which is incorporated by reference herein in its entirety. In certain embodiments, a single barcode is attached to each identifier. In other embodiments, a plurality of barcodes, e.g., two barcodes, are attached to each identifier.

In certain embodiments, the barcode identifier can include features that make it useful in nucleic acid sequencing reactions. For example the barcode sequences are designed to have minimal or no homopolymer regions, i.e., 2 or more of the same base in a row such as AA or CCC, within the barcode sequence.

Methods of designing sets of nucleic acid barcode sequences is shown for example in Brenner et al. (U.S. Pat. No. 6,235,475), the contents of which are incorporated by reference herein in their entirety. In certain non-limiting embodiments, the barcode sequences range from about 4 nucleotides to about 25 nucleotides. In a particular embodiment, the barcode sequences range from about 4 nucleotides to about 7 nucleotides.

When the first binding agent is a nucleic acid, the barcode sequence can be attached to the nucleic acid with an enzyme, or the entire nucleic acid can be synthesised. The enzyme may be a ligase or a polymerase. The ligase may be any enzyme capable of ligating an oligonucleotide (RNA or DNA) to the nucleic acid molecule. Suitable ligases include T4 DNA ligase and T4 RNA ligase (such ligases are available commercially, from New England Biolabs). Methods for using ligases are well known in the art. The polymerase may be any enzyme capable of adding nucleotides to the 3' and the 5' terminus of template nucleic acid molecules. Photo-ligation, chemical attachment, or other methods may also be used to attach the barcode sequence to the nucleic acid-based binder. Non-covalent attachment methods may also be used. One embodiment uses hybridization of complimentary oligonucleotides, between a nucleic acid covalently attached to the first binding agent and an oligonucleotide containing a target identifier.

The target identifier may be coupled to the first binding agent in a releasable manner, such that the identifier may be separated from the first binding agent for purposes of detection in certain embodiments. Alternatively, the target identifier is irreversibly coupled to the first binding agent and detection of the identifier occurs on the complex with the analyte.

In one embodiment for attachment, a modified terminal oligonucleotide is incorporated to the end of an oligonucleotide-encoded identifier. The incorporation may include attaching a UV photo-cleavable primary amino group onto the 5' end of the oligonucleotide binding agent, and subsequently directly attaching the identifier to a protein based binding agent via the amino group. In another embodiment, a UV photo-cleavable oligonucleotide is incorporated into a nucleic acid based binding agent.

Further attachment strategies involve using a bi-functional cross-linking reagent to directly attach an amino acid containing binding agent to an oligonucleotide-based identifier. Embodiments of the method include indirect method attachments, including but not limited to, hybridizing, or annealing, an oligonucleotide identifier to a complimentary oligonucleotide that is either linked to a protein-based binding agent, or incorporated in the sequence of a nucleic acid-based binding agents. Other formats or combinations of the above may also be included, such as attaching a biotinylated or desthiotinylated barcoded oligonucleotide bound to a streptavidin-modified binding agent; attaching DIG, dye, or biotinylated identifying oligonucleotide bound to an antibody to the same motifs bound to the binding agent; and other dimerization motifs, including protein-based nucleic acid-based, or chemical based. Other attachment strategies may be used for protein, nucleic acid, or non-protein or non-nucleic acid binding agents (e.g. chemical modification of lipids, sugars, or synthetic small molecules).

Methods of the invention provide for releasing identifiers isolated after the unbound sample components are removed in the wash. The identifier may be released from the target analyte sandwich using a variety of methods including but not limited to 1) Light-induced release, for example UV-induced photocleavage; 2) Enzymatic release, for example restriction endonuclease, exonuclease, protease; 3) Chemical induced release, for example. metal-catalyzed oxidation; 4) Temperature-induced release, for example release of annealed oligonucleotide; and 5) combinations of the above releasing methods.

Figure 5A:
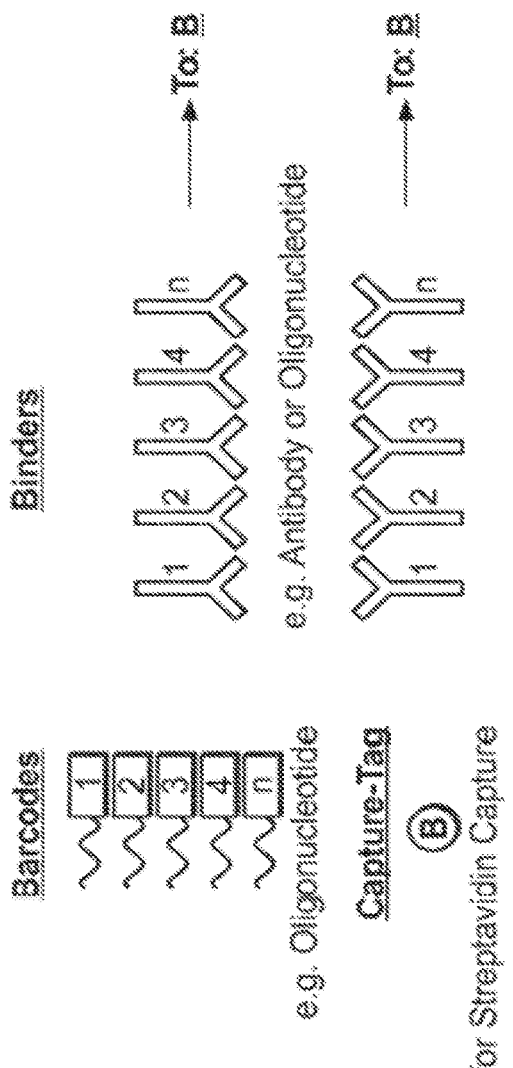
FIGS. 5A-B are a schematic illustrating an embodiment of the invention for preparing, attaching, and releasing identifiers for analyzing target analytes.
Figure 5A:
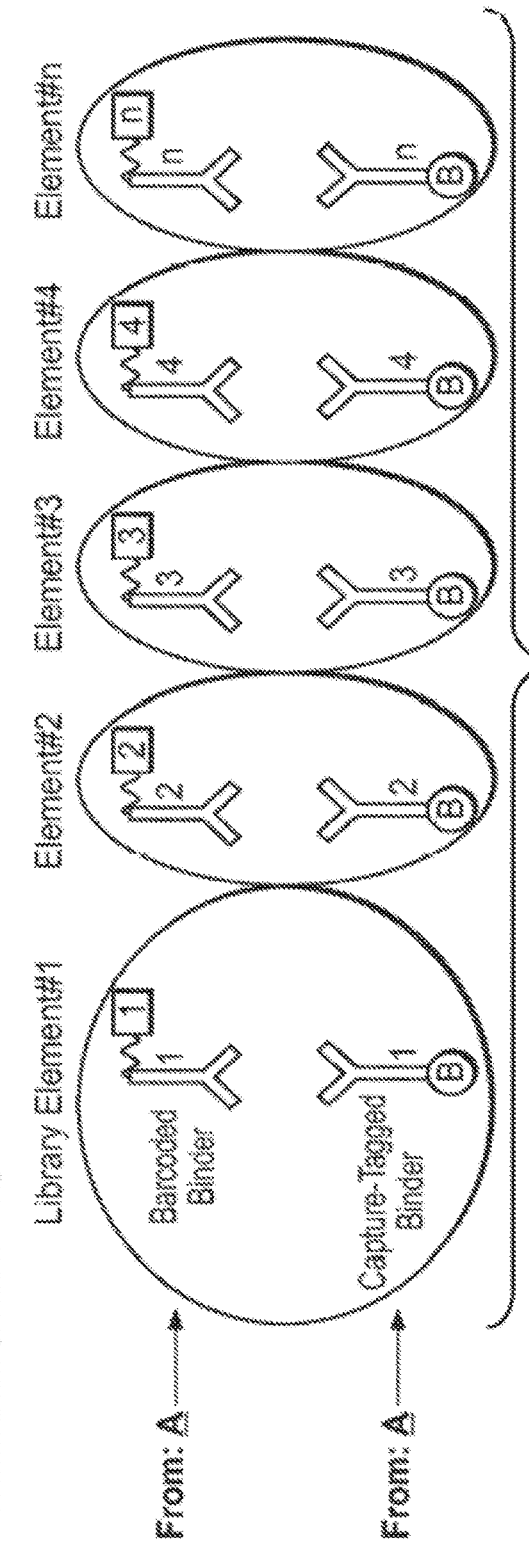
Figure 5B:
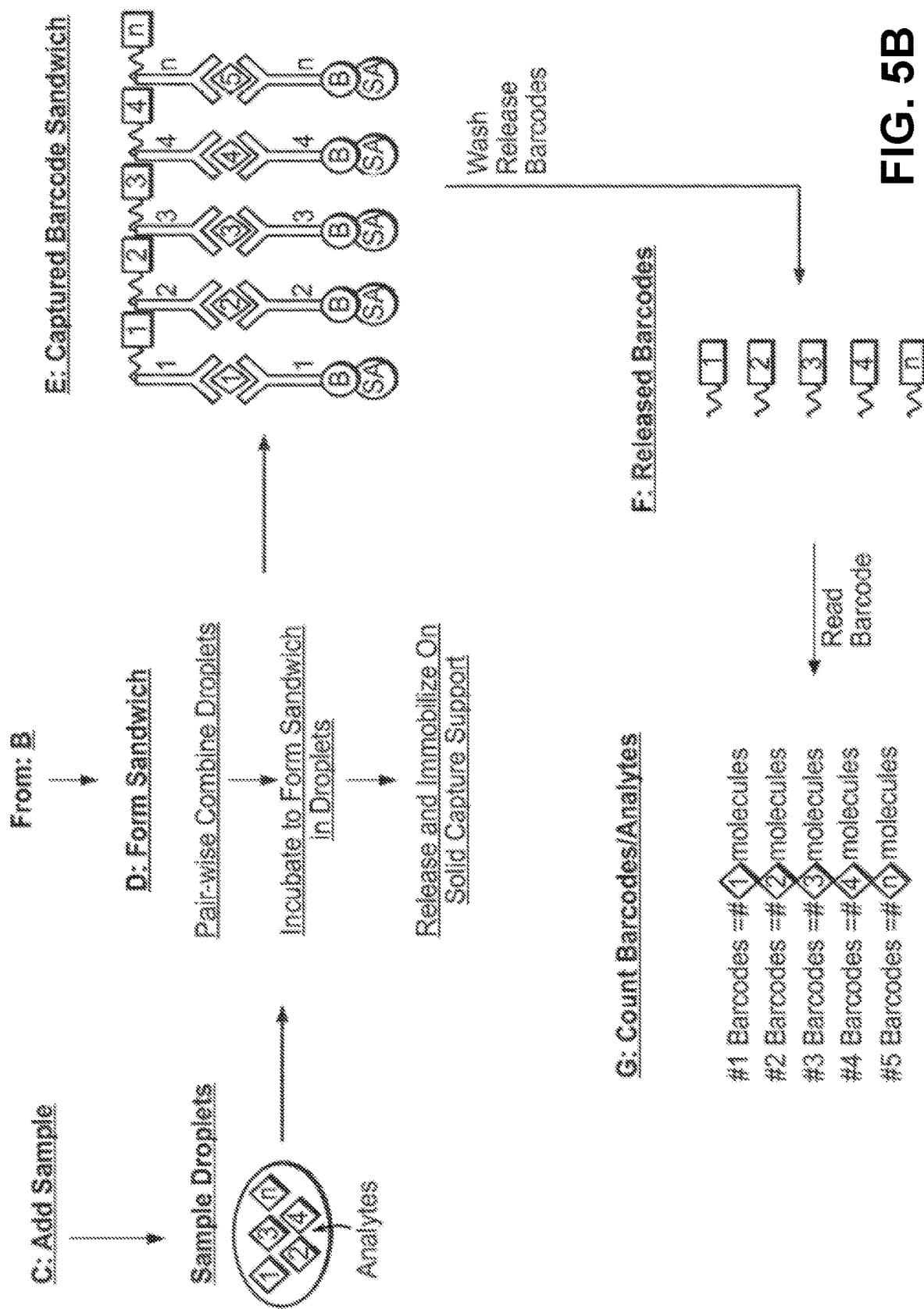
Figure 6A:
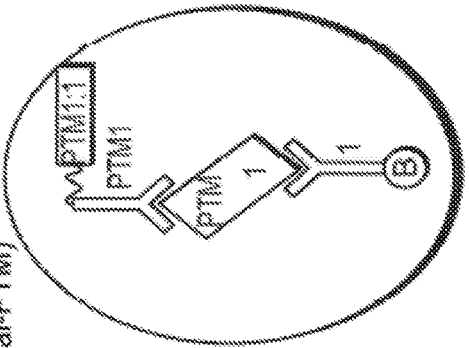
FIGS. 6A-J depict target analyte sandwiches with identifiers embodying principles of the invention.
Figure 6B:
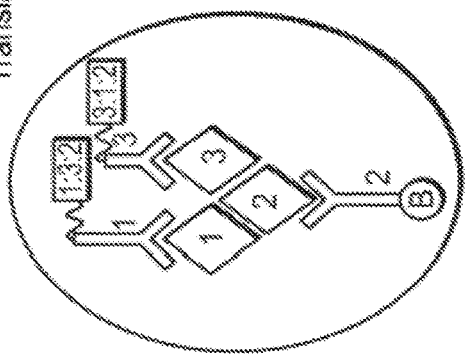
Figure 6C:
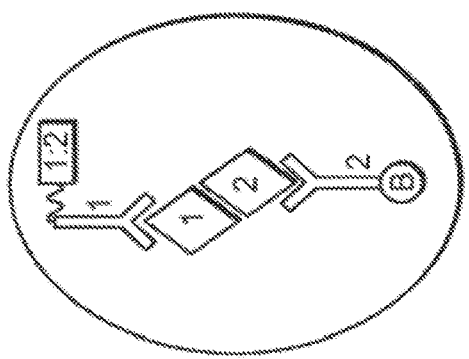
Figure 6D:
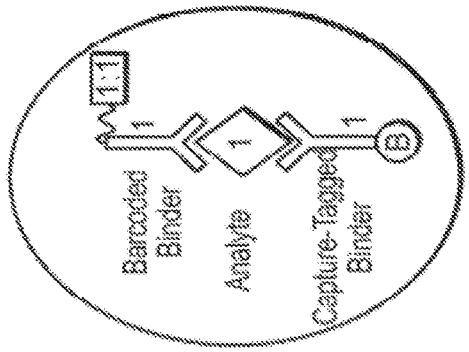
Figure 6E:
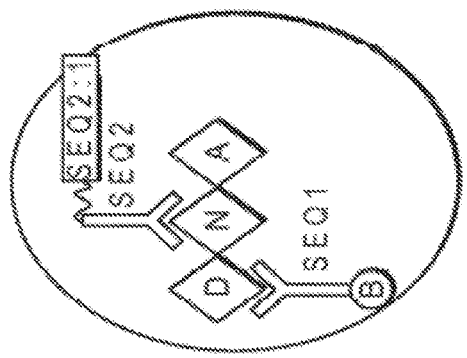
Figure 6F:
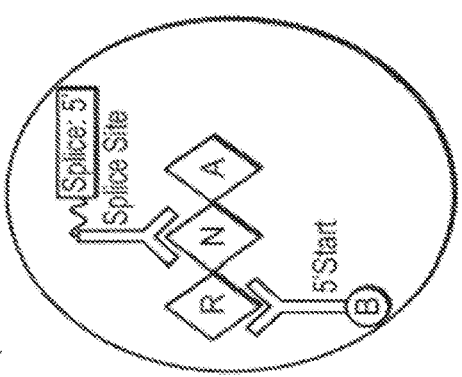
Figure 6G:
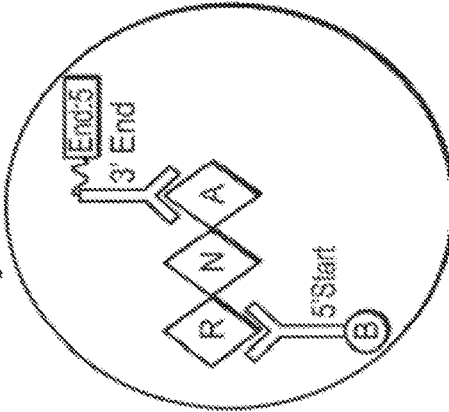
Figure 6H:
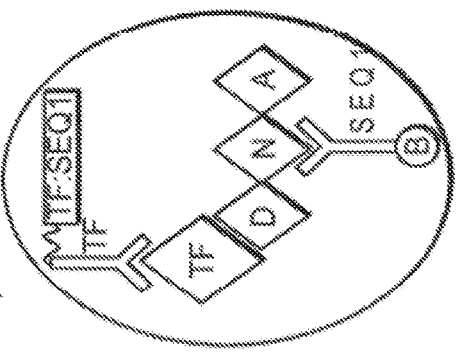
Figures 6I, 6J:
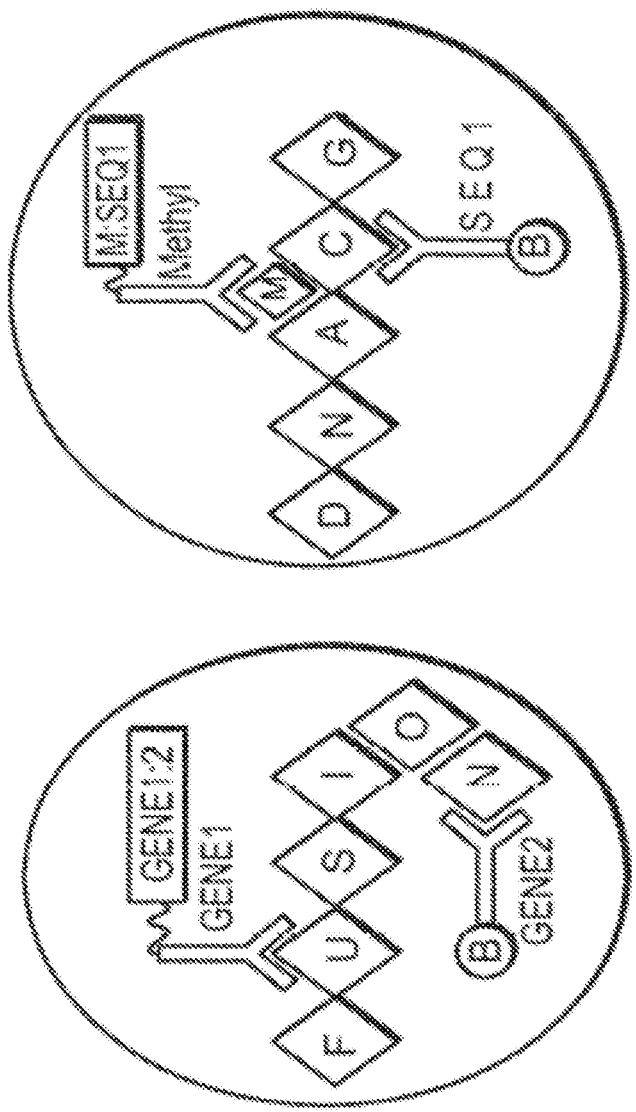

Methods of the invention provide for a capture-tagged binding molecule to correspond with the binding agent having the target identifier, as they are co-encapsulated first in the droplet library element, and subsequently after combination with a sample droplet. The capture molecule and binding agent are considered partner pairs because both are specific to a target analyte and will create a sandwich assay in the presence of the analyte. The barcode identifiers are designed such that each barcode is directly correlated to a particular set of binding agents that are placed together in a single droplet library element for binding a particular target analyte. This allows barcode reads to be correlated back to the binding agents, and thus the target analyte for quantification. Examples of this encoding strategy are shown in FIGS. 5A-B and 6A-J. In FIGS. 5A-B, A) Two binding reagents types are constructed: Barcoded Binders and Capture-Tag Binders; B) Pairs of target-specific binders are made into a droplet library, with each set of target binders in separate droplets; C) The sample is made into sample droplets, and D) combined with the library droplets to initiate highly parallel 'single-plex' binding reactions. After binding is complete, productive sandwiches are E) captured via the capture-tag (streptavidin (SA) biotin (B) interaction shown), and washed to remove unbound material; F) The captured barcodes are released, recovered, and processed for reading; G) Reads for each barcode are counted (e.g. using sequencing). In FIG. 6A, A binder pair targeting two different regions of the same analyte enable counting single target analytes; FIG. 6B & FIG. 6C), Binder pairs targeting different analytes in a complex enable identification and digital quantification of analyte complexes; FIG. 6D) A binder pair targeting two different regions of the same analyte, with one target being a specific modification (e.g. protein post-translational); FIG. 6E) Cross-linked or stable complexes can be analyzed (e.g. protein-nucleic acid); FIGS. 6F-J) Identification and counting of various nucleic acid molecules and motifs are shown (detailed descriptions in the text). Note that the Binder Barcode information includes details on which binders are in the library droplet (e.g. "3:1:2" in example C means Binder3 in the same droplet as Binder1 and Capture-Tag Binder2)

In some embodiments of the invention, the capture molecule may have its own or similar identifier to the corresponding identifier attached to the binding agent to use for quantification. In one embodiment, the control identifiers are read after a separate release step.

Figure 8A:
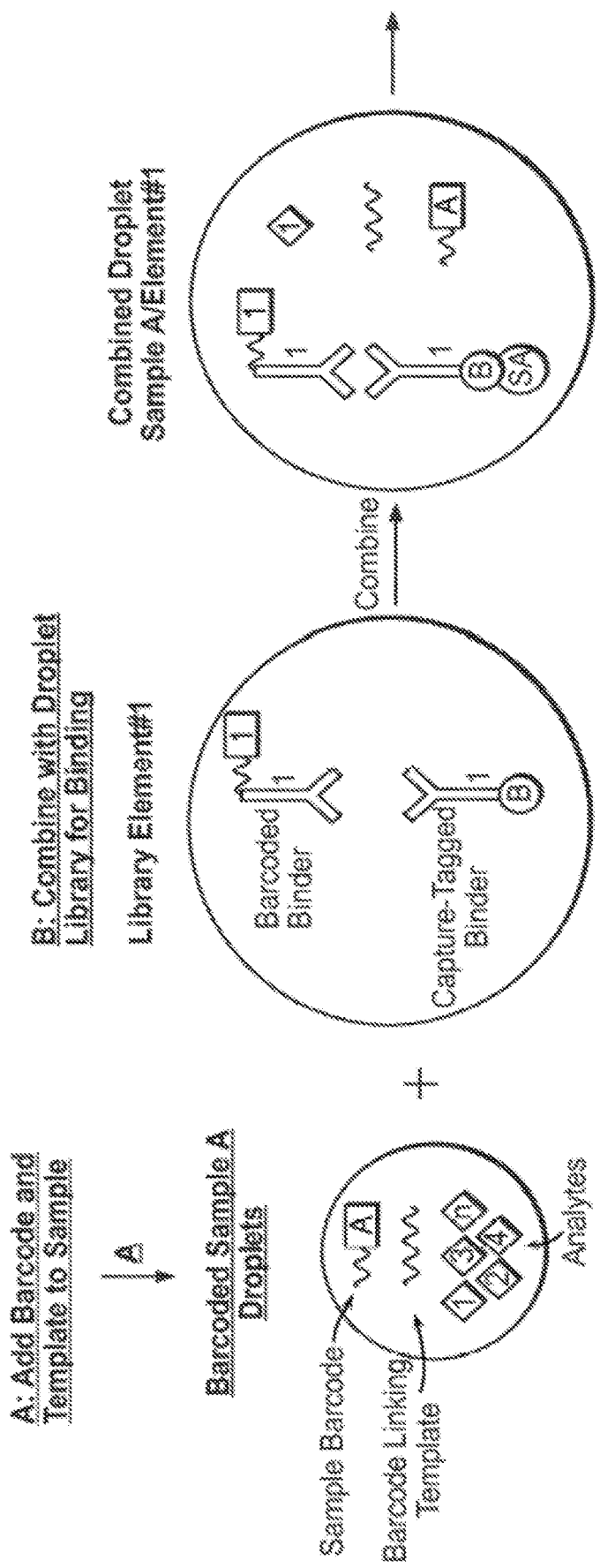
FIGS. 8A-B depict introducing a sample identifier to a target analyte identifier in one embodiment of the invention.
Figure 8B:
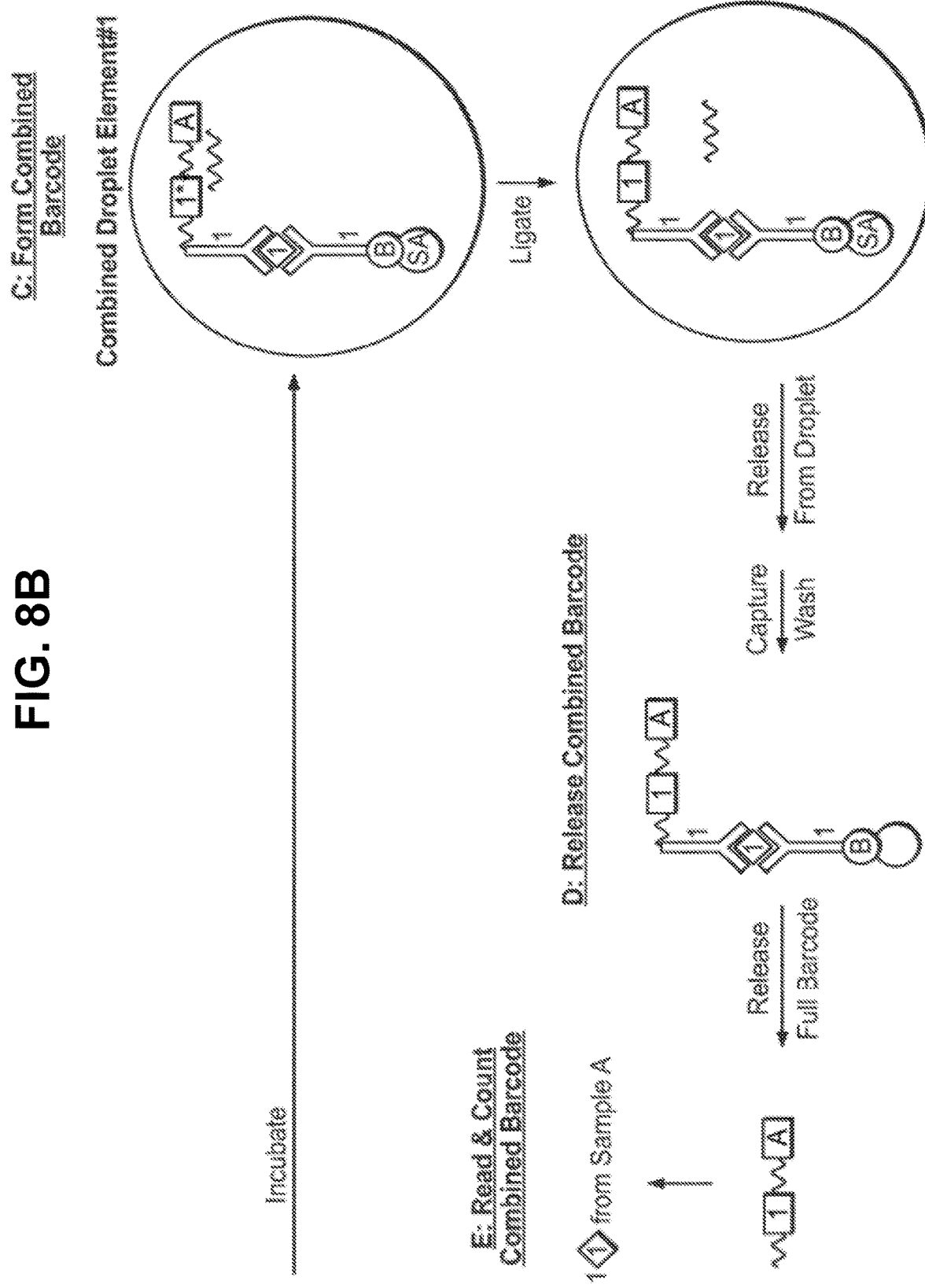
Figure 9A:
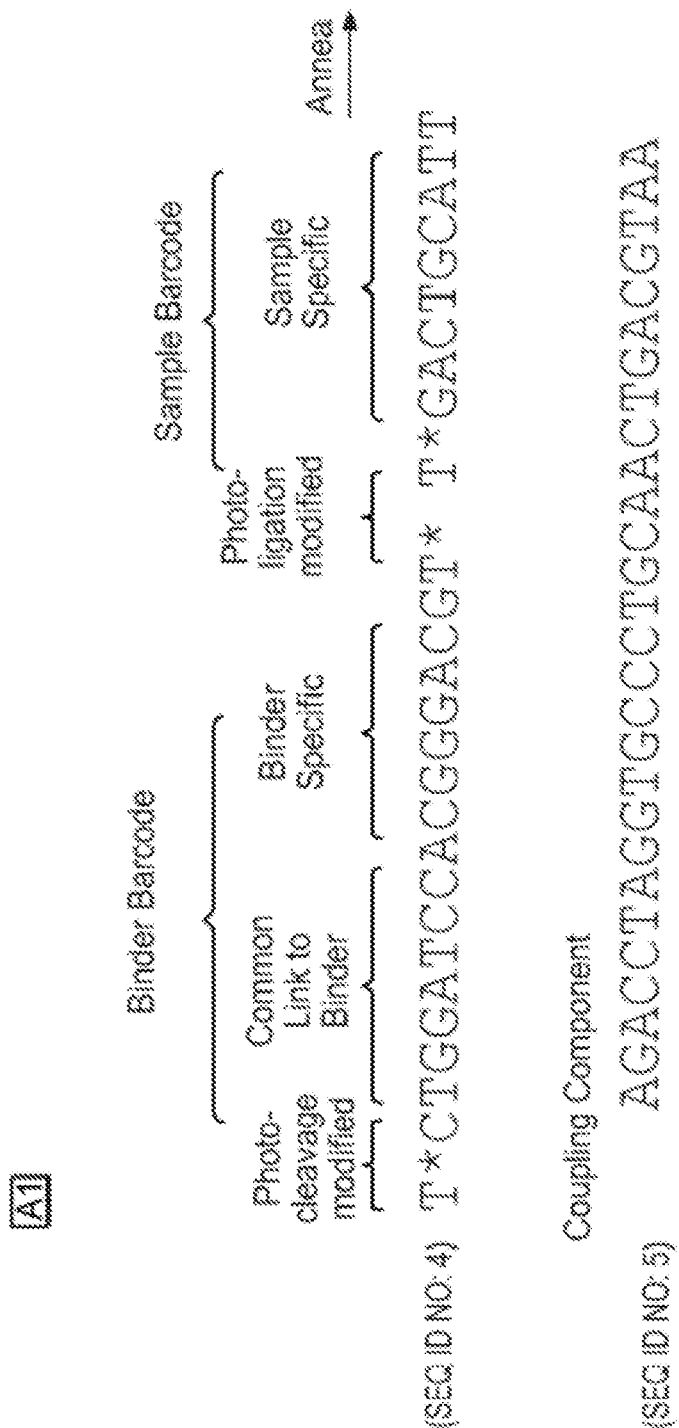
FIGS. 9A through 9C and FIGS. 10A through 10C depict binding of a sample identifier to a target analyte identifier in one embodiment of the invention.
Figure 9B:
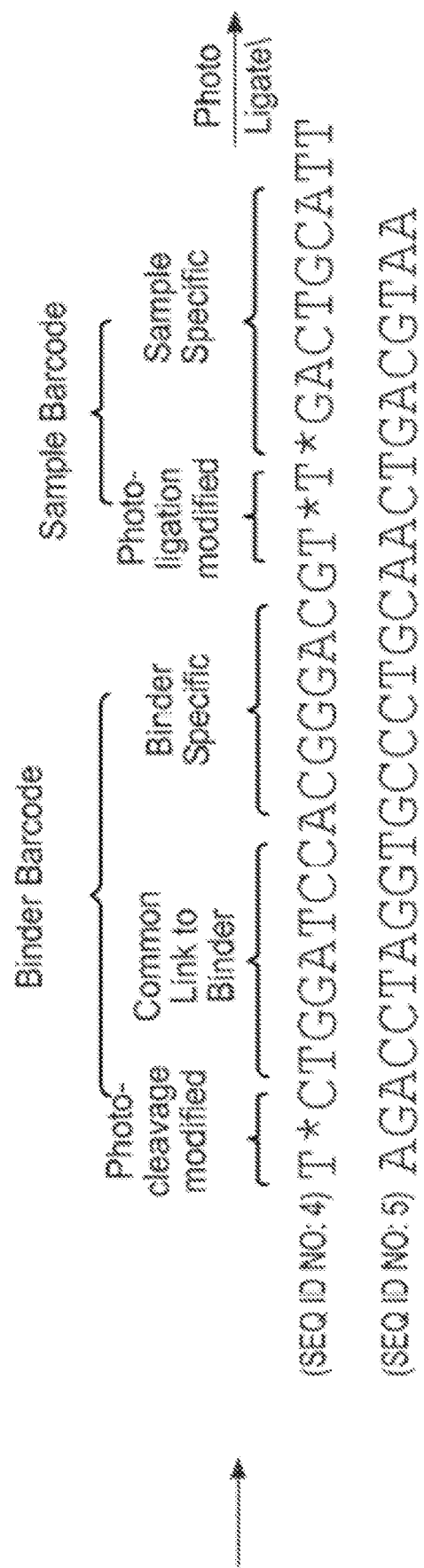
Figure 9C:
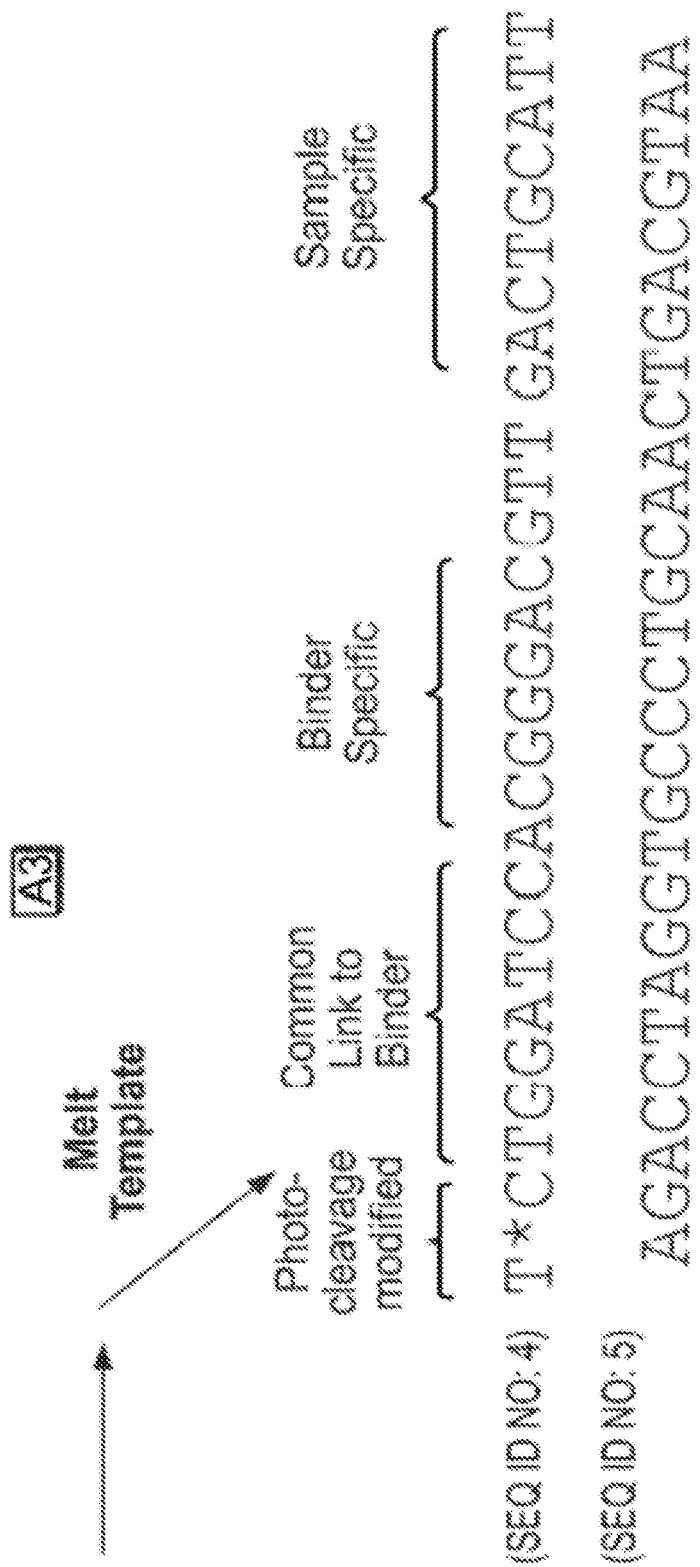
Figure 10A:
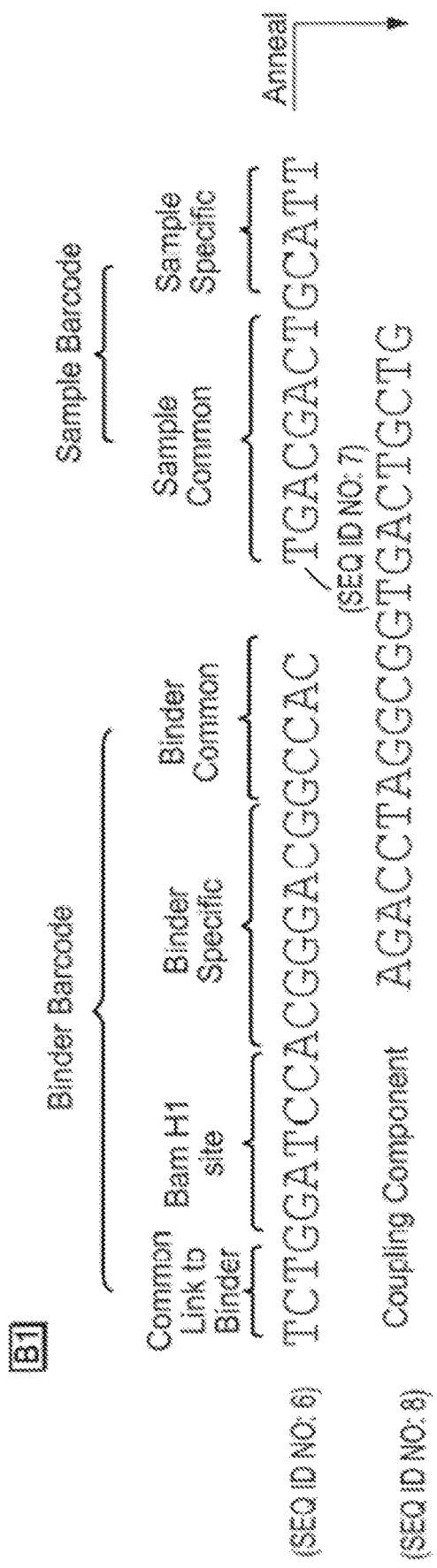
Figure 10B:
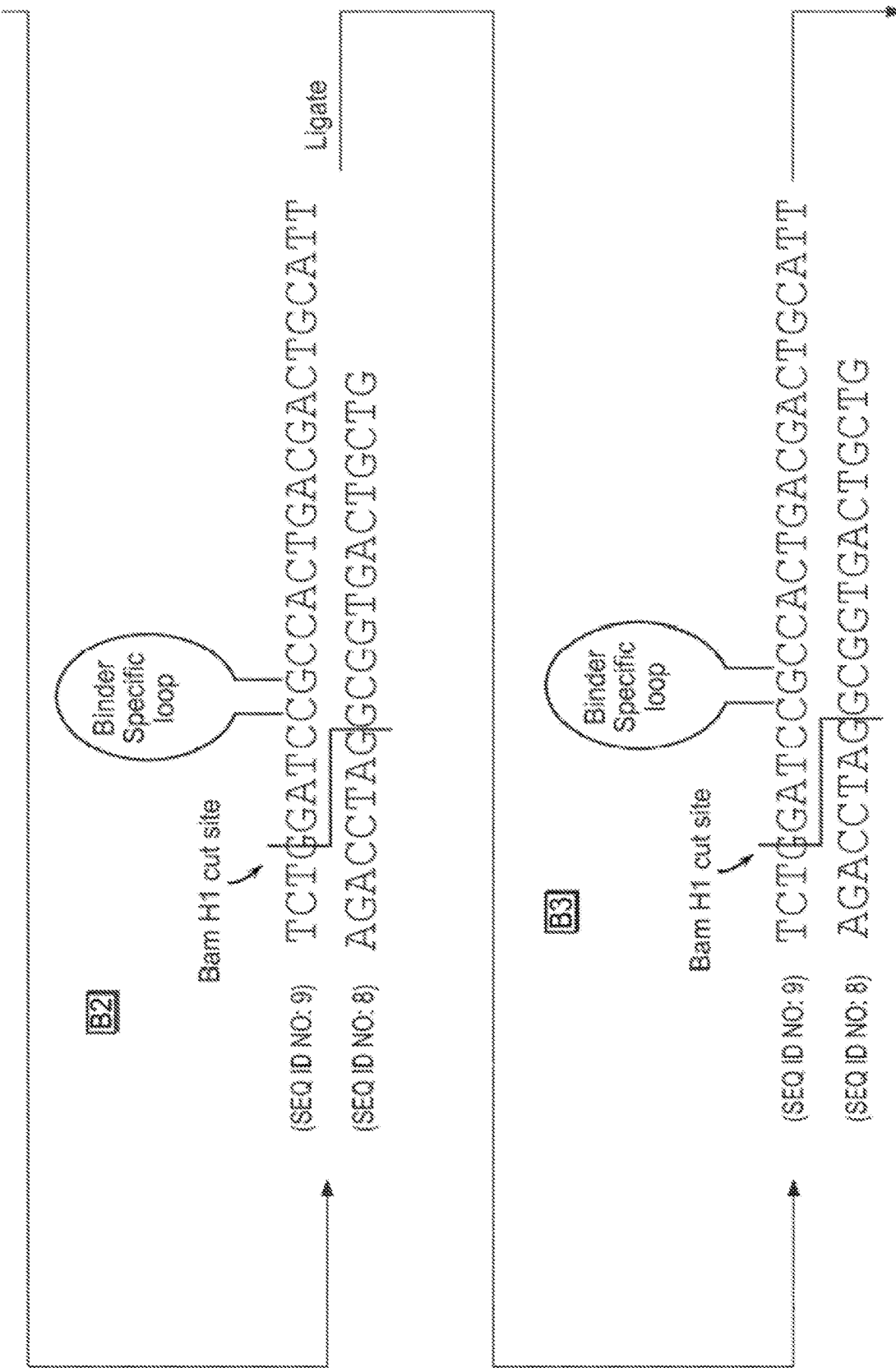
Figure 10C:
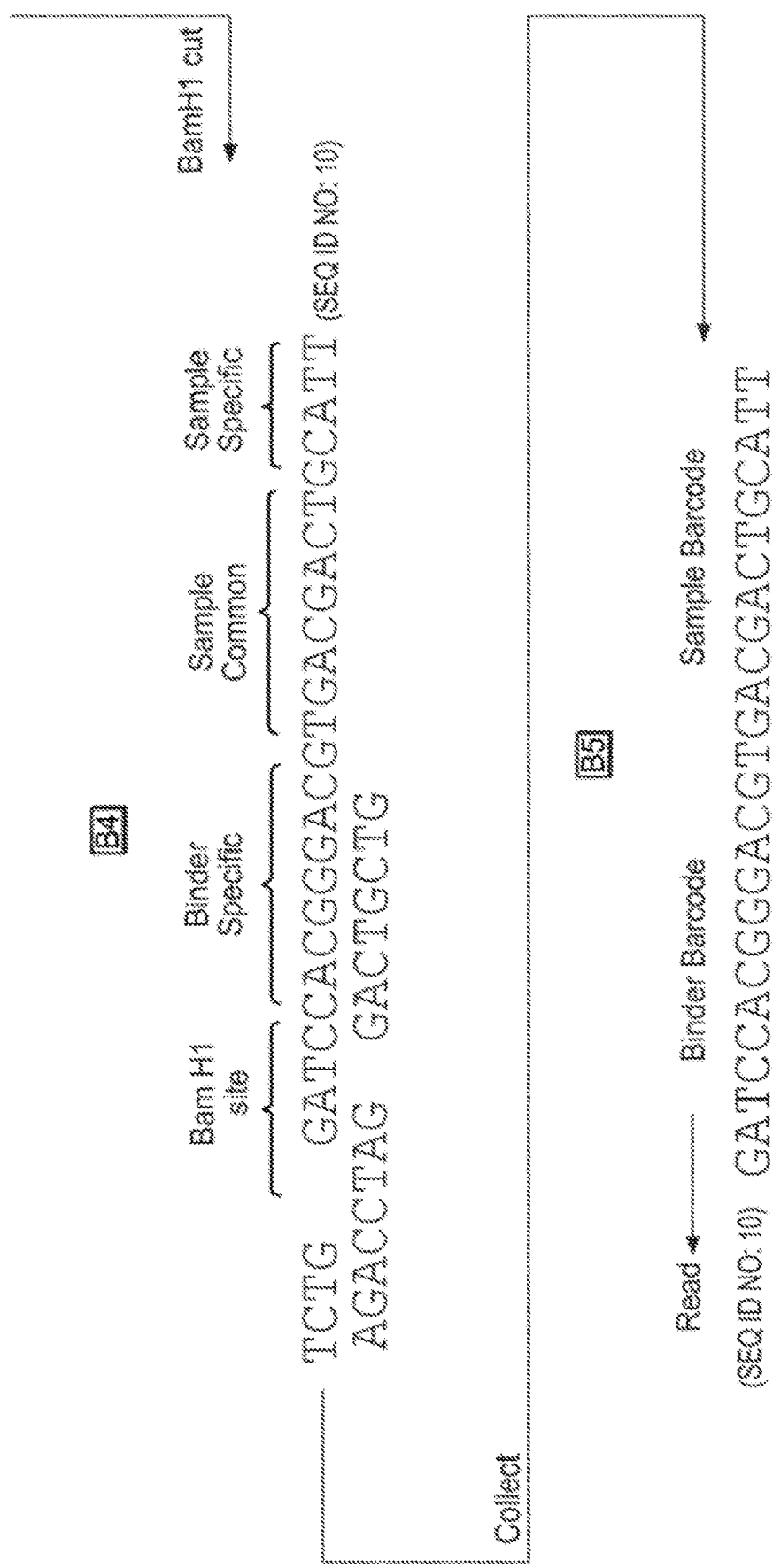

Another method of the invention provides for creating a sample identifier to provide more coding information. In one embodiment, the sample identifier contains information towards identifying that the target analyte came from a certain sample, but sample identifier information may be any extra information useful in analyzing the target analyte. The sample identifier is linked to the target analyte identifier, when the sample and library droplet are combined. One embodiment includes a sample identifier and an identifier linking component within a sample droplet., or the sample linking component can be introduced along with the library droplet, or added in a subsequent step (e.g. another combination or addition to the combined sample and library droplet). In one embodiment, the sample droplet is merged with a library droplet containing a first binding agent having a target analyte identifier and a capture-tagged molecule. When the droplets are merged, a sandwich of the target analyte, first binding agent, and capture-tagged molecule is formed and the sample identifier litigates with the target analyte identifier. In certain embodiments the identifier linking component is a stabilizing molecule to facilitate the ligation of the sample identifier and the target analyte identifier. In certain embodiments, the identifier linking template is not needed, and litigation of the identifier occurs, for example, from affinity of one identifier to the second identifier followed by a reactive step (e.g. ligase, chemical catalysis, light-induced). The unattached sample components are then removed leaving only the isolated sandwich. The combined sample and target analyte identifier are then used to analyze, identify and quantify the target analyte. FIGS. 8A-B demonstrate an embodiment of the invention for creating sandwich assays in combination with combining a sample barcode identifier to a target analyte barcode identifier. In FIG. 8A) Sample Barcode and the Barcode Linking Template are added to bulk Sample A, then made into droplets; FIG. 8B) Sample and Library droplets are combined and incubated to form a sandwich in the presence of the analyte. The Binder Barcode is coupled to the Sample Barcode (e.g. Binder Barcode terminal modified base (*) is photo-ligated to the 5-prime terminal modified base (*) on the Sample Barcode); D) The droplet contents are released and the full sandwich on the capture surface is washed. The Combined Barcode is released (e.g. photo-release); E) Reads for each barcode are counted (e.g. using sequencing). FIGS. 9A through 9B and FIGS. 10A through 10B depict two embodiments of the invention wherein the Binder Barcode and the Sample Barcode are combined into one barcode for analysis. In FIG. 9A, modified oligonucleotides are present in the 5-prime terminus of the Sample Barcode and the 3-prime terminus of the Binder Barcode, such that when they are brought together by the Coupling Component (here a oligonucleotide template) and irradiated with 366 nm wavelength light, a photo-catalyzed reaction forms a covalent coupling (e.g. here using 4-thiothymidine (T*)), thus resulting in a combined sample and target analyte identifier. The Coupling Component is melted off, and the final identifier can be released by a photo-cleavage method (using a shorter wavelength). In FIG. 10A, a ligase is used to combine the two barcodes, with the Coupling Component template to align, followed by release using a restriction enzyme site. In FIG. 10A The Barcode Binder, the Sample Barcode and the Barcode Coupling Component (e.g. template spanning the two barcodes) are in the same droplet and; (FIG. 10B) bind as a complex during incubation. The Barcode Coupling Component is a nucleic acid template that hybridizes to both the 5-prime and 3-prime end of the Binder Barcode (forming a hairpin) and the 5-prime end of the Sample Barcode; (FIG. 10C) The 3-prime end of the Binder Barcode is ligated onto the 5-prime end of the Sample Barcode using a ligase; The annealed 5-prime end of the ligated Combined Barcode encodes a restriction endonuclease site that can be cleaved for release of the Combined Barcode.

Another method of the invention provides for a sample identifier to provide more unique coding information. The sample identifier is introduced into the assay to ligate to the target analyte identifier to provide layered information about the target analyte, for example the target analyte is X-protein and X-protein came from sample-Y. In one embodiment, the sample identifier contains identifying information that the target analyte came from a certain sample. The sample identifier, however, may be coded to contain any extra information useful in analyzing the target analyte.

Detection, Reading and Counting Identifiers

Any detection method can be used that is suitable for the type of label employed. Thus, exemplary detection methods include radioactive detection, optical absorbance detection, e.g., UV-visible absorbance detection, optical emission detection, e.g., fluorescence, chemiluminescence, or phosphorescence, Raman scattering, magnetic detection, or mass spectral detection. For fluorescence labeling, a fluorescence microscope apparatus, such as described in Fodor (U.S. Pat. No. 5,445,934) and Mathies et al. (U.S. Pat. No. 5,091,652), may be used to detect the identifiers. Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993), such as described in Yershov et al., Proc. Natl. Acad. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. A number of approaches can be used to detect the identifiers. Optical setups include near-field scanning microscopy, far-field confocal microscopy, wide-field epi-illumination, light scattering, dark field microscopy, photoconversion, single and/or multiphoton excitation, spectral wavelength discrimination, fluorophor identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use TIRF microscopy for imaging. TIRF microscopy uses totally internally reflected excitation light and is well known in the art. See, e.g., the World Wide Web at nikon-instruments.jp/eng/page/products/tirfaspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached template/primer complex in the presence of a polymerase. Total internal reflectance fluorescence microscopy is then used to visualize the attached template/primer duplex and/or the incorporated nucleotides with single molecule resolution.

According to some embodiments of the invention, after barcoded sandwich complexes have been isolated from the remaining components of the sample, the barcode sequences are released from the first binding agents. In one embodiment, the barcode sequences are joined to each other to produce a single contiguous molecule containing multiple barcodes in series. The individual barcodes, collections of separate barcodes, or individual or collections of multiple barcodes connected in series or other arrangements can be detected with or without amplification. In one embodiment, the barcode or barcode collections are subjected to an amplification reaction (e.g., PCR or rolling circle amplification) to produce multiple linear copies (concatamers), linked end-to-end. The amplification products are then sequenced.

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton ($H^+$), which signal detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using a electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

Additional detection methods can utilize binding to microarrays for subsequent fluorescent or non-fluorescent detection, barcode mass detection using a mass spectrometric methods, detection of emitted radiowaves, detection of scattered light from aligned barcodes, fluorescence detection using quantitative PCR or digital PCR methods.

Single-Plex Assay Vs. Multi-Plex Assays

All of the previous and following embodiments can be performed as either 'single-plex' or 'multi-plex' assays.

In one embodiment, a combined droplet is formed to allow "single-plex" binding to take place between target analyte and a first binding agent and a capture molecule. The single-plex binding interaction avoids any cross-reactivity which may be found when multiple binding agents are mixed together and may correspond to similar target analytes. FIGS. 5A-B depict creation of single-plex assay. In FIGS. 5A-B: A) Two binding reagents types are constructed: Barcoded Binders and Capture-Tag Binders; B) Pairs of target-specific binders are made into a droplet library (with 'n' elements), with each set of target binders in separate droplets; C) The sample is made into sample droplets, and D) combined with the library droplets to initiate highly parallel 'single-plex' binding reactions. After binding is complete, productive sandwiches are E) captured via the capture-tag (streptavidin (SA) biotin (B) interaction shown), and washed to remove unbound material; F) The captured barcodes are released, recovered, and processed for reading; G) Reads for each barcode are counted (e.g. using sequencing). Another embodiment allows for multi-plex interaction within merged droplet. In order to create multi-plex assays, the first binding agent and second binding agents along with their target analyte have been tested and shown not to cross-react with a second, third, or N-number binding agents and the corresponding second, third or N-number target analytes during sandwich formation. In such embodiment, multiple binding agents are within a droplet library and merged with a sample droplet, wherein multiple target analyte sandwiches are formed with the same specificity as if the combining were performed as a single-plex assay.

In another exemplifying embodiment, a combined droplet is formed to allow "multi-plex" binding to take place between multiple target analytes and multiple first binding agents and multiple capture molecules, i.e. multiple second binding agents with binding pairs. A sample droplet contains a first, second, . . . , N-number target analytes. A droplet library contains a first, second, . . . , N-number first binding agents having an identifier that correspond to a first, second, . . . , N-number second binding agents. The droplets merge to create a first target analyte sandwich, a second target analyte sandwich, . . . , a N-number target analyte sandwich. After immobilization, the unbound sample is washed away, leaving multiple sandwich assays. The barcodes of all the assays are released and processed allowing for complex sample analysis.

In one embodiment, the methods previously described are used for quantification of individual proteins from homogenous liquids, including but not limited to bodily fluids, cell and tissue lystates, and biochemical fractions. Within an embodiment, the amount of a target protein within a sample is determined using a binding agent with an identifier and a capture molecule specific to different regions on a target protein. The target protein specific identifier and capture molecules represent a binding pair. The binding agent with the identifier and the capture molecule attached to different epitopes on the target protein, thus creating a sandwich complex. The identifier contains identifying information about specific protein, and in one embodiment the identifier a barcode. The identifier may also contain information about the paired capture molecule. Targeting two separate regions with binding pairs increases specificity of the sample. The capture molecule is immobilized to a solid support. After immobilization, the sample is stringently washed removing unattached sample, identifiers, and capture molecules. The remaining sandwich complexes highly correlate with the amount of targeted protein within the sample. An embodiment of the invention provides for releasing the identifier from the sample, for example releasing a barcode by UV photocleavage. The identifier is then counted using sequencing after ligation with NextGen sequencing adapters and sequencing primers. Other methods of ligation may be applied to the identifier to prepare for sequencing. An example of a single target analyte sandwich is shown in FIG. 6A. The above method is not limited to single target proteins and allows for quantification of any single target analyte.

Another embodiment provides for quantification of protein complexes. Protein complexes includes any combination of two or more polypeptide chains, for example epidermal growth factor receptor dimers, a ribosome, a proteasome, a transcription activation pre-initiation complex. Utilizing the sandwich assay method previously described, the protein complex may be identified and counted using identifiers, in certain embodiments the identifiers include barcodes. In one embodiment, a droplet containing a targeted protein complex merged with a library droplet containing a capture molecule specific a first protein complex member and a corresponding binding agent with an identifier specific to second first complex member suspected in the target protein complex. A sandwich is formed wherein the capture molecule is bound to the first protein complex member and the identifier is bound to a second protein complex member. The attached capture molecule then immobilizes the sandwich to a solid substrate, allowing for a stringent wash to remove all unbound sample, identifiers and capture molecules. The remaining sandwiches highly correlate to the amount of targeted protein complexes within the sample. The identifier is released. In one embodiment a barcode attached to the identifier is released using UV photocleavage. Once released, the barcode undergoes ligation with NextGen sequencing adapters and sequencing primers, or other suitable ligation techniques, and then counted using sequencing. An example of a complex sandwich assay is shown in FIG. 6B. The above method is not limited to protein complexes and allows for quantification of any complex analyte containing more than one member.

In a further embodiment, complexes may also be identified and counted using methods of the invention described above. Identifiers specific to complex members can contain identifying information about the target complex member to which they attach (i.e. binder information), but also can contain identifying information relating to the capture molecule or additional binders present in the library droplet. Therefore, the first identifier contains identifying information about the second complex member and the capture molecule, and the second identifier contains identifying information about a third protein complex member and the capture molecule. An example of a complex analyte sandwich is shown in FIG. 6C (e.g. "3:1:2" in example C means Binder3 in the same droplet as Binder1 and Capture-Tag Binder2).

In a another embodiment, quantification of post-translational modifications from homogenous liquids including bodily fluids, cell and tissue lysates, and biochemical fractions. Post-translational modifications of proteins include phosphorylation, methylation, glycosylation, and ubiquitinylation and are critical components of protein function. Methods of the invention allow for identifying and quantifying specific post-translational modification proteins within a sample. In one embodiment a binding agent is specific to a invariant epitope and the other biding agent is specific to a sequence-specific post-translational modification. In one embodiment, a first binding agent with an identifier, in one embodiment a barcode, is specific to an invariant epitope on the target protein, and a capture molecule is specific to sequence-specific post-translational modification. When introduced to the target protein, the target protein forms a sandwich with the first binding agent and the capture molecule. The sandwich is separated from unattached samples and binding agents, wherein separation may occur from immobilization followed by a stringent wash. The remaining sandwiches highly correlate to the amount of target proteins having the post-translational modification. In one embodiment, the identifier is released from the sandwich by a UV photocleavage and the identifier is then used to analyze the target protein. In one embodiment, the barcode is ligated using NextGen sequencing adapters and sequencing primers and then analyzes the target protein via sequencing. Example of a single sandwich wherein the target analyte is a post-translation modification is illustrated on FIG. 6D. Modifications that can be detected using the above methods are not limited to post-translational protein modifications, but apply to any modification for which a specific binding agent is available.

Methods of the invention also provide for quantification of individual nucleic acids from homogenous liquids (liquids including bodily fluids, cell and tissue lysate, and biochemical fractions). In one embodiment, a specific region on a nucleic may be detected using methods of the invention. A first binding agent is specific to a first region on the nucleic acid, and a second binding agent specific to the second region on the nucleic acid. The first or the second binding agent may comprise a capture molecule or having an identifier. When the first and second binding agents attach to the corresponding regions on the target region and a sandwich is produced. In one embodiment, a sandwich is created for SNP detection of DNA wherein the capture molecule is specific to a target wild type sequence nearby the potential SNP-containing sequence and the binding agent having a identifier is specific to potential SNP (see FIG. 6H). In another embodiment, a gene fusion is detected wherein the capture molecule is specific to target sequences nearby the potential fusion junction on gene 1 and the binding agent having a identifier is specific to sequences found on gene 2 when fused to gene 1 (see FIG. 6I). In another embodiment, full-length mRNA is detected wherein the capture molecule is specific to the transcriptional start sequence region and the identifier is specific to the 3-prime end region (See FIG. 6F). In another embodiment, splice variants are detected wherein a capture molecule is specific to the transcriptional start sequence region and the binding agent is specific to the splice variant region (see FIG. 6G). In another embodiment, modified DNA (e.g. methylation or hydroxyl-methylation of cytosine) is detected using a capture molecule specific to a nearby DNA motif and a barcoded binding agent specific for modified DNA sequences. Other embodiments of the invention includes detecting untranslated RNA (including miRNA or lincRNA), and binding complexes of DNA to DNA, DNA to RNA, DNA or RNA to protein (see FIG. 6E). In a further embodiment, introduction of a competitive inhibitor increases specificity to ensure the binding agent or capture molecule are not binding on unspecific target regions (similar to the example in FIG. 7).

Embodiments of the invention further include using sandwich assays in droplets for quantification of proteins, nucleic acids, and other molecules from single cells. An embodiment of the invention provides for encapsulating a series of single cell containing droplets by using collections of single cells dispersed in liquid, for example a growth media or a phosphate buffered saline for droplet creation similar to methods described above. In order to create droplets containing only single cells, the concentration of single cells in a collection is diluted to minimize multiple cell encapsulation. One embodiment of the invention dilutes the single cell concentration to a level where only one cell is present for every 10 droplets formed. Once single cell droplets are formed, they are incubated in order to allow secreted molecules of interest to accumulate inside the droplet, one can lyse the cell using reagents that release the cellular nucleic acids, proteins, and other components from cell compartments, or one can use immediately to analyze cell surface exposed material, or one can combine these various analysis schemes. Each single cell droplet is combined with a library droplet in which a variety of assays may be conducted using methods of the invention including 1) analysis of secreted molecules including but not limited to cytokines and growth factors by combining viable single cells with a first binding agent and a second binding agent specific to target secreted molecules; 2) analysis of cell surface molecules including but not limited to receptors and biomarkers by combining a single cell with a droplet library containing a first binding agent and a second binding agent specific to target molecules; 3) analysis of molecules released from single cells lysed inside droplets including but not limited to cytoplasmic or nuclear proteins by combining lysed single cell droplets with a first binding agent and a second binding agent specific to a target intracellular molecule; 4) any combination of the above assays.

Methods of the invention further provide for conducting further assays previously described for use with single cell droplets, including quantification of individual proteins, protein post-translational modifications, protein complexes, protein/DNA complexes, and nucleic acids. In further embodiments, a combination of assays may be performed. In a non-limiting example, an assay may be performed by targeting both secreted molecules and cell surface molecules from the same cell. In another non-limiting example, a secreted target can be assayed before cell lysis is induced, followed by cell lysis within the droplet and subsequently assaying an intracellular target using additional binding and capture agents in the library element, or by subsequent combination with a second library element droplet. Typical, but non-limiting methods for cell lysis within droplets include: 1) co-flowing a lysis buffer in a laminar flow alongside the incoming cell stream in the flow path just before the droplet-forming microfluidic nozzle; 2) introducing a lysis buffer within the droplet library reagents; 3) use of a temperature or other inducible protease or lysis reagent; 4) mechanical abrasion inside droplets traveling through microfluidic turns and constrictions; 5) laser-induced lysis. Library droplets used for single cell analysis can contain paired binders for single-target analysis, or multiple binding pairs for multi-plex target analysis (as long as the multiple binding pairs retain sufficient specificity when in the same compartment). In a preferred embodiment, the single cell droplet contains a sample identifier and all individual molecule droplets dependent from the sample also have the same sample identifier. Therefore, the sample identifier combines with the target analyte identifier so all sandwiches can be traced to the sample.

In another embodiment, target analyte sandwiches are run on bulk samples without the need for droplets, if cross reactivity or specificity of binding pairs in the presence of other binding pairs is not an issue. In such embodiment, a identifier library is created to analyze the target analytes within the sample without the use of droplets, and all related steps needed for quantifying the analytes with use of barcodes also do not require droplets, i.e. capture occurs on beads in a bulk solution instead of in a droplet.

Libraries and Kits

Droplet libraries are useful to perform large numbers of assays while consuming only limited amounts of reagents. A "droplet," as used herein, is an isolated portion of a first fluid that completely surrounded by a second fluid. In some cases, the droplets may be spherical or substantially spherical; however, in other cases, the droplets may be non-spherical, for example, the droplets may have the appearance of "blobs" or other irregular shapes, for instance, depending on the external environment. As used herein, a first entity is "surrounded" by a second entity if a closed loop can be drawn or idealized around the first entity through only the second entity.

In general, a droplet library is made up of a number of library elements that are pooled together in a single collection. Libraries may vary in complexity from a single library element to $10^{15}$ library elements or more. Each library element is one or more given components at a fixed concentration. Each droplet includes a first binding agent having a differentially detectable identifier and a second binding agent. The binding agents may be any of the agents described above. Each droplet may further include a sample identifier that can bind to the identifier linked to the first binding agent. In this manner, each droplet includes an identifier for a particular target analyte and an identifier for a specific droplet. Each droplet may further include a competitive inhibitor. The terms "droplet library" or "droplet libraries" are also referred to herein as an "emulsion library" or "emulsion libraries." These terms are used interchangeably throughout the specification.

The droplets range in size from roughly 0.5 micron to 500 micron in diameter, which corresponds to about 1 pico liter to 1 nano liter. However, droplets can be as small as 5 microns and as large as 500 microns, Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the droplet library provided by the instant invention may be uniform in size. That is, the diameter of any droplet within the library will vary less than 5%, 4%, 3%, 2%, 1% or 0.5% when compared to the diameter of other droplets within the same library. The uniform size of the droplets in the library is critical to maintain the stability and integrity of the droplets and is also essential for the subsequent use of the droplets within the library for the various biological and chemical assays described herein.

The droplet libraries of the present invention are very stable and are capable of long-term storage. The droplet libraries are determined to be stable if the droplets comprised within the libraries maintain their structural integrity, that is the droplets do not rupture and elements do not diffuse from the droplets. The droplets libraries are also determined to be stable if the droplets comprised within the libraries do not coalesce spontaneously (without additional energy input, such as electrical fields described in detail herein). Stability can be measured at any temperature. For example, the droplets are very stable and are capable of long-term storage at any temperature; for example, e.g., −70° C., 0° C., 4° C., 37° C., room temperature, 75° C. and 95° C. Specifically, the droplet libraries of the present invention are stable for at least 30 days. More preferably, the droplets are stable for at least 60 days. Most preferably, the droplets are stable for at least 90 days.

In certain embodiments, the present invention provides an emulsion library comprising a plurality of aqueous droplets within an immiscible fluorocarbon oil comprising at least one fluorosurfactant, wherein each droplet is uniform in size and comprises the same aqueous fluid and comprises a different library element. The present invention also provides a method for forming the emulsion library comprising providing a single aqueous fluid comprising different library elements, encapsulating each library element into an aqueous droplet within an immiscible fluorocarbon oil comprising at least one fluorosurfactant, wherein each droplet is uniform in size and comprises the same aqueous fluid and comprises a different library element, and pooling the aqueous droplets within an immiscible fluorocarbon oil comprising at least one fluorosurfactant, thereby forming an emulsion library.

For example, in one type of emulsion library, the first and second binding agents are pooled in a single source contained in the same medium. After the initial pooling, the first and second binding agents are then encapsulated in droplets to generate a library of droplets wherein each droplet includes a different set of first and second binding agents. The dilution of the initial solution enables the encapsulation process. In some embodiments, the droplets formed will either contain a single set of first and second binding agents or having nothing, i.e., be empty. In other embodiments, the droplets formed will contain multiple sets of first and second binding agents so that multiplexing may be performed in each droplet.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. An analysis method comprising:
   encapsulating cells into a plurality of droplets to create at least one droplet containing a single cell, wherein the droplet includes one or more binding agents, wherein the binding agents provide an analyte identifier for a target analyte and an identifier specific for the droplet;
   lysing the cell within the droplet to release the target analyte;
   binding the one or more binding agents to the target analyte; and
   detecting the target analyte identifier, thereby detecting the target analyte.

2. The method of claim 1, wherein the identifier specific for the droplet is detected to associate the detection of the target analyte with the droplet.

3. The method of claim 1, wherein the target analyte is a protein or a nucleic acid.

4. The method of claim 1, wherein encapsulating the cells into the plurality of droplets includes diluting the concentration of single cells in a collection to a level where less than about one cell is present for every 10 droplets formed.

5. The method of claim 1, wherein the lysing step involves exposing the cell to lysis reagents that release the cellular nucleic acids, proteins, and other components from the cell.

6. The method of claim 1, wherein the detecting step provides for analysis of molecules released from single cells lysed inside droplets, wherein the molecules include cytoplasmic or nuclear proteins.

7. The method of claim 1, wherein the one or more binding agents include a first barcoded binder that includes the analyte identifier.

8. The method of claim 7, wherein the analyte identifier comprises an oligonucleotide sequence that constitutes a unique identifier or barcode.

9. The method of claim 7, wherein the first barcoded binder is a nucleic acid with a barcode sequence attached thereto.

10. The method of claim 9, wherein the barcode sequence is designed to include no homopolymer repeats.

11. The method of claim 1, wherein the lysing step includes one selected from the group consisting of: (1) co-flowing a lysis buffer in a laminar flow alongside the incoming cell stream in the flow path just before the droplet-forming microfluidic nozzle; (2) introducing a lysis buffer within droplet library reagents; (3) use of a temperature or other inducible protease or lysis reagent; (4) mechanical abrasion inside droplets traveling through microfluidic turns and constrictions; and (5) laser-induced lysis.

12. The method of claim 1, wherein one or more of the plurality of droplets include multiple sets of binding pairs for multi-plex target analysis.

13. The method of claim 1, wherein the droplet further contains a sample identifier and all individual analyte molecules from the cell are labeled with the sample identifier.

14. The method of claim 13, wherein the sample identifier combines with the analyte identifier so all analytes can be traced to a sample.

15. The method of claim 1, wherein the detecting step comprises nucleic acid sequencing.

16. A droplet library comprising:
a plurality of droplets, wherein at least one droplet comprises, in an aqueous phase fluid,
a single cell,
one or more binding agents that provide an analyte identifier for a target analyte and an identifier specific for the droplet, and
lysis reagents to lyse the cell.

17. The library of claim 16, further comprising a number of library elements, each element comprising a single cell encapsulated in a droplet, that are pooled together in a single collection.

18. The library of claim 16, wherein the one or more binding agents include a first barcoded binder that includes the analyte identifier.

19. The library of claim 18, wherein the analyte identifier comprises an oligonucleotide sequence that constitutes a unique identifier or barcode.

20. The library of claim 19, wherein the first barcoded binder is a nucleic acid with a barcode sequence attached thereto.

* * * * *